US010487328B2

(12) United States Patent
Kumar et al.

(10) Patent No.: US 10,487,328 B2
(45) Date of Patent: Nov. 26, 2019

(54) BLOCKING HEPATITIS C VIRUS INFECTION ASSOCIATED LIVER TUMOR DEVELOPMENT WITH HCV-SPECIFIC ANTISENSE RNA

(71) Applicant: Ajit Kumar, Bethesda, MD (US)

(72) Inventors: Ajit Kumar, Bethesda, MD (US); Nagarajan Pattabiraman, North Potomac, MD (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 0 days.

(21) Appl. No.: 15/129,043

(22) PCT Filed: Mar. 25, 2015

(86) PCT No.: PCT/US2015/022423

§ 371 (c)(1),
(2) Date: Sep. 26, 2016

(87) PCT Pub. No.: WO2015/148624

PCT Pub. Date: Oct. 1, 2015

(65) Prior Publication Data

US 2017/0191061 A1 Jul. 6, 2017

Related U.S. Application Data

(60) Provisional application No. 62/076,500, filed on Nov. 7, 2014, provisional application No. 61/970,022, filed on Mar. 25, 2014.

(51) Int. Cl.
*C12N 15/113* (2010.01)
*A61K 31/7105* (2006.01)
*A61K 31/712* (2006.01)
*A61K 31/7125* (2006.01)

(52) U.S. Cl.
CPC ........ *C12N 15/1131* (2013.01); *A61K 31/712* (2013.01); *A61K 31/7105* (2013.01); *A61K 31/7125* (2013.01); *C12N 2310/11* (2013.01); *C12N 2310/32* (2013.01); *C12N 2310/3231* (2013.01); *C12N 2320/51* (2013.01)

(58) Field of Classification Search
None
See application file for complete search history.

(56) References Cited

U.S. PATENT DOCUMENTS

| | | | | |
|---|---|---|---|---|
| 7,795,419 | B2 | 9/2010 | Bentwich et al. | |
| 2007/0123482 | A1* | 5/2007 | Stoffel ................ | C12N 15/113 514/44 A |
| 2007/0253953 | A1 | 11/2007 | Chen et al. | |
| 2012/0225477 | A1 | 9/2012 | Bentwich et al. | |

FOREIGN PATENT DOCUMENTS

WO WO 2015/148624 A1 10/2015

OTHER PUBLICATIONS

Martinez-Sanchez et al (Biology 2013, 2: 189-205).*
Rahman et al (Int. J. Cancer 100:152-157, 2002).*
Ning et al (Cancer Res; 70(19): 7640-7651, 2010).*
Walesky et al (Hepatology 57(6): 2480-2490, 2013).*
Yin et al (Hepatology 58(6):1964-1976, 2013).*
Yin et al (Hepatology 48(5):1528-1539, 2008).*
Andrade et al (J. Global infect. Dis. 1(1): 33-37, 2009).*
Arzumanyan et al (Nature Reviews: Cancer 13:123-135, 2013).*
Hazari et al (World J Gastroenterol Jan. 21, 2011; 17(3): 300-312).*
Krutzfeld et al. (Nature 438:685-689, 2005) (Year: 2005.*
Sotillo et al. (Pharmacology & Therapeutics 131 (2011) 18-32) (Year: 2011).*
Janssen et al.(N Engl J Med 2013;368:1685-94) (Year: 2013).*
Thibault et al. (Pharmacological Research 75 (2013) 48-59 (Year: 2013).*
Baker, Suzanne J. "PTEN enters the nuclear age." Cell (2007); 128.1: 25-28.
Banaudha, Krishna, et al. "MicroRNA Silencing of Tumor Suppressor DLC-1 Promotes Efficient Hepatitis C Virus Replication in Primary Human Hepatocytes." Hepatology (2011); 53.1: 53-61.
Banaudha, Krishna, et al. "Primary Hepatocyte Culture Supports Hepatitis C Virus Replication: A Model for Infection-Associated Hepatocarcinogenesis." Hepatology (2010); 51.6: 1922-1932.
Bao, Wenjie, et al. "Loss of nuclear PTEN in HCV-infected human hepatocytes." Infectious Agents and Cancer (2014); 9.1: 23, pp. 1-11.
Bao, Wenjie. "Hepatitis C Virus Derived Small RNA, vmr11, Inhibits Nuclear PTEN Accumulation in Primary Human Hepatocytes." Diss. The George Washington University, 2012, 46 pages.
Calin, George A., and Croce, Carlo M. "MicroRNA signatures in human cancers." Nature Reviews Cancer (2006); 6.11: 857-866.
Calin, George Adrian, et al. "Frequent deletions and down-regulation of micro-RNA genes miR15 and miR16 at 13q14 in chronic lymphocytic leukemia." Proceedings of the National Academy of Sciences (2002); 99.24: 15524-15529.
Chang, Chun-Ju, et al. "PTEN Nuclear Localization Is Regulated by Oxidative Stress and Mediates p53-Dependent Tumor Suppression." Molecular and Cellular Biology (2008); 28.10: 3281-3289.
Clément, Sophie, et al. "Downregulation of PTEN and IRS-1 by HCV 3a core protein triggers the formation of large lipid droplets in hepatocytes." Hepatology (2011); 54: 38-49.
Ding, Shou-Wei, and Voinnet, Olivier. "Antiviral Immunity Directed by Small RNAs." Cell (2007); 130.3: 413-426.
Foster, Elinor R., and Downs, Jessica A. "Histone H2A phosphorylation in DNA double-strand break repair." The FEBS Journal (2005); 272.13: 3231-3240.
Gallouzi, Imed-Eddine, and Steitz, Joan A. "Delineation of mRNA Export Pathways by the Use of Cell-Permeable Peptides." Science (2001); 294.5548: 1895-1901.

(Continued)

*Primary Examiner* — Richard A Schnizer
(74) *Attorney, Agent, or Firm* — Cooley LLP

(57) ABSTRACT

The disclosure teaches antagonists of Hepatitis C Virus (HCV) derived microRNA, which are useful in methods for treating and protecting against HCV-mediated hepatocellular carcinogenesis.

12 Claims, 31 Drawing Sheets

Specification includes a Sequence Listing.

(56) References Cited

OTHER PUBLICATIONS

Garaigorta, Urtzi, and Chisari, Francis V. "Hepatitis C Virus Blocks Interferon Effector Function by Inducing Protein Kinase R Phosphorylation." Cell Host & Microbe (2009); 6.6: 513-522.
Grassmann, Ralph, and Jeang, Kuan-Teh. "The roles of microRNAs in mammalian virus infection." Biochimica et Biophysica Acta (BBA)-Gene Regulatory Mechanisms (2008); 1779.11: 706-711.
Grey, Finn, et al. "A Human Cytomegalovirus-Encoded microRNA Regulates Expression of Multiple Viral Genes Involved in Replication." PLoS Pathogens (2007); 3.11: e163, pp. 1593-1602.
Grundhoff, Adam and Sullivan, Christopher S., "Virus-encoded microRNAs." Virology (2011); 411.2: 325-343.
Hatziapostolou, Maria, et al., "An HNF4α-miRNA Inflammatory Feedback Circuit Regulates Hepatocellular Oncogenesis." Cell (2011); 147.6: 1233-1247.
He, Lina, et al., "The Critical Role of AKT2 in Hepatic Steatosis Induced by PTEN Loss." The American Journal of Pathology (2010); 176.5: 2302-2308.
He, Xin, et al., "PTEN Lipid Phosphatase Activity and Proper Subcellular Localization Are Necessary and Sufficient for Down-Regulating AKT Phosphorylation in the Nucleus in Cowden Syndrome." J Clin Endocrinol Metab (2012); 97(11): E2179-E2187.
Herbert, Alan, et al. "A Z-DNA binding domain present in the human editing enzyme, double-stranded RNA adenosine deaminase." Proceedings of the National Academy of Sciences (1997); 94.16: 8421-8426.
Herbert, Alan, et al., "The Zα domain from human ADAR1 binds to the Z-DNA conformer of many different sequences." Nucleic Acids Research (1998); 26.15: 3486-3493.
Hofacker, Ivo L., "Vienna RNA secondary structure server." Nucleic Acids Research (2003); 31.13: 3429-3431.
Horie, Yasuo, et al. "Hepatocyte-specific Pten deficiency results in steatohepatitis and hepatocellular carcinomas." The Journal of Clinical Investigation (2004); 113.12: 1774-1783.
Houzet, Laurent, and Jeang, Kuan-Teh. "MicroRNAs and human retroviruses." Biochim Biophys Acta. (2011); 1809.11: 686-693.
International Preliminary Report on Patentability in International Application No. PCT/US2015/022423, dated Sep. 27, 2016, 12 pages.
International Search Report and Written Opinion in International Application No. PCT/US2015/022423, dated Aug. 19, 2015, 15 pages.
Janssen, Harry LA, et al. "Treatment of HCV Infection by Targeting MicroRNA." New England Journal of Medicine (2013); 368.18: 1685-1694.
Kerr, Thomas A., et al. "MicroRNAs and liver disease." Translational Research (2011); 157.4: 241-252.
Kertesz, Michael, et al. "The role of site accessibility in microRNA target recognition." Nature Genetics (2007); 39.10: 1278-1284.
Kincaid, Rodney P., and Sullivan, Christopher S. "Virus-encoded microRNAs: an overview and a look to the future." PLoS Pathogens (2012); 8.12: e1003018.
Kincaid, Rodney P., et al. "RNA virus microRNA that mimics a B-cell oncomiR." Proceedings of the National Academy of Sciences (2012); 109.8: 3077-3082.
Klase, Zachary, et al. "HIV-1 TAR element is processed by Dicer to yield a viral micro-RNA involved in chromatin remodeling of the viral LTR." BMC Molecular Biology (2007); 8.1: 63, 19 pages.
Kota, J., et al., "Therapeutic delivery of miR-26a inhibits cancer cell proliferation and induces tumor-specific apoptosis." Cell (2009); 137(6): 1005-1017.
Krützfeldt, Jan, et al. "Silencing of microRNAs in vivo with 'antagomirs'." Nature (2005); 438.7068: 685-689.
Kumar, Ajit. "MicroRNA in HCV infection and liver cancer." Biochimica et Biophysica Acta (2011); 1809.11: 694-699.
Leslie, Nick R., and Foti, Michelangelo. "Non-genomic loss of PTEN function in cancer: not in my genes." Trends in Pharmacological Sciences (2011); 32.3: 131-140.
Liu, Helene Minyi, and Gale Jr., Michael. "Hepatitis C virus evasion from RIG-I-dependent hepatic innate immunity." Gastroenterology Research and Practice (2010); Article ID 548390, 8 pages.
Malathi, Krishnamurthy, et al. "RNase L releases a small RNA from HCV RNA that refolds into a potent PAMP." RNA (2010); 16.11: 2108-2119.
Malathi, Krishnamurthy, et al., "Small self-RNA generated by RNase L amplifies antiviral innate immunity." Nature (2007); 448(7155): 816-819.
Medina, Pedro P., and Slack, Frank J. "microRNAs and cancer: an overview." Cell Cycle (2008); 7.16: 2485-2492.
Medina, Pedro P., et al. "OncomiR addiction in an in vivo model of microRNA-21-induced pre-B-cell lymphoma." Nature (2010); 467. 7311: 86-90.
Mendell, Joshua T., and Olson, Eric N. "MicroRNAs in stress signaling and human disease." Cell (2012); 148.6: 1172-1187.
Moradpour, Darius, et al. "Replication of hepatitis C virus." Nature Reviews Microbiology (2007); 5.6: 453-463.
Obad, Susanna, et al. "Silencing of microRNA families by seed-targeting tiny LNAs." Nature Genetics (2011); 43.4: 371-378.
Parameswaran, Poornima, et al. "Six RNA Viruses and Forty-One Hosts: Viral Small RNAs and Modulation of Small RNA Repertoires in Vertebrate and Invertebrate Systems." PLoS Pathogens (2010); 6.2: e1000764, 21 pages.
Pattabiraman, N. "Can the double helix be parallel?." Biopolymers (1986); 25.9: 1603-1606.
Peyrou, Marion, et al. "PTEN in liver diseases and cancer." World Journal of Gastroenterology (2010); 16.37: 4627-4633.
Pfeffer, Sébastien, et al. "Identification of microRNAs of the herpesvirus family." Nature Methods (2005); 2.4: 269-276.
Pineau, Pascal, et al. "miR-221 overexpression contributes to liver tumorigenesis." Proceedings of the National Academy of Sciences (2010); 107.1: 264-269.
Planchon, Sarah M., et al. "The nuclear affairs of PTEN." Journal of Cell Science (2008); 121.3: 249-253.
Puc, Janusz, and Parsons, Ramon. "PTEN loss inhibits CHK1 to cause double stranded-DNA breaks in cells." Cell Cycle (2005); 4.7: 927-929.
Rebane, Ana, et al. "Transportins 1 and 2 are redundant nuclear import factors for hnRNP A1 and HuR." RNA (2004); 10.4: 590-599.
Redon, Christopher E., et al., "γ-H2AX and other histone post-translational modifications in the clinic." Biochimica et Biophysica Acta (2012); 1819.7: 743-756.
Safaee, Nozhat, et al. "Structure of the Parallel Duplex of Poly (A) RNA: Evaluation of a 50 Year-Old Prediction." Angew Chem Int Ed Engl. (2013); 52.39: 10370-10373.
Schade, Markus, et al. "The solution structure of the Za domain of the human RNA editing enzyme ADAR1 reveals a prepositioned binding surface for Z-DNA." Proceedings of the National Academy of Sciences (1999); 96.22: 12465-12470.
Schwartz, Thomas, et al. "Crystal Structure of the Zα Domain of the Human Editing Enzyme ADAR1 Bound to Left-Handed Z-DNA." Science (1999); 284.5421: 1841-1845.
Seo, Jungmin, et al. "Genome-wide profiles of H2AX and γ-H2AX differentiate endogenous and exogenous DNA damage hotspots in human cells." Nucleic Acids Research (2012); 40.13: 5965-5974.
Siomi, Mikiko C., et al. "Transportin-mediated Nuclear Import of Heterogeneous Nuclear RNP Proteins." The Journal of Cell Biology (1997); 138.6: 1181-1192.
Song, Min Sup, et al. "The functions and regulation of the PTEN tumour suppressor." Nature Reviews Molecular Cell Biology (2012); 13.5: 283-296.
Stiles, Bangyan, et al. "Live-specific deletion of negative regulator PTEN results in fatty liver and insulin hypersensitivity." Proceedings of the National Academy of Sciences (2004); 101.7: 2082-2087.
Tani, Hidenori, and Akimitsu, Nobuyoshi. "Genome-wide technology for determining RNA stability in mammalian cells: historical perspective and recent advantages based on modified nucleotide labeling." RNA Biology (2012); 9.10: 1233-1238.
Tani, Hidenori, et al. "Genome-wide determination of RNA stability reveals hundreds of short-lived noncoding transcripts in mammals." Genome Research (2012); 22.5: 947-956.

(56) References Cited

OTHER PUBLICATIONS

Tchurikov, Nickolai A., et al. "Gene-specific Silencing by Expression of Parallel Complementary RNA in *Escherichia coli*." Journal of Biological Chemistry (2000); 275.34: 26523-26529.
Tesfaye, Abeba, et al. "Chimeric Mouse Model for the Infection of Hepatitis B and C Viruses." PLoS One (2013); 8.10 : e77298, 14 pages.
Thiriet, Christophe, and Hayes, Jeffrey J. Chromatin in Need of a Fix: Phosphorylation of H2AX Connects Chromatin to DNA Repair. Molecular Cell (2005); 18.6: 617-622.
Trotman, Lloyd C., et al. "Ubiquitination Regulates PTEN Nuclear Import and Tumor Suppression." Cell (2007); 128.1: 141-156.
Umbach, Jennifer L., and Cullen, Bryan R. "The role of RNAi and microRNAs in animal virus replication and antiviral immunity." Genes & Development (2009); 23.10: 1151-1164.
Von Roretz, Christopher, et al. "Transportin 2 Regulates Apoptosis through the RNA-binding Protein HuR." Journal of Biological Chemistry (2011); 286.29: 25983-25991.
Warfel, Noel A., and El-Deiry, Wafik S. "p21WAF1 and tumourigenesis: 20 years after." Current Opinion in Oncology (2013); 25.1: 52-58.
Watson, J.D. and Crick, F.H.C., "Molecular structure of nucleic acids." Nature (1953); No. 4356, p. 737.
Zhou, Ning, et al. "Solution structure of the parallel-stranded hairpin d (T8<>C4A8) As Determined by Two-Dimensional NMR." Biochemistry (1993); 32.2: 646-656.
Wang, et al., "Viral non-coding RNA inhibits HNF4α expression in HCV associated hepatocellular carcinoma." Infectious Agents and Cancer (2015); 10: 19, pp. 1-9.

* cited by examiner

A

B

C

D

A vmr 11 original 5'-GUUCAUCAUCAUAUCCCAUGCC-3'
vmr 11 mutant 1 5'-CAUCAUCAUCAUAUCCCAUGCC-3'
vmr 11 mutant 2 5'-GUUGUUCAUCAUAUCCCAUGCC-3'
vmr 11 mutant 3 5'-GUUCAUGUUCAUAUCCCAUGCC-3'
vmr 11 mutant 4 5'-GUUCAUCAAGAUAUCCCAUGCC-3'
vmr 11 mutant 5 5'-GUUCAUCAUCCCAUCCCAUGCC-3'
vmr 11 mutant 6 5'-GUUCAUCAUCAUCCCCCAUGCC-3'
vmr 11 mutant 7 5'-GUUCAUCAUCAUAUCCCUAGCC-3'

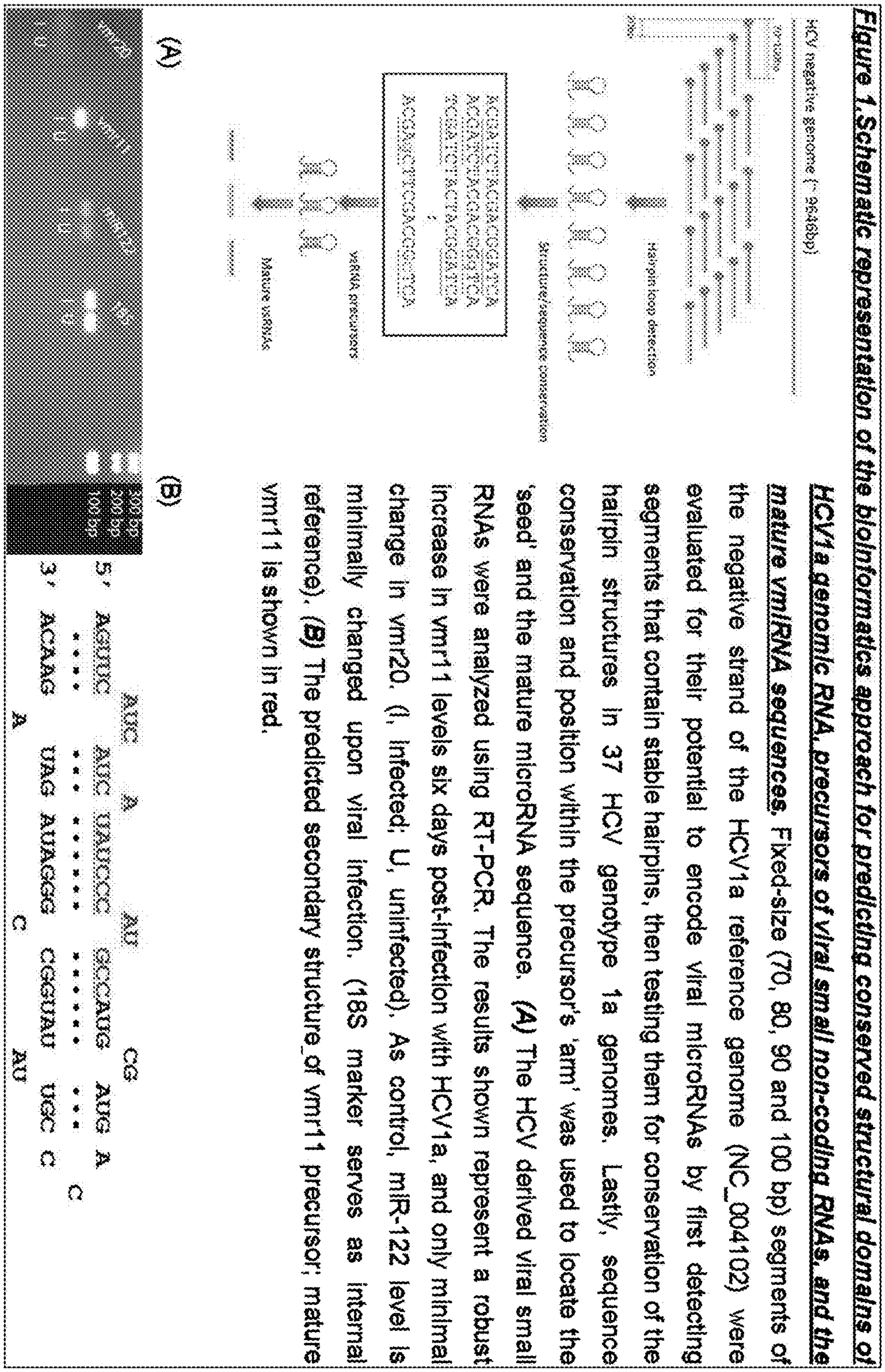

*Figure 1. Schematic representation of the bioinformatics approach for predicting conserved structural domains of HCV1a genomic RNA, precursors of viral small non-coding RNAs, and the mature vmiRNA sequences.* Fixed-size (70, 80, 90 and 100 bp) segments of the negative strand of the HCV1a reference genome (NC_004102) were evaluated for their potential to encode viral microRNAs by first detecting segments that contain stable hairpins, then testing them for conservation of the hairpin structures in 37 HCV genotype 1a genomes. Lastly, sequence conservation and position within the precursor's 'arm' was used to locate the 'seed' and the mature microRNA sequence. *(A)* The HCV derived viral small RNAs were analyzed using RT-PCR. The results shown represent a robust increase in vmr11 levels six days post-infection with HCV1a, and only minimal change in vmr20. (I, infected; U, uninfected). As control, miR-122 level is minimally changed upon viral infection. (18S marker serves as internal reference). *(B)* The predicted secondary structure_of vmr11 precursor; mature vmr11 is shown in red.

C

A

B (A)

(B)

SEQUENCE LISTING

<160> NUMBER OF SEQ ID NOS: 53

<210> SEQ ID NO 1
<211> LENGTH: 22
<212> TYPE: RNA
<213> ORGANISM: Hepatitis C virus

<400> SEQUENCE: 1
guucaucauc auaucccaug cc 22

<210> SEQ ID NO 2
<211> LENGTH: 20
<212> TYPE: DNA
<213> ORGANISM: Artificial Sequence
<220> FEATURE:
<223> OTHER INFORMATION: Synthetic H77-QRT Forward Primer

<400> SEQUENCE: 2
tgtggagctg agatcactgg 20

<210> SEQ ID NO 3
<211> LENGTH: 20
<212> TYPE: DNA
<213> ORGANISM: Artificial Sequence
<220> FEATURE:
<223> OTHER INFORMATION: Synthetic H77-QRT Reverse Primer

<400> SEQUENCE: 3
ccgccttatc tccacgtatt 20

<210> SEQ ID NO 4
<211> LENGTH: 11
<212> TYPE: RNA
<213> ORGANISM: Hepatitis C virus

<400> SEQUENCE: 4
ccaucaucaa a 11

<210> SEQ ID NO 5
<211> LENGTH: 14
<212> TYPE: RNA
<213> ORGANISM: Hepatitis C virus

<400> SEQUENCE: 5
ccaucaucuu cuuu 14

<210> SEQ ID NO 6
<211> LENGTH: 40
<212> TYPE: RNA
<213> ORGANISM: Hepatitis C virus

<400> SEQUENCE: 6
caucaucuca uuuaauccuc ccuuccuccc uauuaaccua 40

<210> SEQ ID NO 7
<211> LENGTH: 10
<212> TYPE: RNA
<213> ORGANISM: Hepatitis C virus

<400> SEQUENCE: 7
acaucauccu 10

<210> SEQ ID NO 8
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 8
caucaucauc auaucccaug cc 22

<210> SEQ ID NO 9
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 9
guuguucauc auaucccaug cc 22

<210> SEQ ID NO 10
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 10
guucauguuc auaucccaug cc 22

<210> SEQ ID NO 11
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 11
guucaucaag auaucccaug cc 22

<210> SEQ ID NO 12
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 12
guucaucauc ccaucccaug cc 22

<210> SEQ ID NO 13
<211> LENGTH: 22
<212> TYPE: RNA
<213> ORGANISM: Artificial Sequence
<220> FEATURE:

<223> OTHER INFORMATION: Hepatitis C virus mutant sequence

<400> SEQUENCE: 13
guucaucauc aucccccaug cc 22

<210> SEQ ID NO 14
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 14
guucaucauc auaucccuag cc 22

<210> SEQ ID NO 15
<211> LENGTH: 17
<212> TYPE: RNA
<213> ORGANISM: Artificial Sequence
<220> FEATURE:
<223> OTHER INFORMATION: Hepatitis C virus mutant sequence

<400> SEQUENCE: 15
guucaucauc auauccc 17

<210> SEQ ID NO 16
<211> LENGTH: 14
<212> TYPE: RNA
<213> ORGANISM: Artificial Sequence
<220> FEATURE:
<223> OTHER INFORMATION: Hepatitis C virus mutant sequence

<400> SEQUENCE: 16
guucaucauc auau 14

<210> SEQ ID NO 17
<211> LENGTH: 22
<212> TYPE: RNA
<213> ORGANISM: Artificial Sequence
<220> FEATURE:
<223> OTHER INFORMATION: Hepatitis C virus mutant sequence

<400> SEQUENCE: 17
guucuacuac auaucccaug cc 22

<210> SEQ ID NO 18
<211> LENGTH: 58
<212> TYPE: DNA
<213> ORGANISM: Artificial Sequence
<220> FEATURE:
<223> OTHER INFORMATION: Synthetic TrueSeq Sense Primer

<400> SEQUENCE: 18
aatgatacgg cgaccaccga gatctacact ctttccctac acgacgctct tccgatct 58

<210> SEQ ID NO 19
<211> LENGTH: 64
<212> TYPE: DNA
<213> ORGANISM: Artificial Sequence
<220> FEATURE:
<223> OTHER INFORMATION: Synthetic TruSeq Antisense Primer with NNNNNN
Barcode
<220> FEATURE:
<221> NAME/KEY: misc_feature
<222> LOCATION: (25)..(30)
<223> OTHER INFORMATION: n is a, c, g, or t

<400> SEQUENCE: 19
caagcagaag acggcatacg agatnnnnnn gtgactggag ttcagacgtg tgctcttccg 60
atct 64

<210> SEQ ID NO 20
<211> LENGTH: 22
<212> TYPE: RNA
<213> ORGANISM: Hepatitis C virus

<400> SEQUENCE: 20
cgcccaaauc uccaggcauu ga 22

<210> SEQ ID NO 21
<211> LENGTH: 25
<212> TYPE: RNA
<213> ORGANISM: Hepatitis C virus

<400> SEQUENCE: 21
gacacucaua cuaacgccau ggcua 25

<210> SEQ ID NO 22
<211> LENGTH: 22
<212> TYPE: RNA
<213> ORGANISM: Hepatitis C virus

<400> SEQUENCE: 22
agacaggagc caucccgccc ac 22

<210> SEQ ID NO 23
<211> LENGTH: 22
<212> TYPE: RNA
<213> ORGANISM: Hepatitis C virus

<400> SEQUENCE: 23
cgcccaguuc cccaccaugg ag 22

<210> SEQ ID NO 24
<211> LENGTH: 22
<212> TYPE: RNA
<213> ORGANISM: Hepatitis C virus

<400> SEQUENCE: 24
ggccagccca caaggucuug gu 22

<210> SEQ ID NO 25
<211> LENGTH: 22
<212> TYPE: RNA
<213> ORGANISM: Hepatitis C virus

<400> SEQUENCE: 25
acaugcaugu caugauguau uu 22

<210> SEQ ID NO 26
<211> LENGTH: 22
<212> TYPE: RNA
<213> ORGANISM: Hepatitis C virus

<400> SEQUENCE: 26
guucaucauc auaucccaug cc 22

<210> SEQ ID NO 27
<211> LENGTH: 22

-continued

<212> TYPE: RNA
<213> ORGANISM: Hepatitis C virus

<400> SEQUENCE: 27
ggagcuggcc auagaagggg gu 22

<210> SEQ ID NO 28
<211> LENGTH: 22
<212> TYPE: RNA
<213> ORGANISM: Hepatitis C virus

<400> SEQUENCE: 28
guacacaaua cucgaguuag gg 22

<210> SEQ ID NO 29
<211> LENGTH: 22
<212> TYPE: RNA
<213> ORGANISM: Hepatitis C virus

<400> SEQUENCE: 29
cuugccguag guggaguacg ug 22

<210> SEQ ID NO 30
<211> LENGTH: 22
<212> TYPE: RNA
<213> ORGANISM: Hepatitis C virus

<400> SEQUENCE: 30
ucgagguugc gaccgcucgg aa 22

<210> SEQ ID NO 31
<211> LENGTH: 22
<212> TYPE: RNA
<213> ORGANISM: Hepatitis C virus

<400> SEQUENCE: 31
ugacccgucg cugagauccg ga 22

<210> SEQ ID NO 32
<211> LENGTH: 22
<212> TYPE: RNA
<213> ORGANISM: Hepatitis C virus

<400> SEQUENCE: 32 gggggggcg gaguaccugg uc 22

<210> SEQ ID NO 33
<211> LENGTH: 22
<212> TYPE: DNA
<213> ORGANISM: Hepatitis C virus

<400> SEQUENCE: 33
cgcccaaatc tccaggcatt ga 22

<210> SEQ ID NO 34
<211> LENGTH: 25
<212> TYPE: DNA
<213> ORGANISM: Hepatitis C virus

<400> SEQUENCE: 34
gacactcata ctaacgccat ggcta 25

<210> SEQ ID NO 35

<211> LENGTH: 22
<212> TYPE: DNA
<213> ORGANISM: Hepatitis C virus

<400> SEQUENCE: 35
agacaggagc catcccgccc ac 22

<210> SEQ ID NO 36
<211> LENGTH: 22
<212> TYPE: DNA
<213> ORGANISM: Hepatitis C virus

<400> SEQUENCE: 36
cgcccagttc cccaccatgg ag 22

<210> SEQ ID NO 37
<211> LENGTH: 22
<212> TYPE: DNA
<213> ORGANISM: Hepatitis C virus

<400> SEQUENCE: 37
ggccagccca caaggtcttg gt 22

<210> SEQ ID NO 38
<211> LENGTH: 22
<212> TYPE: DNA
<213> ORGANISM: Hepatitis C virus

<400> SEQUENCE: 38
acatgcatgt catgatgtat tt 22

<210> SEQ ID NO 39
<211> LENGTH: 22
<212> TYPE: DNA
<213> ORGANISM: Hepatitis C virus

<400> SEQUENCE: 39
gttcatcatc atatcccatg cc 22

<210> SEQ ID NO 40
<211> LENGTH: 22
<212> TYPE: DNA
<213> ORGANISM: Hepatitis C virus

<400> SEQUENCE: 40
ggagctggcc atagaagggg gt 22

<210> SEQ ID NO 41
<211> LENGTH: 22
<212> TYPE: DNA
<213> ORGANISM: Hepatitis C virus

<400> SEQUENCE: 41
gtacacaata ctcgagttag gg 22

<210> SEQ ID NO 42
<211> LENGTH: 22
<212> TYPE: DNA
<213> ORGANISM: Hepatitis C virus

<400> SEQUENCE: 42
cttgccgtag gtggagtacg tg 22

-continued

<210> SEQ ID NO 43
<211> LENGTH: 22
<212> TYPE: DNA
<213> ORGANISM: Hepatitis C virus

<400> SEQUENCE: 43
tcgaggttgc gaccgctcgg aa 22

<210> SEQ ID NO 44
<211> LENGTH: 22
<212> TYPE: DNA
<213> ORGANISM: Hepatitis C virus

<400> SEQUENCE: 44
tgacccgtcg ctgagatccg ga 22

<210> SEQ ID NO 45
<211> LENGTH: 22
<212> TYPE: DNA
<213> ORGANISM: Hepatitis C virus

<400> SEQUENCE: 45 gggggggcg gagtacctgg tc 22

<210> SEQ ID NO 46
<211> LENGTH: 33
<212> TYPE: RNA
<213> ORGANISM: Hepatitis C virus

<400> SEQUENCE: 46
aguucaucau cauaucccau gccaugcgau gac 33

<210> SEQ ID NO 47
<211> LENGTH: 29
<212> TYPE: RNA
<213> ORGANISM: Hepatitis C virus

<400> SEQUENCE: 47
cccguuauau ggccgggaua gauagaaca 29

<210> SEQ ID NO 48
<211> LENGTH: 18
<212> TYPE: DNA
<213> ORGANISM: Hepatitis C virus

<400> SEQUENCE: 48
acgatctacg acggatca 18

<210> SEQ ID NO 49
<211> LENGTH: 18
<212> TYPE: DNA
<213> ORGANISM: Hepatitis C virus

<400> SEQUENCE: 49
acgatctacg acgggtca 18

<210> SEQ ID NO 50
<211> LENGTH: 18
<212> TYPE: DNA
<213> ORGANISM: Hepatitis C virus

<400> SEQUENCE: 50
tcgatctact acggatca 18

-continued

```
<210> SEQ ID NO 51
<211> LENGTH: 18
<212> TYPE: DNA
<213> ORGANISM: Hepatitis C virus

<400> SEQUENCE: 51

acgagcttcg acggctca                                                18


<210> SEQ ID NO 52
<211> LENGTH: 24
<212> TYPE: RNA
<213> ORGANISM: Hepatitis C virus

<400> SEQUENCE: 52

ggcgggggga ggaggauggu gacc                                         24


<210> SEQ ID NO 53
<211> LENGTH: 21
<212> TYPE: RNA
<213> ORGANISM: Hepatitis C virus

<400> SEQUENCE: 53

guucaucuac uaucccaugc c                                            21
```

BLOCKING HEPATITIS C VIRUS INFECTION ASSOCIATED LIVER TUMOR DEVELOPMENT WITH HCV-SPECIFIC ANTISENSE RNA

CROSS REFERENCE TO RELATED APPLICATIONS

The present application is a U.S. National Stage Application under 35 U.S.C. § 371 of International Application No. PCT/US15/22423, filed Mar. 25, 2015, which claims the benefit of priority to U.S. Provisional Application No. 61/970,022, filed on Mar. 25, 2014, and U.S. Provisional Application No. 62/076,500, filed on Nov. 7, 2014, the entire contents of each of which are hereby incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GWUV_004_01WO_SubSeqList_ST25, date recorded: Sep. 26, 2016, file size 9 kilobytes).

FIELD OF THE DISCLOSURE

The present disclosure relates to methods for blocking Hepatitis C Virus (HCV) infection associated liver tumor development with antagonists of a virus derived microRNA. In particular aspects, the disclosure provides for single stranded oligonucleotide antagonists of virus derived microRNA. Particular embodiments of the disclosure teach single stranded antisense oligonucleotides that are antagonists against HCV derived vmr11.

BACKGROUND OF THE DISCLOSURE

Hepatitis C Virus (HCV) infection is a major risk factor for chronic hepatitis and hepatocellular carcinoma (HCC), the most common type of liver cancer. It is estimated that 130-150 million people globally have chronic hepatitis C infection. A significant number of those who are chronically infected will develop liver cirrhosis or liver cancer.

However, the mechanism of HCV-mediated hepatocarcinogenesis is not well understood. There have been unsuccessful attempts to elucidate the exact mechanisms associated with HCV-mediated hepatocarcinogenesis, but these endeavors have been met with ambiguity. At present, there is a dearth of empirical evidence that researchers can use to effectively understand how HCV infection causes hepatocellular carcinogenesis. Consequently, there has been little progress on developing effective treatments for this disease.

Thus, there is an urgent need in the medical community to understand the mechanisms associated with HCV infection mediated hepatocarcinogenesis. A proper understanding of the mechanisms underlying HCV associated liver cancer will enable doctors and researchers to develop therapies to combat this serious disease.

SUMMARY OF THE INVENTION

The present disclosure addresses an urgent need in the medical community, by elucidating the cellular mechanisms underlying HCV-mediated hepatocarcinogenesis.

Furthermore, the disclosure utilizes this mechanistic understanding to develop effective treatments that target the underlying molecular machinery responsible for HCV-mediated hepatocellular carcinogenesis.

For instance, in an embodiment, the disclosure teaches methods useful for protecting against HCV-mediated hepatocarcinogenesis through the administration of an antagonist of a virus-derived microRNA. In some aspects, the virus-derived microRNA is vmr11.

In an embodiment, the disclosure teaches methods of administering an antagonist of a virus-derived mircroRNA, wherein said virus-derived mircroRNA prevents the transportation of PTEN to a cell nucleus.

In some aspects, the disclosure teaches methods of administering an antagonist of a virus-derived mircroRNA, wherein said virus-derived mircroRNA targets Transportin-2.

In still other aspects, the disclosure teaches antagonists that mimic, or contain, the target binding region from Transportin-2 that is bound by a virus-derived microRNA.

In some embodiments, a method of preventing HCV infection associated hepatocellular carcinoma in a patient comprises: the administration to a patient in need thereof an antagonist of a virus derived microRNA, such as vmr11; wherein vmr11 comprises a nucleic acid sequence sharing at least 80% sequence identity to 5'-GUUCAUCAUCAUAUCCCAUGCC-3' (SEQ ID NO:1). In some embodiments, the nucleotides at positions 4 through 10 in a 5' to 3' directionality are CAUCAUC.

In some embodiments, the patient experiences a decline in DNA double stranded breaks in cells infected with HCV after administration of the antagonist of vmr11.

In some embodiments, the vmr11 comprises a nucleotide sequence sharing at least 85%, 90%, 95%, 96%, 97%, 98%, or 99% sequence identity to 5'-GUUCAUCAUCAUAUCCCAUGCC-3'(SEQ ID NO: 1).

In further embodiments, the vmr11 comprises a nucleotide sequence of 5'-GUUCAUCAUCAUAUCCCAUGCC-3'(SEQ ID NO: 1).

In some embodiments the antagonist of vmr11 is a single stranded oligonucleotide that comprises the sequence 5'-CUACUAC-3'.

In some embodiments, the antagonist of vmr11 is a 19 to 25 nucleotide long single stranded oligonucleotide that comprises the sequence 5'-CUACUAC-3'. In further embodiments, the antagonist of vmr11 is a 22 nucleotide long single stranded oligonucleotide that comprises 5'-CUACUAC-3'.

In some embodiments, the antagonist of vmr11 is a 22 nucleotide long single stranded oligonucleotide that comprises the sequence 5'-CUACUAC-3' at nucleotide positions 4-10.

In some embodiments, the antagonist of vmr11 is a 22 nucleotide long single stranded oligonucleotide that comprises the sequence 5'-CUACUAC-3' at positions 4-10, and the antagonist of vmr111 forms a parallel duplex structure (RNApds) with vmr11 at nucleotide positions 4-10.

In some embodiments, the vmr11 nucleotides at positions 4 to 10, in a 5' to 3' direction, are CAUCAUC, which forms a parallel duplex structure with a target mRNA comprising a CAUCAUC nucleotide sequence, and the parallel duplex structure interferes with the translation and/or stability of the target mRNA.

In some embodiments, the vmr11 binds at least one mRNA encoding a protein selected from the group consisting of: PTEN, HNF4α, and Transportin-2. In further embodiments, the vmr11 binds Transportin-2 gene and inhibits the translocation of PTEN to a cell nucleus. Thus, aspects of the disclosure teach antagonists of vmr11, which contain nucleotide binding sequences that are substantially similar to the nucleotide binding sequence targets of vmr111 contained on PTEN, HNF4α, and Transportin-2 genes.

In some embodiments, the antagonist of vmr11 is an antagomir.

In further embodiments, the antagomir is an antisense oligonucleotide comprising a single stranded nucleotide sequence that is complementary to vmr11 and contains no more than 5 mismatched base pairs across the length of complementarity.

In further embodiments, the antagomir is an antisense oligonucleotide comprising a single stranded nucleic acid sequence that is at least 80% complementary to vmr11. In further embodiments, the antagomir is an antisense oligonucleotide comprising a single stranded nucleic acid sequence that is at least 85%, 90%, 95%, 96%, 97%, 98%, or 99% complementary to vmr111.

In further embodiments, the antagomir is an antisense oligonucleotide comprising a single stranded nucleic acid sequence that is fully complementary to vmr11.

In some embodiments, the antagomir is an antisense oligonucleotide comprising a single stranded nucleic acid sequence that is fully complementary to vmr11 and the antisense oligonucleotide forms a duplex with vmr11 under normal human physiological conditions.

In some embodiments, the antagomir is an antisense oligonucleotide comprising a single stranded nucleic acid sequence comprising 5'-GAUGAUG-3'. In further embodiments, the antagomir is a 19 to 25 nucleotide long antisense oligonucleotide comprising a single stranded nucleic acid sequence comprising 5'-GAUGAUG-3' at nucleotide positions 4 to 10. In further embodiments, the antagomir is a 22 nucleotide long antisense oligonucleotide sequence comprising a single stranded nucleic acid sequence comprising 5'-GAUGAUG-3'. In further embodiments, the antagomir is a 22 nucleotide long antisense oligonucleotide sequence comprising a single stranded nucleic acid sequence comprising 5'-GAUGAUG-3' at nucleotide positions 4-10.

In some embodiments, the antagonist of vmr111 oligonucleotide sequence comprises one or more nucleotide modifications that increase stability of the oligonucleotide in the presence of a nuclease. In further embodiments, one or more of the nucleotide units of the oligonucleotide are locked nucleic acid (LNA) units. In further embodiments, one or more of the nucleotide units of the oligonucleotide are 2' substituted nucleotide analogues. In further embodiments, the 2' substituted nucleotide analogues are selected from the group consisting of: 2'-deoxy, 2'deoxy-2'fluoro, 2'-fluoro, 2'-O-methyl, 2'-O-methoxyethyl (2'-O-MOE), 2-O-aminopropyl (2'-O-AP), 2'-O-dimethylaminoethyl (2'-O-DMAOE), 2'-O-dimethylaminopropyl (2'-O-DMAP), 2'-O-dimethylamioethyloxyethyl (2'-O-DMAEOE), 2'O—N-methylacetamido (2'-O-NMA), and combinations thereof.

In further embodiments, one or more of the nucleotide units of the oligonucleotide contain a 2'-fluoro substitution of the 2'-OH of the 2'-deoxyribose.

In some embodiments, one or more of the internucleoside linkages between the nucleotide units of the oligonucleotide are phosphorothioate internucleoside linkages.

In some embodiments, one or more nucleotides of the 5' and/or 3' terminal ends of the oligonucleotide contain modifications.

DETAILED DESCRIPTION OF THE INVENTION

Figure 1:
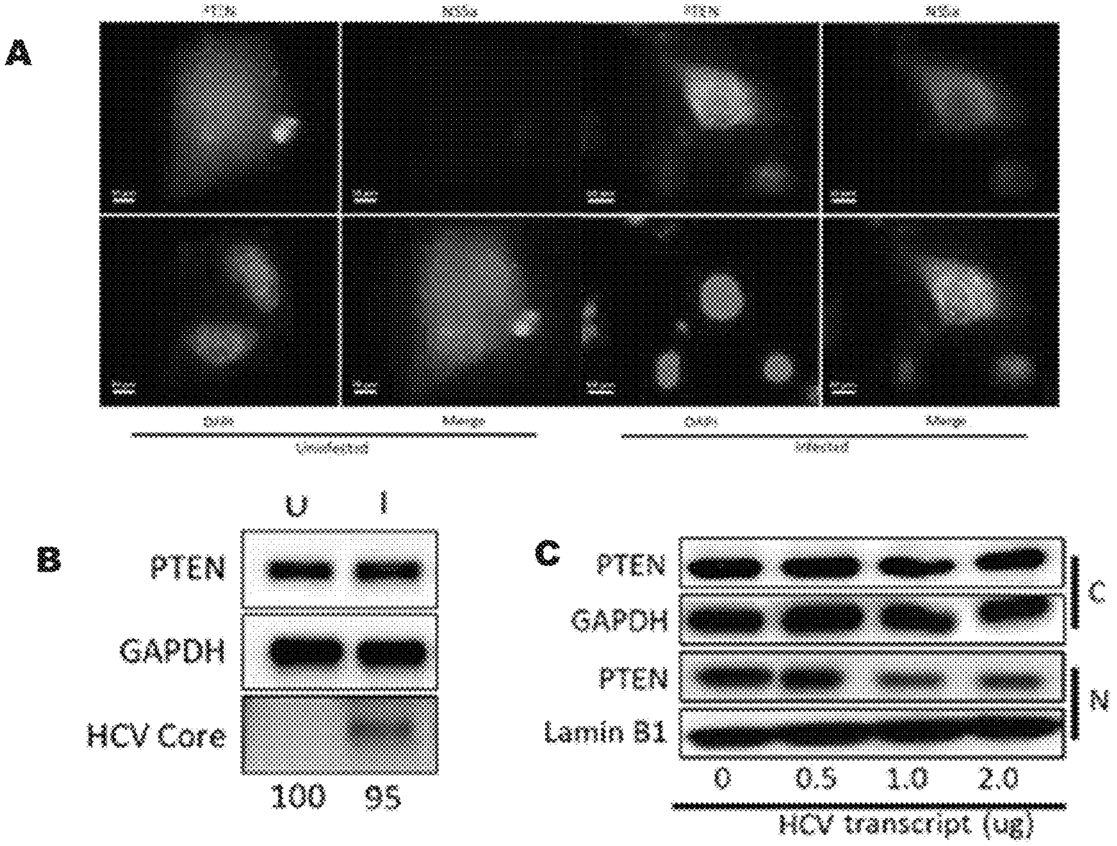
FIG. 1: (A) Primary hepatocyte cultures (PPH cells) were transfected with 1 μg HCV1a genomic RNA (using FuGENE Invitrogen protocol). Cells were visualized at day 3 post-transfection. The uninfected cells (left four panels) show uniform PTEN staining; HCV replication is marked with NS5A antigen (far right panel). Transfection efficiency of HCV genomic RNA was approximately 30%. (B) In order to visualize PTEN protein in HCV-infected cells $1\times10^5$ PPH cells were transfected with 1 μg H77 HCV1a genomic RNA, and the cells were collected at day five (U, uninfected; I, infected). Total cell protein was extracted using RIPA buffer; 20 μg of protein was analyzed on 10% precast MiniProtein Gel; numbers underneath each lane indicate the relative values of PTEN. HCV replication is marked with viral core antigen (HCV Core). (C) Restriction of nuclear PTEN protein in HCV-infected cells was visualized by transfecting $1\times10^5$ PPH cells with increasing amounts (0.5, 1.0, 2.0 g) of input HCV1a genomic RNA, cells were harvested 5 days post-transfection and 10 μg each of nuclear or cytoplasmic protein were analyzed by Western blot. GAPDH and Lamin B1 were loading controls respectively, for the cytoplasmic or nuclear protein.

About 70% of all HCV infected people establish chronic infection. Current antiviral therapy against HCV consists of interferon in combination with ribavirin, which is effective in some patients; however, a large group does not respond, or does not tolerate, the treatment. Therefore, a need for novel treatment modalities for HCV exists. The present invention provides a novel treatment for HCV patients that are not responding to treatment by interferon, particularly as a preventative for HCV-mediated hepatocarcinogenesis.

The present disclosure is based, in one aspect, on administering one or more antagonists of a virus derived miRNA, e.g., vmr11.

Antagonists

Antagonists may be small-molecule antagonists, protein antagonists, pharmaceutical antagonists, synthetically derived antagonists, polynucleotide antagonists, and oligonucleotide antagonists.

The present disclosure is based in part on the fact that the expression of endogenous microRNAs (miRNAs) or pre-microRNAs (pre-miRNAs) can be inhibited by an antagonist to such.

For example, the disclosure teaches systemic or local administration of the taught antagonists. Administration of the taught antagonists can be via any method known in the art, such as: parenteral administration or nonparenteral administration, e.g. oral administration. The preferred mode of administration is left to the discretion of the practitioner.

The disclosure provides specific methods that are useful in reducing miRNA and pre-miRNA levels, in e.g., a mammal, such as a human. In particular, the present disclosure provides specific methods that are useful for reducing levels of viral miRNAs of hepatitis C virus.

Antisense Oligonucleotide Antagonists

In some aspects, an antisense oligonucleotide is utilized that binds to the miRNA. In a particular aspect, the disclosure provides for antisense RNA antagonists that bind to miRNAs.

In one aspect, the disclosure features antisense oligonucleotides targeting viral derived miRNA. These antisense oligonucleotides can be HCV-specific and target miRNA derived from HCV.

The antisense oligonucleotides may be ribonucleotides or deoxyribonucleotides. In aspects, the antisense oligonucleotides have at least one chemical modification. For instance, suitable antisense oligonucleotides may be comprised of one or more "conformationally constrained" or bicyclic sugar nucleoside modifications, for example, "locked nucleic acids." "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs.

The antisense oligonucleotides targeting HCV derived miRNA can contain combinations of LNAs or other modified nucleotides and ribonucleotides or deoxyribonucleotides. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages In aspects, the antisense oligonucleotides useful for inhibiting the activity of miRNAs are about 5 to about 50 nucleotides in length, about 10 to about 30 nucleotides in length, or about 20 to about 25 nucleotides in length.

Antisense oligonucleotides may in some cases comprise a sequence that is at least partially complementary to a mature miRNA sequence, e.g. at least about 75%, 80%, 85%, 90%, 95%, 96%, 97%, 98%, or 99% complementary to a mature miRNA sequence.

In some embodiments, the antisense oligonucleotide may be substantially complementary to a mature miRNA sequence.

In an embodiment, the antisense oligonucleotide comprises a sequence that is 100% complementary to a mature miRNA sequence. In some embodiments, the mature miRNA sequence corresponds to vmr11

Complementarity may be based upon classical Watson and Crick basepairing, or may be based upon Hoogsteen or reverse Hoogsteen basepairing.

Antagomir Antagonists

In embodiments, the disclosure teaches antisense oligonucleotides that are antagomirs. These antagomirs can be oligonucleotides used to silence microRNA.

The disclosure provides for the administration of antagomirs against viral derived miRNA. The viral derived miRNA may be from HCV.

An antagomir is a single-stranded—often chemically-modified—oligonucleotide, which is at least partially complementary to the miRNA sequence. Antagomirs may comprise one or more modified nucleotides, such as 2'-O-methyl-sugar modification. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a steroid such as cholesterol, a fatty acid, a vitamin, a carbohydrate, a peptide or another small molecule ligand at its 3' end.

Antagomirs suitable for inhibiting miRNAs may be about 15 to about 50 nucleotides in length, or about 18 to about 30 nucleotides in length, or about 20 to about 25 nucleotides in length.

Anatgomirs may in some cases comprise a sequence that is at least partially complementary to a mature miRNA sequence, e.g. at least about 75%, 80%, 85%, 90%, 95%, 96%, 97%, 98%, or 99% complementary to a mature miRNA sequence.

In some embodiments, the antagomir may be substantially complementary to a mature miRNA sequence.

In other embodiments, the antagomirs are 100% complementary to the mature miRNA sequence. In some aspects, the mature miRNA is vmr11.

In some embodiments, the antagomirs comprise a sequence that is perfectly complementary to a mature HCV derived miRNA.

In aspects, an antagomir featured in the disclosure includes a nucleotide sequence sufficiently complementary to hybridize to a miRNA target sequence of about 12 to 25 nucleotides, about 15 to 23 nucleotides, 19 to 25 nucleotides, 15 to 25 nucleotides, or 22 to 25 nucleotides in length. In some aspects, the target sequence may differ by no more than 1, 2, 3, 4, 5, 6, 7, 8, 9, or 10 nucleotides from an antagomir sequence Complementarity may be based upon classical Watson and Crick basepairing, or may be based upon Hoogsteen or reverse Hoogsteen basepairing.

Antagomirs can be stabilized against nucleolytic degradation, by the incorporation of a modification, e.g., a nucleotide modification. In another embodiment, the antagomir includes a phosphorothioate at least the first, second, or third internucleotide linkage at the 5' or 3' end of the nucleotide sequence. In yet another embodiment, the antagomir includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In an aspect, the antagomir may include at least one 2'-O-methyl-modified nucleotide, and in some embodiments, all of the nucleotides of the antagomir include a 2'-O-methyl modification.

In one embodiment, the antagomir includes a non-nucleotide moiety, e.g., a cholesterol moiety. The non-nucleotide moiety can be attached, e.g., to the 3' or 5' end of the oligonucleotide agent. In one aspect, a cholesterol moiety is attached to the 3' end of the oligonucleotide agent.

The binding affinity and specificity to a target, efficiency of cellular uptake, and nuclease resistance are all factors in the delivery and activity of an oligonucleotide-based therapeutic, such as an antagomir. For example, when oligonucleotides are introduced into intact cells they are attacked and degraded by nucleases leading to a loss of activity. Thus, a useful oligonucleotide should have good resistance to extra- and intracellular nucleases, as well as be able to penetrate the cell membrane.

Consequently, in one aspect, the antagomir is further modified so as to be attached to a ligand that is selected to improve stability, distribution, or cellular uptake of the agent, e.g., cholesterol. The oligonucleotide antagomir can further be in isolated form or can be part of a pharmaceutical composition used for the methods described herein, particularly as a pharmaceutical composition formulated for parental administration.

In some aspects, antagomirs may be designed for greater structural stability or thermostability to maintain the integrity of the antagomir sequence under stressors such as exposure to varying salt concentrations, pH environments, temperature changes, and the presence of nucleases.

Compositions Comprising the Antagonists

The disclosure further provides pharmaceutical compositions comprising the antagonists taught herein. For example, compositions comprising the antisense oligonucleotide antagonists or the antagomir antagonist.

Expression Vector Delivery of the Antagonists

In embodiments the antisense oligonucleotide antagonists described herein can be delivered to the target cell (e.g. liver cell) by delivering to the cell an expression vector encoding the antisense antagonist. For example, one may deliver to a liver cell an expression vector encoding an antisense oligonucleotide that targets vmr11.

A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically.

For purposes of this application, the terms "expression construct," "expression vector," and "vector," are used interchangeably to demonstrate the application of the disclosure in a general, illustrative sense.

In one embodiment, an expression vector for expressing an antisense oligonucleotide antagonist against vmr11, comprises a promoter operably linked to a polynucleotide encoding said antisense oligonucleotide against vmr11, wherein the sequence of the expressed antisense oligonucleotide is partially or perfectly complementary to a mature vmr11.

EXAMPLES

Example 1: Loss of Nuclear PTEN in HCV-Infected Human Hepatocytes

Phosphatase and tensin homologue deleted on chromosome 10 (PTEN) is one of the most commonly targeted tumor suppressor genes in human cancers, encoding a 403-residues dual specificity phosphatase with both lipid and protein phosphatase activities [1-5]. The lipid phosphatase activity of PTEN is a central negative regulator of the phosphatidylinositol-3-kinase (PI3K) signal cascade for cell growth and proliferation. Deregulation of PTEN has been associated with a spectrum of metabolic disorders related to hepatocarcinogenesis [6]. A recent report [7] points to post-transcriptional silencing of PTEN by HCV core 3a protein as a possible mechanism of PTEN deregulation.

Nuclear insufficiency of PTEN has been shown to contribute to centromere destabilization and genomic instability [8,9], a hallmark of cancer, and nuclear PTEN depletion has been associated with more aggressive cancers [10-12]. In this study, we ask whether HCV infection initiates nuclear PTEN insufficiency and, in particular, whether viral noncoding RNA plays a part in regulating the intracellular redistribution of PTEN protein. We present evidence of inhibition of Transportin-2 by a viral noncoding RNA (vmr11). This inhibition restricts nuclear translocation of PTEN in HCV-infected human hepatocytes. We further show that restoring intracellular Transportin-2 levels rescues wild-type levels of nuclear PTEN. Based on the interaction between PTEN and transportin 2, our results support a novel mechanism of regulation of nuclear PTEN translocation where down-regulation of Transportin-2 by vmr11 correlates with the nuclear exclusion of PTEN protein in HCV-infected human hepatocytes.

Restriction of Nuclear PTEN in HCV-Infected Cells

We examined the distribution of PTEN by immunofluorescence staining in human primary hepatocytes, before and after transfection with HCV1a genomic RNA [13]. FIG. 1A (upper panels) shows a uniform distribution of PTEN in uninfected cells, whereas staining of nuclear PTEN was less uniformly distributed in HCV replicating cells. Virus replication in this assay was marked with immune staining for NS5A antigen (far right panel).

To quantitatively analyze the intracellular distribution of PTEN protein, we performed Western blots of total cell protein, and of the nuclear and cytoplasmic fractions of HCV-infected cells (FIGS. 1B and 1C). There was no noticeable change in PTEN protein levels when we compared total cell proteins of HCV-replicating and control cells (FIG. 1B; virus replication was marked by immunoblot for HCV core antigen). However, when we compared PTEN protein levels in the nuclear and the cytoplasmic fractions (FIG. 1C), we observed marked inhibition of nuclear PTEN in HCV-replicating cells. These results suggest a progressive decline of nuclear PTEN in cells transfected with increasing amounts of viral genomic RNA (FIG. 1C). The relatively unchanged levels of cytoplasmic PTEN and gradual decline in nuclear PTEN suggest, but do not prove, the deregulation of intracellular distribution of PTEN as possible mechanism of nuclear PTEN depletion in HCV-replicating cells. We therefore asked whether viral small noncoding RNAs might, directly or indirectly, modulate the intracellular distribution of the PTEN protein.

HCV-Derived Small Non-Coding RNAs

Figure 2:
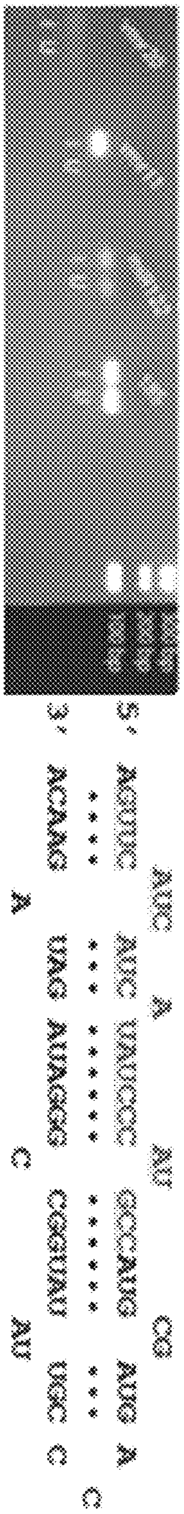
FIG. 2: (A) Quantitation of vmrs: RT-PCR results show robust increase in vmr1 levels six days post-transfection with HCV genomics RNA, and only minimal change in mvr20. (I=infected; U=uninfected). As control, miR-122 level is minimally changed upon viral infection. (18S marker served as internal reference). (B) Structure of vmr11 RNA: Predicted secondary structure of vmr11 precursor. Residues 2-23 of SEQ ID NO:47 are mature vmr11 RNA. The top sequence is SEQ ID NO:46, and the bottom sequence is SEQ ID NO:47.
Figure 22:
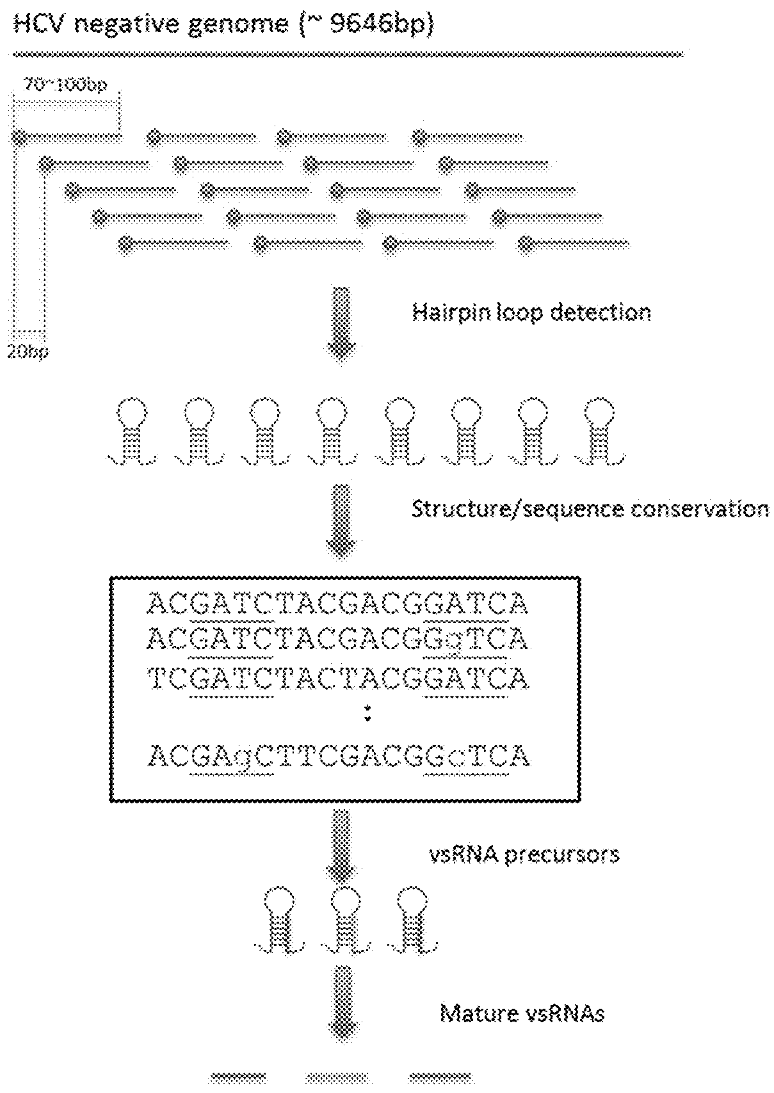
FIG. 22: Schematic representation of the bioinformatics approach for predicting conserved structural domains of HCV1a genomic RNA, precursors of viral small non-coding RNAs, and the mature vmr sequences. Fixed-size (70, 80, 90, and 100 bp) segments of the negative strand of the HCV1a reference genome (NC_004102) were evaluated for their potential to encode viral microRNAs by first detecting segments that contain stable hairpins, then testing them for conservation of the hairpin structures in 37 HCV genotype 1a genomes. Lastly, sequence conservation and position within the precursor's 'arm' was used to locate the 'seed' and the mature microRNA sequence. The schematic comprises four nucleotide sequences in descending order spanning SEQ ID NO:48-51

The positive sense HCV RNA genome is replicated in infected cells using the minus strand viral genomic RNA as a template. We reasoned that the conserved hairpin loop structure of the minus strand genomic RNA, which is not engaged in translation, could serve as possible source of viral small non-coding RNAs (vmrs). To determine candidate vmrs, we employed bioinformatics methods to search the ~9,600 bp minus strand RNA genome for structurally conserved hairpins that could act as putative viral microRNA precursors. Sequence conservation at the 'seed' position in 37 GenBank HCV genomes as well as the configuration geometry of the hairpin arm and loop helped select 13 candidates, whose presence in HCV infected cells were validated with qRT-PCR (FIG. 22 and Table 8, for details). Here we discuss the functional validation of the 22 nt vmr11 RNA that was abundantly expressed in HCV infected human hepatocytes (FIG. 2).

Abundance of Vmr11 Varies with Time Post HCV Infection

Figure 3:
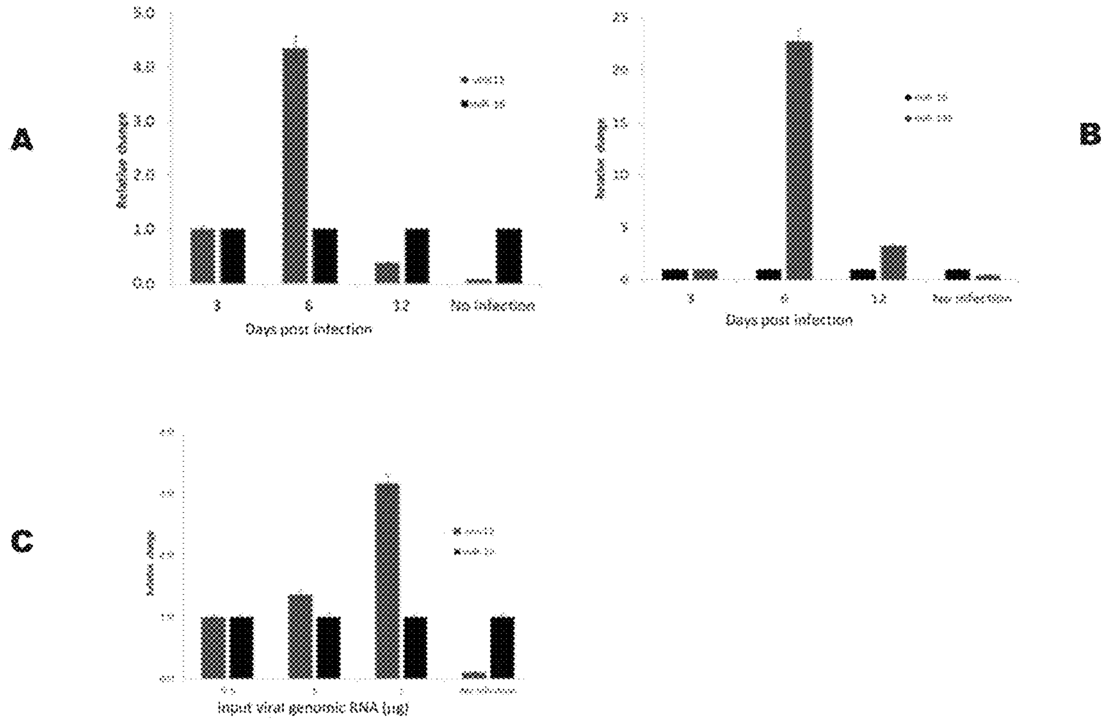
FIG. 3: (A) vmr11 RNA expression. $1\times10^5$ PPH cells were transfected with 1 μg of HCV1a genomic RNA and harvested on days 3, 6 and 12 post-transfection; vmr11 was monitored by qRT-PCR (normalized to miR-16, which does not change with viral infection). (B) MicroRNA-141 expression with increasing input viral genomic RNA: qRT-PCR analysis of miR-141 in PPH cells transfected with increasing amounts of viral genomic RNA. (C) Increase in vmr111 expression with increasing HCV genomic RNA: qRT-PCR of vmr11 RNA in PPH cells transfected with increasing amounts of input viral genomic RNA (0.5, 1 and 2 μg) was analyzed five days post-transfection.

We reasoned that the HCV-derived vmr11 would be expected to accumulate with increasing duration of virus replication and increased input of viral genomic RNA. To test the prediction, we performed qRT-PCR analyses of vmr11 RNA in human hepatocytes (transfected with HCV genomic RNA) at 3, 6 and 12 days post-transfection (FIG. 3A, B) and repeated the analyses in cells transfected with increasing amounts of HCV genomic RNA (FIG. 3C). We observed the highest accumulation of vmr11 at day six post-transfection of human hepatocytes (FIG. 3A). As reported earlier [13] HCV replication can be maintained for weeks with serial passages through naive hepatocyte cultures. However, viral RNA replication in continuous cultures declines after a peak at six days, as does the HCV genomic RNA derived vmr11 (FIG. 3A). The accumulation of vmr11 RNA also correlated with increasing amounts of viral genomic RNA transfected into human hepatocytes (FIG. 3C). Serving as a control, we observed a parallel increase in host cell miRNA-141 (FIG. 3B). It was previously reported that HCV replication correlates with miR-141-mediated post-transcriptional silencing of the DLC-1 tumor suppressor [14]. Conversely, expression of miR-16, which is not sensitive to HCV replication, remained unchanged in HCV-infected cells. While the mechanism behind the processing of the 22 nt vmr11 sequence is not completely understood, the increased production of vmr11 in parallel with viral replication indicates that vmr11 is derived from the HCV genomic RNA.

Expression Arrays of Human Hepatocytes Transfected with Vmr11 "Mimic" Oligonucleotides as Compared to HCV-Infected Cells.

To identify vmr111 target genes that may be involved in limiting nuclear PTEN translocation, we contrasted changes in gene expression in HCV-infected hepatocytes (shown as H77-1, -2 and -3 in three independent infections), and separately in cells transfected with vmr11 "mimic" oligonucleotides (mimic-1, -2 and -3), against uninfected (control) cells, using the Agilent microarray platform (Additional file 2). For each comparison, differential expression analyses revealed several hundred up- and down-regulated genes that could serve as potential markers for HCV infection-associated liver disease. Notably, the qualitative and quantitative changes in gene expression of cells transfected with vmr11 "mimic" oligonucleotides (vmr11 'mimic' is defined as a synthetic 22 nt oligomer identical in sequence with the 'wild type' vmr11) were similar to those in HCV-infected cells (Additional file 1: Figure S2). Functional analyses using the KEGG database [15] revealed several pathways enriched among differentially expressed genes and in common between the two sets of comparisons (H77 and 'mimic'). In particular, genes involved in lipid biosynthesis, intracellular signaling, and control of cell growth and patterning were enriched among the up-regulated genes; whereas genes involved in the regulation of cell motility, and members of the peroxisome proliferator activated receptors (PPAR) signaling pathway involved in lipid metabolism, were over-represented among the down-regulated genes (Additional file 3).

Import of Nuclear PTEN Sensitive to Intracellular Transportin-2 Levels

Figure 4:
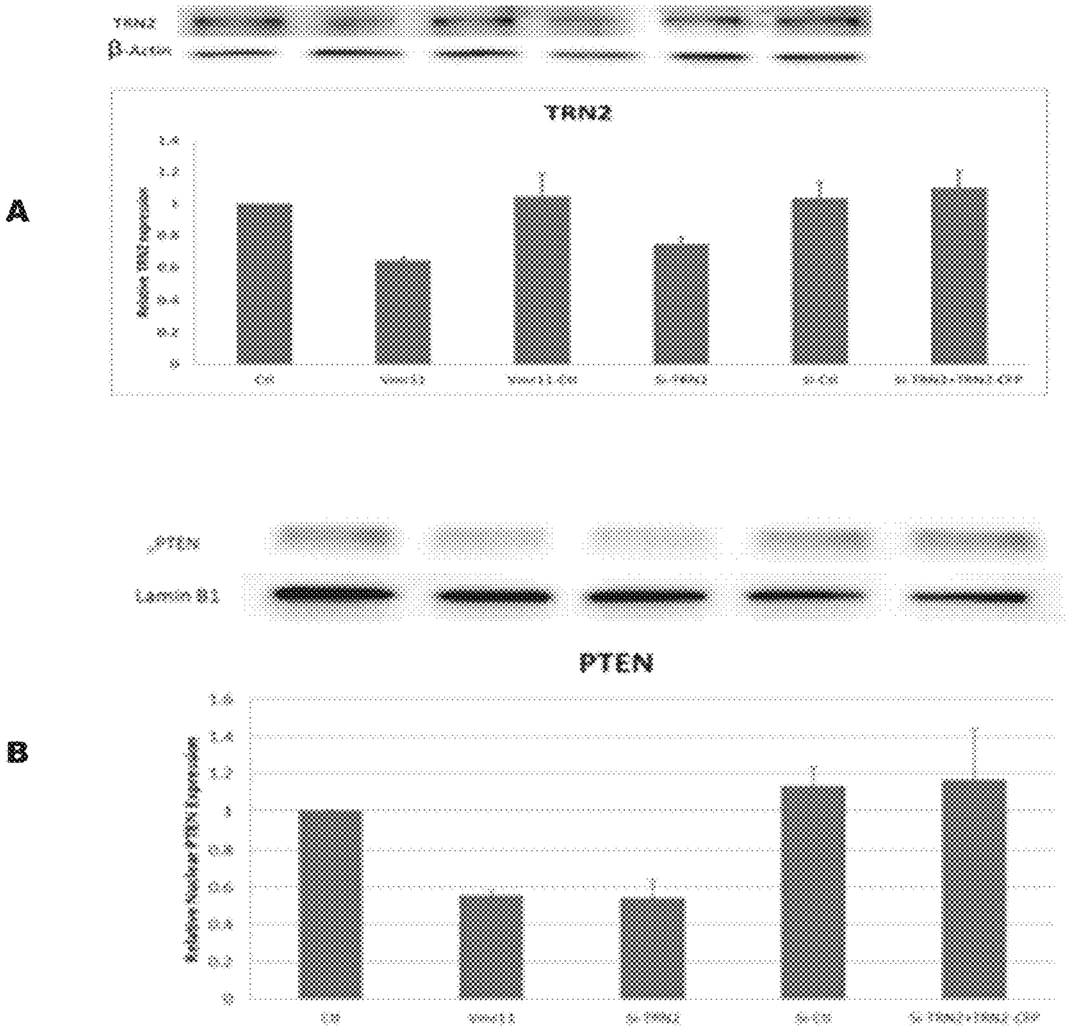
FIG. 4: vmr111-suppression of Transportin-2 restricts nuclear PTEN: (A) Transportin-2 protein is inhibited by vmr111: Uninfected PPH cultures were transfected with 50 μM oligonucleotides (from left to right): scrambled vmr11 (Ctl), vmr11 mimic (vmr11), vmr11 plus vmr11-antagomir (vmr11-Ctl), TRN-2 siRNA (Si-TRN-2), scrambled siTRN-2 (Si-Ctl) and siTRN-2 plus TRN-2 cDNA expression vector (Si-TRN-2+TRN2-CFP). Western blots of TRN-2 protein from cells harvested 48 hours post-transfection were quantitated from three independent assays using β-Actin as loading control. (B) Nuclear PTEN is restricted by vmr11 or siTRN-2 knock-down: PPH cultures were transfected with 50 μM oligonucleotides (from left to right): scrambled vmr11 (ctrl), vmr11 "mimic" (vmr11), si-TRN2, scrambled si-TRN2 (si-ctl) or 1 μg TRN-2 cDNA expression vector following TRN-2 knock-down (si-TRN2+TRN2-CFP). Transfections were repeated twice at 24 hour intervals and cells were harvested at 48 hour post-transfection; Western blot of nuclear PTEN was quantitated (with Lamin B1 as loading control) from three independent assays. (C) Transportin-2-PTEN protein interaction: Immunoprecipitates with PTEN antibody or IgG controls were analyzed by Western blot for PTEN or TRN-2 protein. PTEN-TRN-2 protein interaction is shown in the far right lane. (D) PTEN-Transportin-2 proteins are restricted at nuclear membrane detected by immunofluorescence staining of PTEN and TRN-2: Human primary hepatocytes were transfected with vmr11, Si-TRN2 and Si-Ctl oligonucleotides (50 μM of vmr11 mimic, twice at 0 hour and 24 hour). Cells were processed at 48 hrs post-transfection. PTEN is stained with FITC and TRN-2 with Texas Red.
Figure 4:
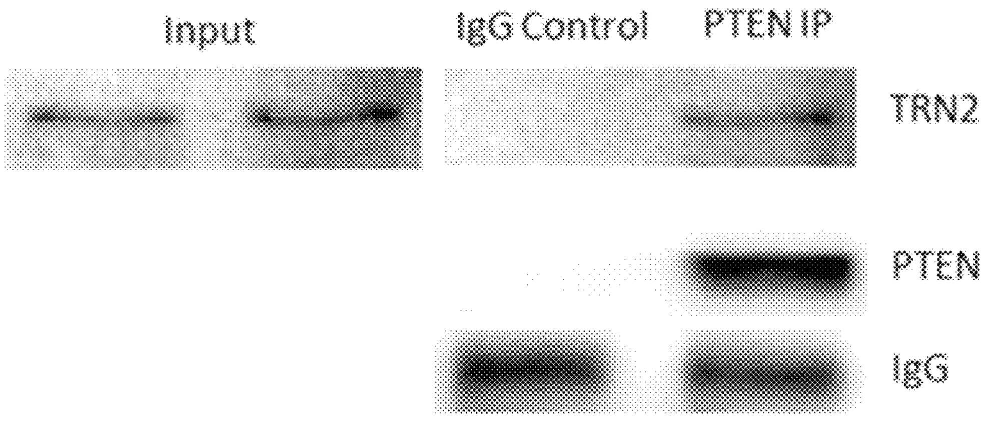
Figure 4:
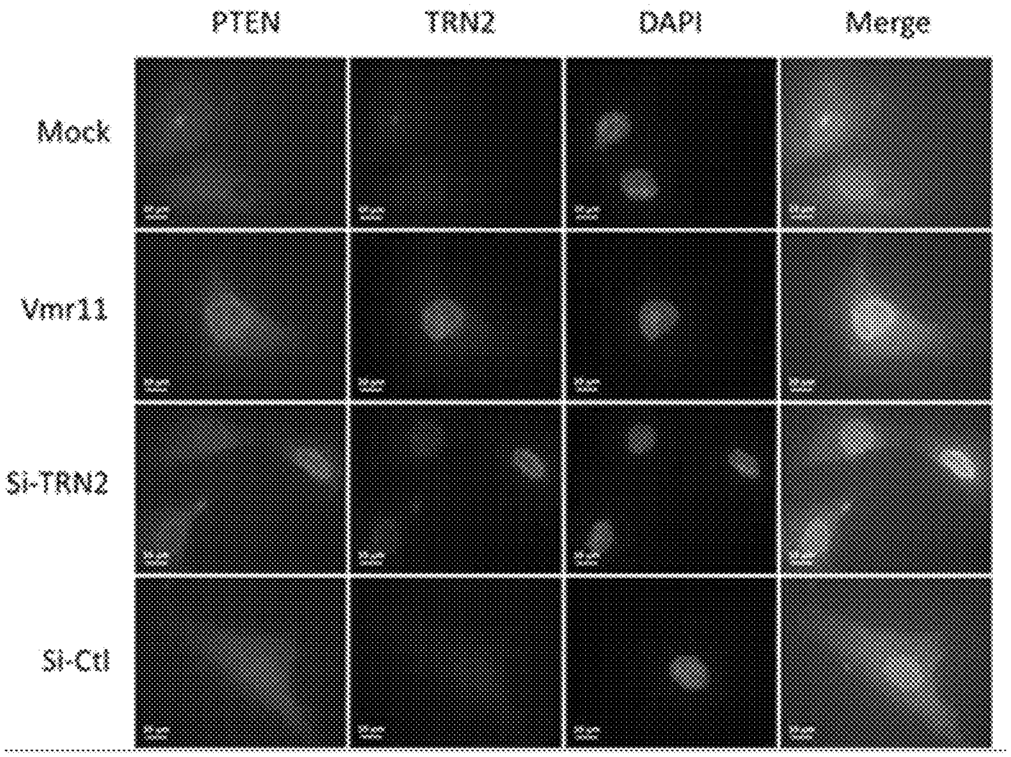

Although the array results do not directly identify the vmr11-modulated genes, target analysis of 3' UTRs of differentially down-regulated genes using the PITA prediction program [16] identified several potential vmr111 targets (Table 9), including Transportin-2 (TNPO2, also known as Karyopherin 1-2b). Transportin-2 is known to interact with nucleocytoplasmic shuttling proteins and to regulate their nuclear import [17-20]. Since both the results of expression arrays and the vmr11 targets predicted by PITA analysis of 3' UTRs suggested that vmr111 could target Transportin-2 (TRN-2) expression, we verified TRN-2 protein levels in cells transfected with vmr11 oligonucleotides (FIG. 4). We confirmed that TRN-2 was inhibited in human hepatocytes when the intracellular levels of vmr111 "mimic" oligonucleotides were artificially increased by transfection (FIG. 4A, second lane from left). Countering the effects of vmr111 with the antisense oligonucleotides (vmr11-Ctl, third lane) restored Transportin-2 protein levels. As controls, we observed the inhibition of TRN-2 protein by siRNA knockdown (Si-TRN2, fourth lane from left), which was not seen in cells treated with scrambled siRNA (Si-Ctl, fifth lane from left). Restoring TRN-2 by transfecting Transportin-2 cDNA following siRNA knock down (Si-TRN-2+TRN-2 CFP, far right lane) rescued intracellular Transportin-2 protein. Thus, introducing vmr11 oligonucleotides in uninfected cells appears to be sufficient to down-regulate Transportin-2 protein levels.

Next, we asked whether the down-regulation of TRN-2 influences PTEN protein levels in the nucleus (FIG. 4B). Western blots of nuclear PTEN show that knock-down of TRN-2 with siRNA (Si-TRN-2, third lane from left) is as effective in limiting nuclear PTEN as vmr11 'mimic' oligonucleotides alone (second lane from left). As a control, scrambled siRNA (Si-Ctl, fourth lane from left) had no effect on nuclear PTEN restriction. Interestingly, restoring the intracellular TRN-2 by introducing Transportin-2 cDNA, following siRNA knock down of TRN-2 (Si-TRN-2+TRN-2 CFP, far right lane), restored nuclear PTEN protein levels. These results indicate that the import of nuclear PTEN depends on Transportin-2.

To determine if the direct TRN-2-PTEN interaction is at least partially responsible for the nuclear import of PTEN, we performed immunoprecipitation assays. As shown in FIG. 4C, the PTEN antibody pull-down fraction (but not IgG controls) showed TRN-2-PTEN interaction. These results suggest that the nuclear translocation of PTEN depends on its binding to Transportin-2.

To further explore the mechanism of restriction of nuclear PTEN in TRN-2 deficient cells, we examined the intracellular distribution of PTEN in cells either transfected with vmr111 oligonucleotides or in which TRN-2 was depleted by transfection of siRNA. As a control, immunofluorescent staining of mock-transfected cells and cells transfected with scrambled siRNA (si-Ctl) showed a uniform intracellular distribution of both PTEN (green FITC stain) and TRN-2 (Texas red). Interestingly, in TRN-2-deficient cells (either due to vmr11, or by si-TRN-2 knock-down), the PTEN-TRN-2 complex appears to be restricted to the nuclear membrane area (FIG. 4D), suggesting that the nuclear translocation process is restrictive to suboptimal PTEN-TRN-2 protein complex.

Functional Domains of the HCV-Derived Vmr11.

Figure 5:
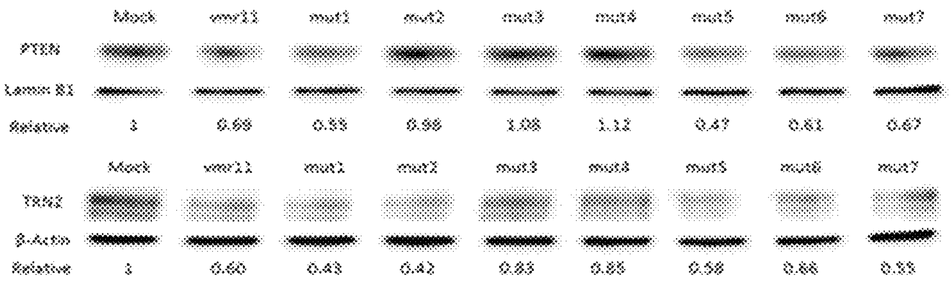
FIG. 5: Functional Domains of vmr11: (A) Base substitutions (shown in lighter grayscale, upper panel) of vmr11: PPH cultures were transfected with 50 nM vmr11 or vmr11 mutants (twice, at 0 and 24 hours) and total cell protein (for TRN-2), or the nuclear protein (for PTEN) was analyzed by Western blot. To determine TRN-2 or PTEN protein levels (relative values from two experiments are shown below each lane), β-actin or Lamin B1 were used as loading controls for TRN-2 and PTEN, respectively. In descending order, the nucleotide sequences are represented as SEQ ID NO:1 for vmr11 followed by SEQ ID NO:8-14 beginning with vmr11 mutant 1. (B) Virus production is positively correlated with nuclear PTEN restriction: $10^5$ PPH cells each were transfected with 1 μg HCV genomic RNA. A day later the cultures were either mock-transfected or transfected with vmr11 'mimic' or with one of the seven vmr11 mutants, as indicated. The oligonucleotide transfections were repeated twice (at 24 and 48 hour). Virus released in the culture media was harvested at 24-hour intervals as indicated. Viral RNA was analyzed by qRT-PCR. All viral RNA levels shown were normalized to 'mock transfected' cells at 24 hour. (C) Loss of nuclear PTEN and TRN-2 protein levels in cells transfected with vmr11 or one of the vmr11 mutants: As control, PTEN and TRN-2 protein from the same cultures where virus released into the culture medium was quantitated, (panel B) were analyzed by Western blot. Relative values of nuclear PTEN or TRN-2 proteins are shown below each lane.
Figure 5:
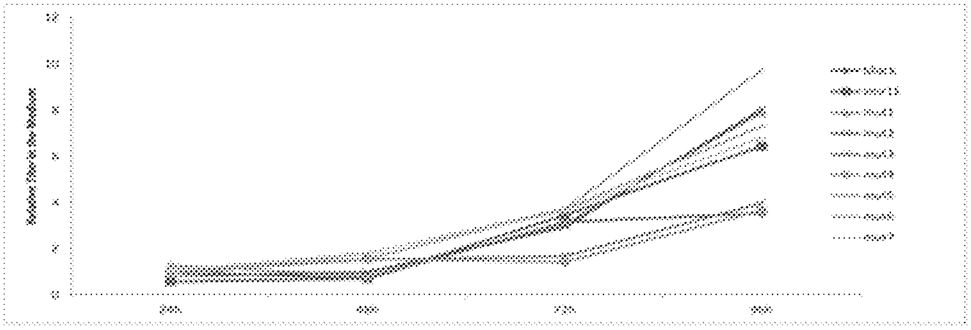
Figure 5:
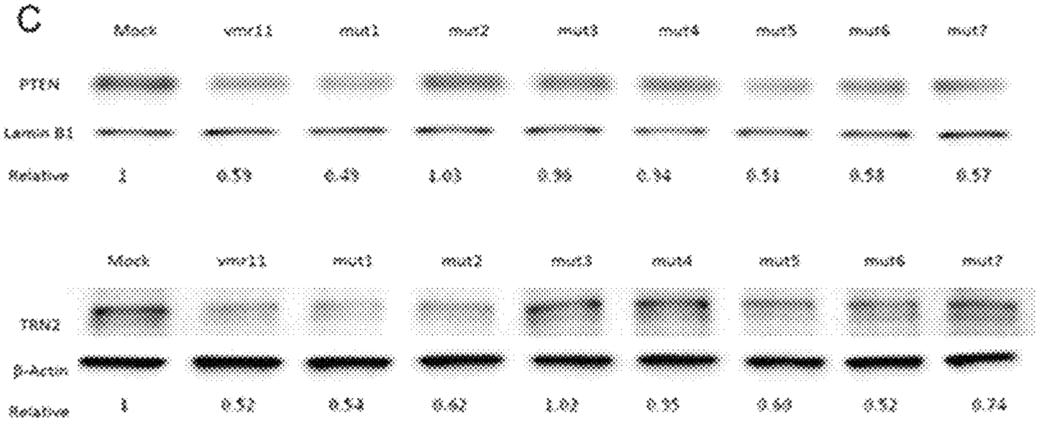

To determine 'functional domains' of vmr11 required for interaction with its TRN-2 target site, we examined base substitution mutants of vmr11 (FIG. 5A, upper panel) and compared the effects on TRN-2 silencing and consequent restriction of nuclear PTEN by Western blot (FIG. 5A, lower panel). In contrast with miRNA target recognition [21], the extreme 5'-sequence of vmr11 appears to be less critical for its TRN-2-target recognition. Indeed, inhibition of TRN-2 by vmr11 mutants 1 and 2 was similar to the wild type vmr11. Substitutions of nucleotides 7 and 8 (mutant 3) or nucleotides 9 and 10 (mutant 4), on the other hand, showed minimal inhibition of TRN-2, suggesting that nucleotides 7-10 of vmr11 contribute to the recognition of the TRN-2 target site. For the most part, nuclear PTEN protein levels also declined in parallel with the vmr11-targeted inhibition of TRN-2. As an exception, in cells transfected with mutant 2 (vmr111 base substitution from C4A5 to G4U5) the depletion of nuclear PTEN does not correlate with inhibition of Transportin-2. This finding suggests that mechanisms other than the TRN-2-PTEN interaction may contribute to restricting the nuclear PTEN translocation.

Replication of HCV is Positively Correlated with Restriction of Nuclear PTEN.

Experiments described thus far utilized vmr111 or vmr111 mutant oligonucleotides to artificially increase intracellular concentrations of vmr11. Next, we asked whether competition of vmr11 RNA produced in vivo in HCV replicating cells would influence TRN-2 protein levels and limit nuclear PTEN. Significantly, such assays allowed us to address whether virus production (HCV genomic RNA recovered from the culture medium of infected cells) increased in response to limiting nuclear PTEN protein.

To compete vmr11 RNA in vivo, we transfected the various vmr11 mutants (shown in FIG. 5A) into HCV infected human hepatocytes. As shown (FIG. 5B), base substitutions at nucleotides 7-10 (vmr11 mutants 3 and 4) that lost the capacity to recognize the TRN-2 target site, and hence showed no inhibition of TRN-2 protein or nuclear PTEN, minimally influenced HCV production. By contrast, vmr11 mutants (1, 2, 5, 6 and 7) that apparently do not interfere with TRN-2-target recognition, and hence allow the inhibition of TRN-2 and nuclear PTEN, favored virus production. These results suggest that depletion of nuclear PTEN favors virus production. Western blots of nuclear PTEN and TRN-2 proteins from the same cells that were scored for virus production are shown in FIG. 5C. Overall, the results suggest that reduced levels of nuclear PTEN protein in HCV infected cells favors virus production; and that PTEN can be restored in vivo by the introduction of competing vmr11 mutant oligonucleotides.

Depletion of Nuclear PTEN Correlates with Increased γ-H2AX

Figure 6:
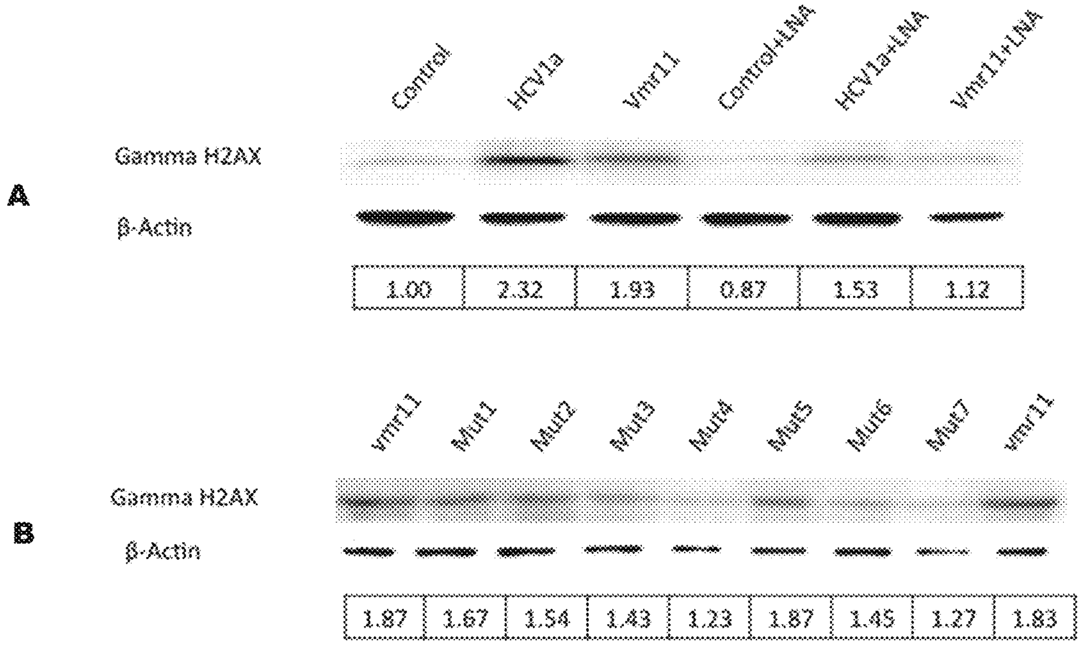
FIG. 6: Increased γ-H2AX in HCV1a infected or vmr11 transfected uninfected human hepatocytes: (A) Panel from left to right: Human hepatocyte cultures were either mock transfected (Control), transfected with 1 μg HCV1a (H77) genomic RNA, or transfected with 50 nM vmiR11 "mimic" oligonucleotides. Following, each of the mock, HCV1a-infected and vmr11-transfected cultures were treated with 50 nM vmr111 antagomir. The cells were harvested 3 days post-transfection and analyzed by Western blot for γ-H2AX. The numbers beneath indicate relative values of γ-H2AX normalized to 13-Actin loading control. (B) Western blots (of cells transfected with vmr11 oligonucleotides, similar to the results shown in upper panel) are compared to analyze the changes in γ-H2AX levels in cells transfected with either the WT vmr11, or with one of the vmr11 mutants (shown in FIG. 4A). The numbers underneath represent relative values normalized to the loading control (C) Immunofluorescence staining of γ-H2AX (FITC): Human hepatocytes were either infected with HCV1a (1 μg viral RNA HCV infection is marked with NS5A viral antigen, red stain, second vertical column from left), or transfected with vmr111 (50 μM) oligonucleotides, and processed for immunofluorescence viewing after 48 hours. γ-H2AX was stained with FITC and NS5A with Texas Red. Stained cell foci shown are at magnification 20× and 100× (inset). (D) Schematic representation of nuclear PTEN restriction in HCV-infected cells mediated by translational silencing of Transportin-2 with vmr11.
Figure 6:
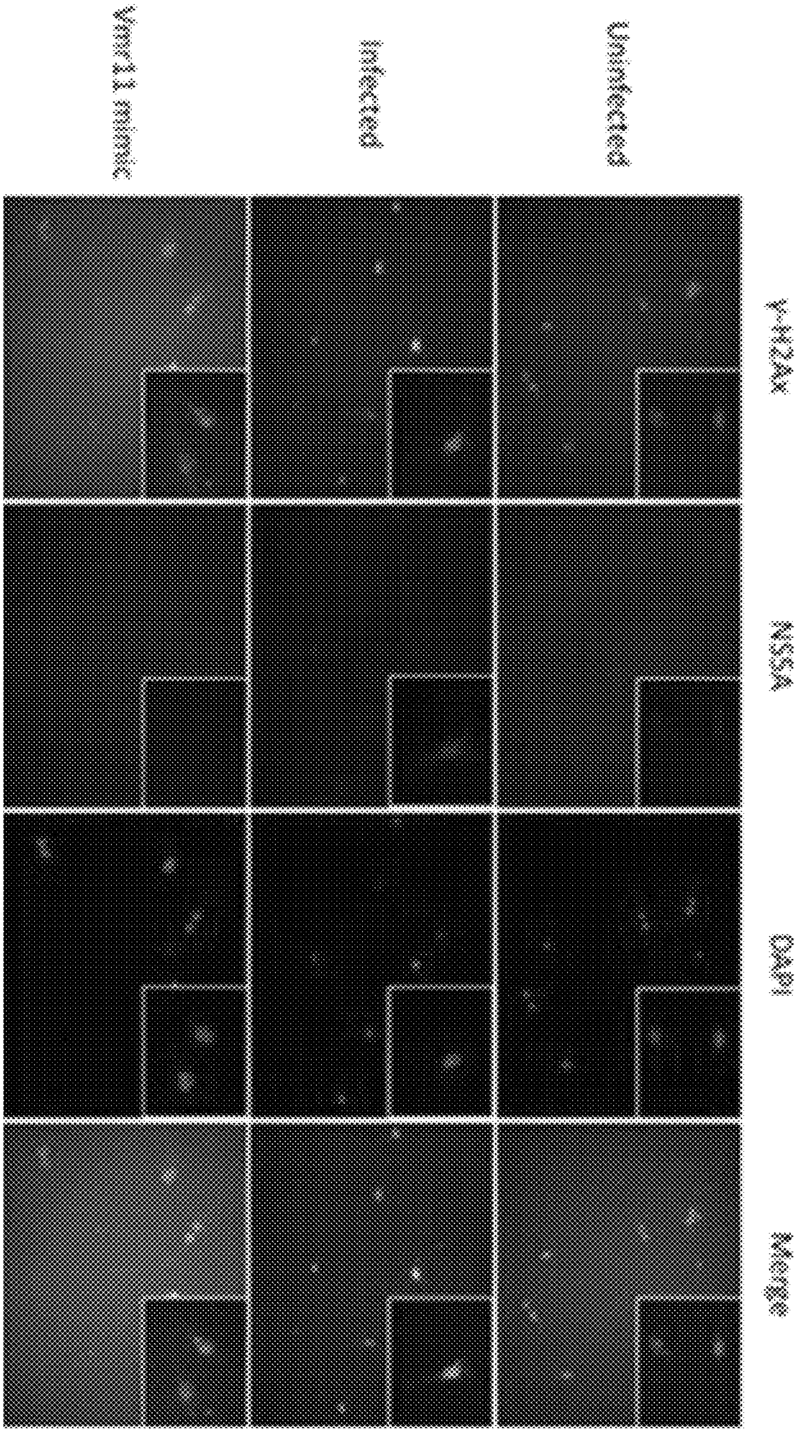
Figure 6:
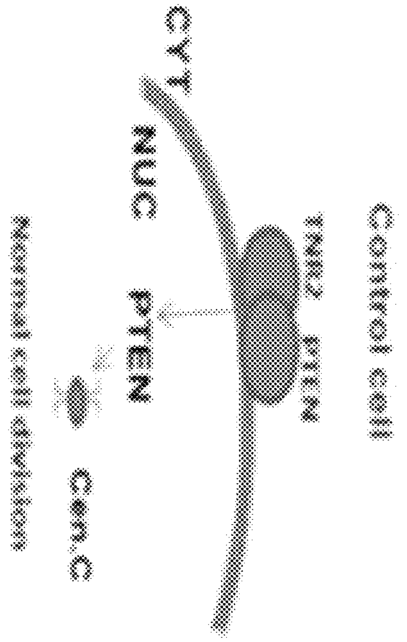
Figure 6:
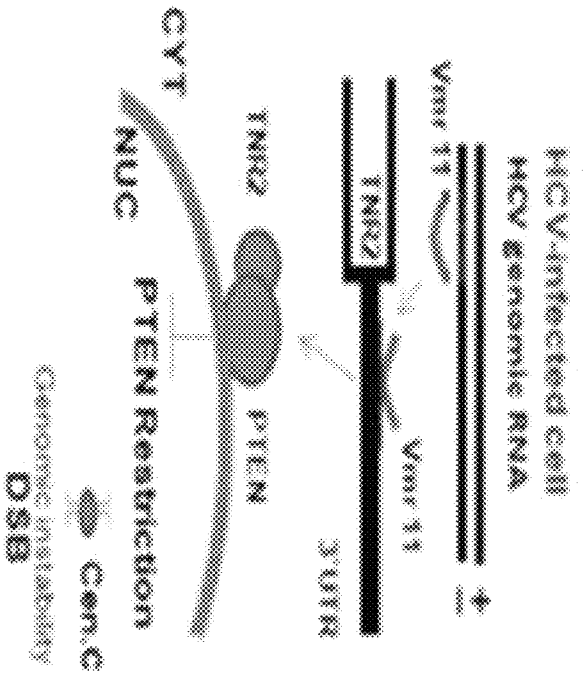

Nuclear insufficiency of PTEN has previously been shown to destabilize the centromere complex and to lead to DNA double strand brakes (DSB) [8]. Accordingly, we asked if the loss of nuclear PTEN in HCV infected cells correlated with DSB, a hallmark of genomic instability. We assessed the level of DSBs by utilizing antibodies to the phosphorylated form of histone H2AX (γ-H2AX), a commonly used marker for DSBs [22,23]. Western blots of HCV-infected hepatocytes showed increased γ-H2AX levels as compared to uninfected hepatocytes (FIG. 6A, second lane from the left). Consistent with the results shown in FIG. 4B, introducing vmr11 "mimic" oligonucleotide in uninfected cell was sufficient for the induction of γ-H2AX (FIG. 6A, third lane from the left). To validate that the vmr11-mediated inhibition of nuclear PTEN is in part responsible for inducing γ-H2AX, we countered the effects of vmr111 in vivo by introducing antisense vmr111 oligonucleotides in HCV-infected human hepatocytes and in the control cells transfected with vmr11 'mimic' oligonucleotides. The results shown in FIG. 6A suggest that the induction of γ-H2AX in PTEN deficient cells is due to the intracellular vmr11 RNA.

Analysis of vmr111 base-substitution mutants (FIG. 5A) allowed the functional validation of vmr11 domains that are required for the inhibition of nuclear PTEN. It was of interest therefore, to test whether introducing vmr11 mutants would also induce changes in γ-H2AX levels in uninfected cells. As illustrated in FIG. 6B base substitution mutants of vmr11 (mutants 2, 3 and 4) that are less likely to inhibit nuclear PTEN protein levels do not induce γ-H2AX to the same extent as the wild type vmr11. Overall, the results implicate PTEN nuclear insufficiency to the induction of γ-H2AX.

In an attempt to correlate the effects of HCV infection or transfection with vmr11 RNA to γ-H2AX induction in vivo, we compared immunostaining of γ-H2AX in human hepatocytes either infected with HCV or transfected with vmr11 'mimic' oligonucleotides. Immunostaining for NS5A viral antigen identified the HCV-infected cells (FIG. 6C). Visual inspection of the HCV-infected cells and control cells that were transfected with vmr11 'mimic' oligonucleotides identified relatively enhanced γ-H2AX staining nuclei. Overall, these results are consistent with the interpretation that depletion of nuclear PTEN in human hepatocytes, either due to HCV infection or by artificially increasing intracellular vmr11 RNA in uninfected cells, results in the induction of γ-H2AX.

To conclude, inhibition of Transportin-2 by the viral non-coding RNA, vmr11 limits PTEN translocation to the nucleus and is sufficient to induce γ-H2AX an indicator of DSB and genomic instability in HCV-infected human hepatocytes (an overview of the results, is depicted in FIG. 6D).

One of the critical steps in virus life cycle is their ability to modulate host defenses that favor virus propagation. For oncogenic virus such as HCV, a challenge is to define direct viral role in the depletion of PTEN tumor suppressor that correlates with more aggressive cancer, including HCC. The results described here suggest a novel mechanism of regulation of intracellular distribution of PTEN protein by viral non-coding RNA directed suppression of Transposrtin-2. Viral non-coding RNA mediated inhibition of Transportin-2 and the loss of nuclear PTEN in HCV-infected human hepatocytes implicate a direct viral role in oncogenic transformation. Consistent with that interpretation is our observation that HCV mediated nuclear insufficiency of PTEN correlates with DSB and genomic instability and efficient virus production.

Small RNA-based mechanisms, such as RNA interference (RNAi), play important roles in regulating the course of viral infection and viral pathogenesis in plants and animals [24-29]. Examples of virus-derived microRNAs have been reported in the human cytomegalovirus, Epstein Barr virus, Kaposi Sarcoma-associated virus, peach latent mosaic viroid [30,31], as well as in two viruses with RNA genomes, HIV-1 and BLV [27,32]. An earlier study [33] employing high-throughput sequencing predicted, albeit did not functionally validate, the presence of small viral RNAs derived from both positive and negative sense genomic RNA of several viruses, including HCV. By analyzing the conserved hairpin-loop structures of the HCV minus strand genomic RNA as a source of viral microRNA, we identified novel viral small non-coding RNA, vmr11, and have functionally validated the vmr11-dependent restriction of nuclear PTEN.

PTEN is a haploinsufficient tumor suppressor; partial depletion of PTEN is expected to profoundly influence cell cycle deregulation and genomic instability, hallmarks of oncogenic susceptibility. A number of mechanisms have been proposed to explain nucleocytoplasmic partitioning of PTEN [34-36]; however, there are no examples of PTEN restriction mediated by a human oncogenic virus. PTEN lacks both the conventional nuclear import (nuclear localization signal, NLS) and the nuclear export (NES) motifs [1,35]. No mutation has been reported among all the cases of nuclear PTEN 'mis-localization' examined [1], leaving open the possibility that nuclear translocation of PTEN may be regulated by 'non-genetic' mechanisms such as protein-protein interaction involving TRN-2.

PTEN deregulation plays a significant role in hepatopathogenesis [37, 38]. The proposed role of HCV core 3a in modulating the formation of PTEN-dependent large lipid droplets in hepatocytes [7] implicates a direct viral role in liver disease. Adding to these studies, the results described herein support a novel mechanism for regulation of PTEN translocation to the nucleus in HCV-infected cells. Specifically, nuclear insufficiency of PTEN in HCV infected cells results from the depletion of Transportin-2, which is mediated by a novel viral non-coding RNA, vmr11. Reduced levels of Transportin-2 in cells that are either transfected with vmr11 'mimic' oligonucleotides, or suffer siRNA knock-down of endogenous TRN-2, restrict the Transportin-2 and PTEN complex at the nuclear membrane. Collectively, these findings point to a novel mechanism of regulation of intracellular distribution of PTEN that is mediated by Transportin-2, a direct target of vmr11. The observation that the TRN-2-PTEN protein complex is restricted at the nuclear membrane leaves open the possibility that factor(s) other than protein interaction may be required for the PTEN translocation to the nucleus.

Perhaps the most intriguing consequence of nuclear PTEN insufficiency in HCV-infected cells is the induction of γH2AX, a major player in the recognition and repair of DNA double-strand breaks (DSB) and a hallmark of genomic instability and cancer susceptibility [8,39,40]. We observed enhanced staining foci of γH2AX-positive cells in HCV-infected or vmr11-transfected human hepatocytes. Whether DSB related to the nuclear PTEN insufficiency in HCV infection serve as an early indicator of HCV infection-associated hepatocellular carcinoma can be pursued in future studies in an animal model of HCV-infection associated HCC.

Post-Attachment Primary Hepatocytes (PPH)

A sustained primary human hepatocytes culture system was recently described [13]. Briefly, a co-culture of Hepatic Stellate cell line (CFSC-8B) was used as a 'feeder layer', to provide the extracellular matrix for efficient attachment of human primary hepatocytes suspension. The co-culture was maintained in a serum-free Hepatocyte-Defined Medium (HDM) for 30 days, during which the stellate cells (that require serum for their replication) are largely depleted. The primary human hepatocytes form "spheroids" that can be dispersed (with 0.05% trypsin treatment) and propagated as monolayers (independent of stellate cells), as 'Post-attachment Primary Hepatocytes' (PPH) in HDM supplemented with 1% FBS. The PPH cultures are dispersed with 0.05% trypsin and reseeded at 1:3 dilutions at weekly intervals.

Bioinformatics Prediction of HCV Small Non-Coding RNAs

The 9,646 bp negative sense HCV type 1 genome (GenBank accession: NC_004102) was divided, starting every 20 bp, into fixed size segments of length L=70 (80, 90 and 100). RNAfold [41] was employed to test each short sequence to determine stable hairpin structures that can form viral small RNA precursors. Hairpins that scored in the top 5% of the score distributions (determined by comparison to simulated random samples) were analyzed for conserved secondary structure by comparing 37 HCV type 1 complete genome sequences. Lastly, putative viral microRNA sequences were determined starting from conserved sequences 7 bp or longer ('seeds') that could be extended to mature 20-25 viral small RNAs.

Transfection of PPH Using H77 Run-Off Transcript pCV-H77c plasmid DNA was linearized for run-off transcription of full length genomic RNA using T7 Ribomax Express (Promega). 5×105 PPH cells were transfected with 1 μg of the H77 transcript using the Fugene 6 (Promega) procedure. Virus replication was monitored by quantitation of genomic equivalents (GE) of HCV RNA or by immune blotting for NS5A or HCV core antigens.

Real Time Quantitative PCR of Viral Small RNAs

1 μg of total RNA was reverse-transcribed using Quanti-Mir RT Kit (System Biosciences). The cDNA was diluted (100-fold) and amplified using PCR Supermix (Invitrogen) or iTaq SYBR Green Supermix with Rox (Bio-Rad) on GeneAmp PCR System 9700 or on ABI 7300 Real Time PCR system.

Subcellular Protein Fractionation and Western Blot

PPH cells were lysed with either RIPA buffer supplemented with 1× protease inhibitor cocktail (Roche), or with NE-PER nuclear and cytoplasmic extraction reagents (Thermo Pierce) for fractionations of nuclear or cytoplasmic proteins. Normally, 10 μg of protein was analyzed on 10% precast Mini-PROTEIN gel (BIO-RAD). The gels were transferred to PVDF membrane, blocked with 5% non-fat milk and probed with antibodies against PTEN (ab#79156 1:1000), GAPDH (ab8245, 1:5000), Lamin-B1 (ab#16048, 1:500), HCV core (ab50288, 1:1000) or γ-H2AX (ab11174, 1:1000).

Immunostaining

5×$10^4$ of HCV-infected or uninfected PPH cells were seeded into six-well plates with sterilized cover glasses one day before staining. The cells were washed with PBS and fixed with 4% paraformaldehyde, washed and permeabilized with methanol at −20° C., blocked with 1% BSA and stained with primary antibody against PTEN (ab32199, 1:100) and NS5A (ab20342, 1:100); followed by FITC or Texas Red conjugated secondary antibodies.

Quantitation of Virus from the Culture Medium of Infected Cells

QIAamp Viral RNA Mini Kit (QIAGEN) was used to extract RNAs from 140 μl of the culture medium of HCV-infected (or control) cells. The cDNA was prepared using QuantiTect Rev Transcription Kit (QIAGEN) and was analyzed with primers that target the 5' end of HCV (positive sense) genomic RNA. Primer sequences are:

```
                                        (SEQ ID NO: 2)
H77- QRT-Forward      (TGTGGAGCTGAGATCACTGG)
and

                                        (SEQ ID NO: 3)
H77-QRT-Reverse       (CCGCCTTATCTCCACGTATT).
```

Statistical Analysis

All Quantitative Real time PCR and densitometry data were analyzed using Microsoft Excel 2010.

RNA Labeling and Array Hybridization

Sample labeling and array hybridization were performed according to the Agilent One-Color Microarray-Based Gene Expression Analysis protocol (Agilent Technology).

Data Analysis

The Agilent Feature Extraction software (version 11.0.1.1) was used to analyze acquired array images. Quantile normalization and subsequent data processing were performed with the GeneSpring GX v12.0 software package (Agilent Technologies). Differentially expressed mRNAs were identified through Fold Change filtering (cutoff 2.0). Pathway analyses were performed using the standard enrichment computation method. Lastly, 3'UTRs of Gen-Bank RefSeq genes for vmr11 putative target analysis with PITA were extracted from the UCSC Genome Browser tables.

Example 2: Blocking HCV-Infection Associated Hepatocellular Carcinoma with LNA-Antagomir in a Mouse Model Hepatitis C Virus (HCV) infection is a major risk factor for chronic hepatitis and liver cirrhosis that can lead to hepatocellular carcinoma (HCC). Although newly approved antiviral drugs can effectively eliminate HCV, liver damage due to chronic infection that may have ensued decades before antiviral therapy, leaving an unforeseen burden of end-stage liver disease. There is urgent need to identify markers of HCV infection associated liver cancer and novel targets for early intervention and cure for HCC.

Purpose of this study is to validate the feasibility of virus-specific synthetic antisense RNA to block HCV infection associated HCC. Study focuses on the determination of the effects of virus-specific antisense RNA to counteract HCV-infection associated oncogenic genes. The study further focuses to determine the efficacy of HCV-specific antisense RNA as inhibitor of HCV-induced HCC in humanized mouse model.

We have characterized oncogenic markers of HCV-infection associated HCC and validated its function in the mouse model (MUP-uPA/SCID/Bg) [43]. This animal model of HCV infection associated HCC will be exploited to determine the efficacy of stable HCV-specific antisense RNA for liver cancer therapy. Supporting results are as follows:

Oncogenic Markers of HCV-Infection-Associated HCC.

We observed marked inhibition of tumor suppressor proteins, PTEN, HNF4a and DLC1, and induced levels of the Myc oncoprotein in liver tumors of HCV-infected MUP-uPA/SCID/Bg mice.

Figure 7:
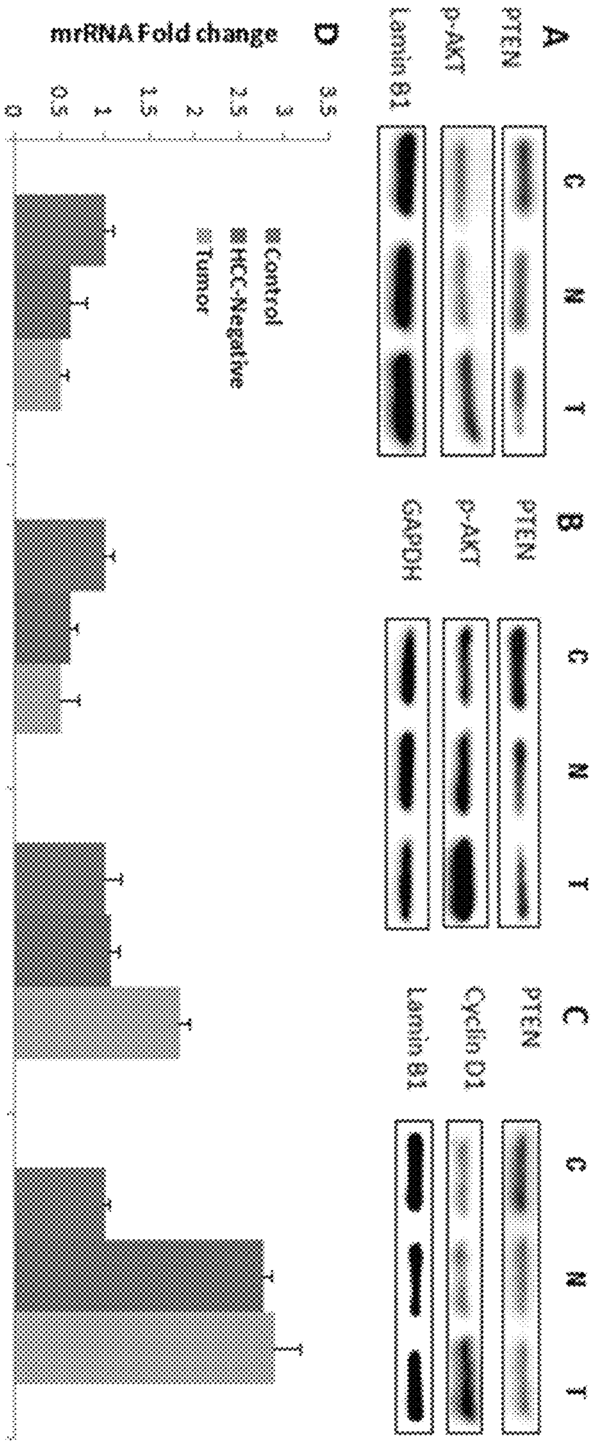
FIG. 7: Control (C), (MUP-uPA/SCID/bg engrafted with human hepatocytes but NOT infected with HCV); HCCnegative (N) (engrafted, HCV infected animals that did not develop HCC); and HCC tumor tissues (T) (engrafted and HCV infected) were examined by Western blotting with monoclonal antibodies for PTEN) (A and B). Phospho-Akt (A and B) and Cyclin D1 (C). RIPA buffer homogenized the liver tissues and 30 microgram protein per lane was resolved in SDS-PAGE, and immunoblotted as described before [6]. (D) is quantitative assessment of proteins analyzed in three independent runs of seven liver tissues of each type.

PTEN tumor suppressor is the central negative regulator of the PI3 signaling cascade for cell proliferation [44]. We observed increased phosphorylation AKT, a serine/threonine-specific protein kinase with key role in cell survival and cell proliferation; phospho-AKT (pAKT) is important factor in many types of cancer. The induced levels of pAKT in liver tumors (FIGS. 7A nuclear, and 7B) suggests direct role of PTEN depletion in the development of HCC [45, 46].

Normal levels of nuclear PTEN is essential for Gi cell cycle arrest, as PTEN down regulates Cyclin D1 and maintains cell cycle checkpoint [47]. We observed reduced nuclear PTEN (FIG. 7C) and increased in Cyclin D1 in HCV-infected liver tumors, consistent with enhanced proliferation of HCV-infected human hepatocytes [48]. Reduced nucleat PTEN in HCC-negative liver correlated with increased Cyclin D1 (FIGS. 7C and D, comparable to tumor tissue), Results suggest that PTEN depletion may be an early indicator in HCV infection associated hepatocarcinogenesis.

Another critical marker of HCV-infection associated liver tumor is the hepatocyte nuclear factor 4a (HNF4a). Depeltion of HNF4a in HCV infected human hepatocytes is a direct result of viral non-coding RNA vmr111. Significantly, our results show that synthetic antisense vmr11 nucleotides restore normal levels of HNF4a tumor suppressor protein, thus providing proof of principle for small non-coding RNA based therapy of liver cancer. Our results have shown that depletion of HNF4a in HCV infection promotes the expression of epithelial to mesenchymal transition (EMT) genes, a hallmark of metastasis.

Induction of Oncoprotein c-Myc.

Figure 8:
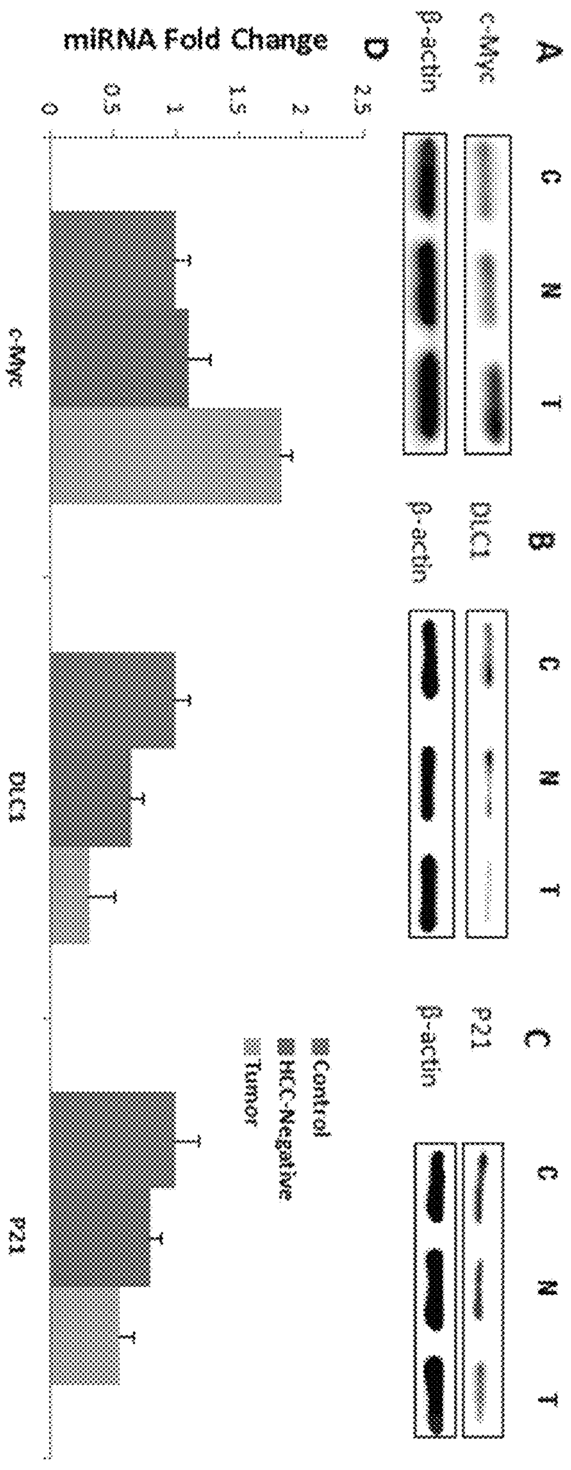
FIG. 8: Similar analysis of the control, HCC-negative and infection induced liver tumors (as in FIG. 7) by Western blotting for c-Myc, DLC-1 and p21 proteins (A, B and C). The lower part, (D) is quantitation (based on the loading controls), presented as relative values of each protein in Controls (C) HCC-Neg(N) and HCC (T).

Transcription factor cMyc is constitutively induced in broad range of human cancer, and has a key role in tumor progression [49]. Myc is a nonlinear amplifier of gene expression, acting universally at active genes. We observed increased cMyc protein in HCV-infected mouse liver tumor as compared to the control (FIG. 8A). Induction of cMyc in HCC-negative liver appears to be modest (FIG. 8D).

Down Regulation of DLC-1 Tumor Suppressor.

Deleted in Liver Cancer 1 (DLC1) gene maps to chromosome 8 (8p21.3-22), a region frequently deleted in solid cancers. The DLC1 encodes GTPase-activating protein (GAP), a member of rhoGAP family of proteins. DLC1 functions as tumor suppressor; depletion of DLC1 is an independent marker of hepatocellular carcinoma.

We observed marked inhibition of DLC1 in HCV-infected liver tumors; less so HCC-negative controls (FIGS. 8B and 8D).

p21.

The p53 tumor suppressor dependent expression of p21, the cyclin-dependent kinase inhibitor (also known as p21WAF1/Cip1), is an important indicator of cell cycle deregulation in cancer [50]. Marked decline in p21 levels of HCV-infected liver tumor (FIGS. 8C and 8D), suggests inhibition of p53 tumor suppressor in HCV-infection associated HCC.

MicroRNA Markers of Liver Tumor.

Figure 9:
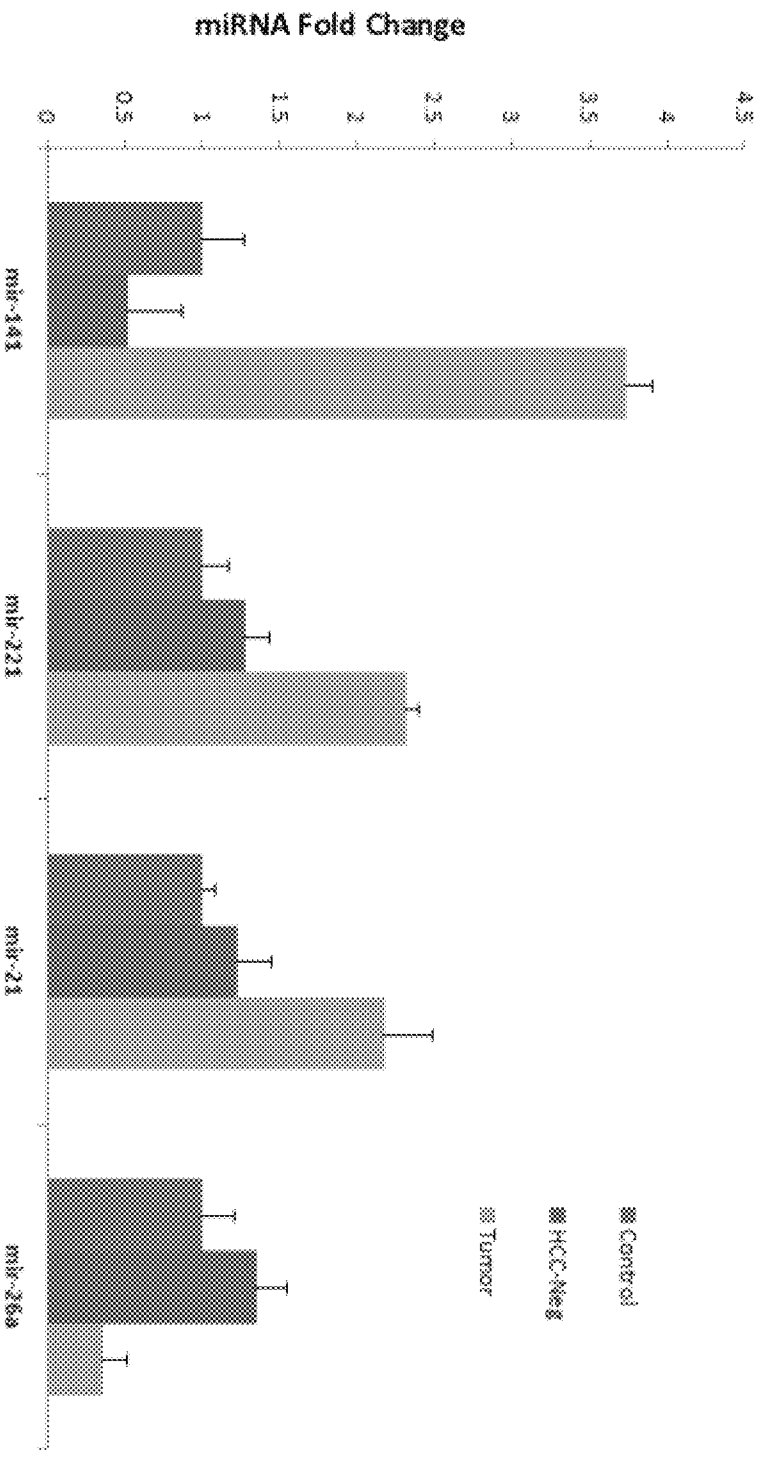
FIG. 9: Changes in microRNA expression in Controls, HCC-neg and tumor tissues. Total RNA was prepared by Trizol procedure and equal amounts were analyzed by qRT-PCR. The data represents similar number of C, N and T samples analyzed in triplicates.

MicroRNAs can function as tumor suppressors or oncogenes (oncomiRs) [51, 52, 53]. Dependence of HCV replication on miR-141 mediated downregulation of DLC1 identifies miR-141 as bona fide oncomiR [54]. Our results of HCV-infected mouse liver tumor suggest that along with the amplification of oncomiR, miR-141, two other tumor promoting oncomiRs, miR-21 and miR-221, that target cell cycle inhibitors [55, 56, 57], are deregulated in HCV-infection associated HCC. By contrast, microRNA 26a (miR-26a), which targets cyclin D2 and E2 expression and regulates Gi cell cycle arrest, is markedly inhibited in liver tumors as compared to the adjacent normal liver and other tissues [58]. We observed similar down regulation of tumor suppressor miR-26a in HCV-infected mouse liver tumors (FIG. 9). Overall, the results argue that development of HCC may be programmed by cooperative interaction of oncogenic proteins and miRNA-regulated genes, and that our humanized mouse model of HCV-infection associated HCC is suitable to examine the questions raised in the proposed specific aims.

Hepatocyte Nuclear Factor 4α.

Figure 10:
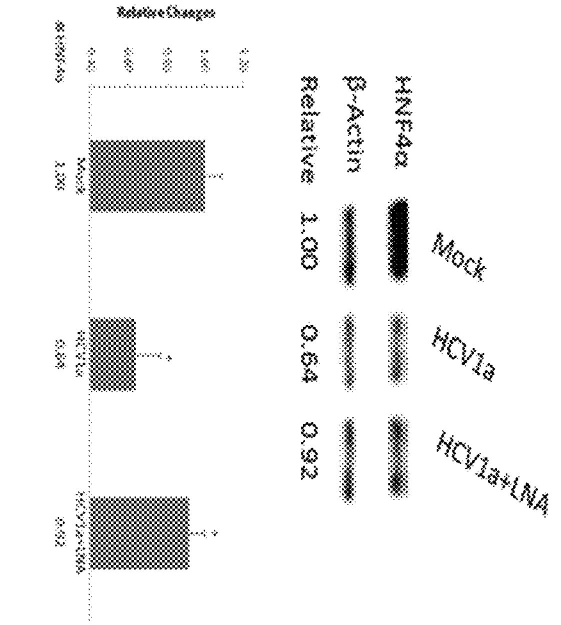
FIG. 10: HCV-derived 22 nucleotide vmr111 inhibits HNFα (A), and (B). Inhibition of HNF4 in chimeric mouse model of HCV-infection associated HCC correlates with inhibition of E-Cadherin and the induction of Snail, and TGF expression, consistent with the role of HNF4 tumor suppressor (C) and (D).
Figure 10:
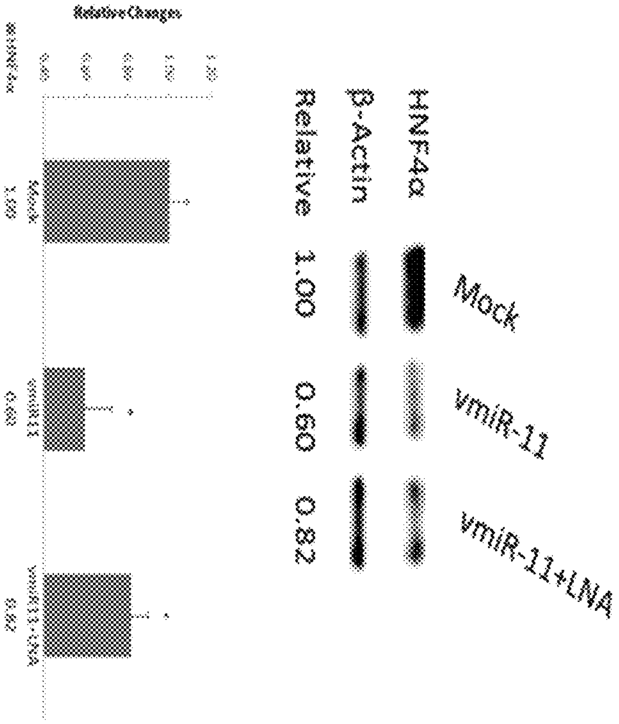
Figure 10:
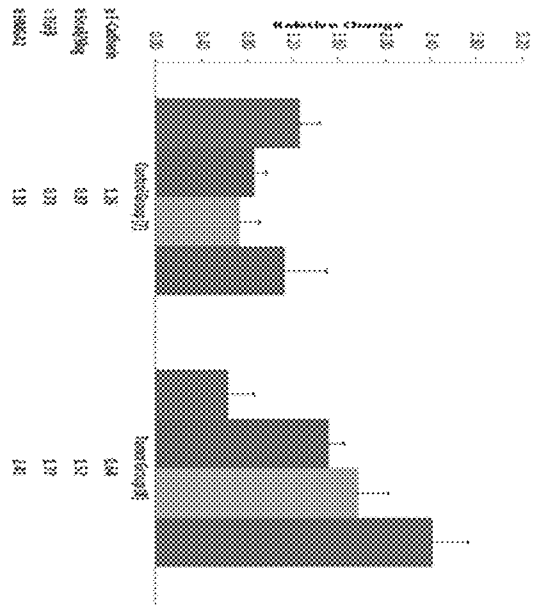
Figure 10:
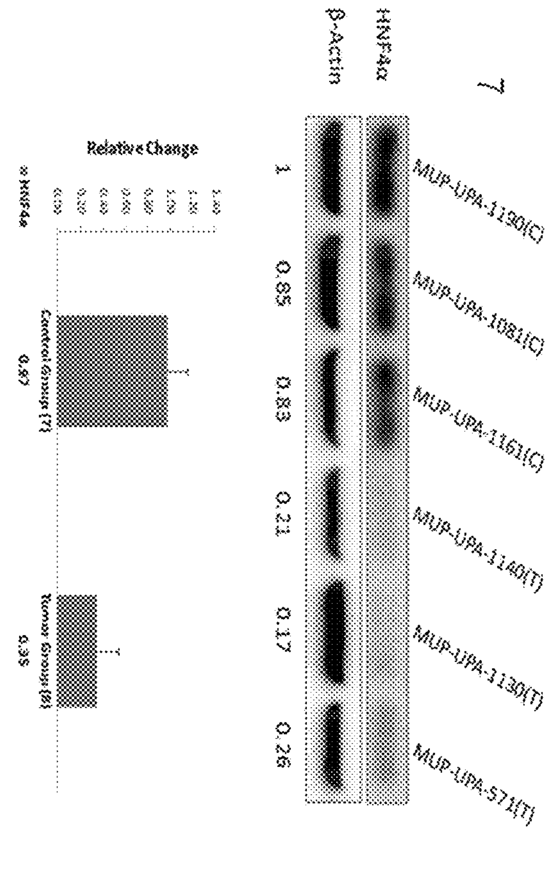

Hepatocyte nuclear factor 4αHNF4α) is critical for liver development and differentiation; suppression of HNF4α has been linked to hepatocellular transformation [59]. Here we asked whether the inhibition of HNF4α in HCV infected human hepatocyte-engrafted mice promotes transcriptional program of Epithelial to Mesenchymal Transition (EMT) and tumorigenesis in the mouse model. Inhibition of HNF4α in our chimeric mouse model of HCV-infection associated HCC correlates with inhibition of E-Cadherin and the induction of Snail, and TGF-β expression, consistent with the role of HNF4α tumor suppressor (FIGS. 10C and 10D). Interestingly, HCV derived 22 nucleotide vmr11, appears to be sufficient to inhibit HNF4α in HCV-infected human primary hepatocytes (FIGS. 10A and 10B).

The results support the argument that countering translational silencing of HNF4α with antisense vmr11 (e.g. with an antagomir), should block the progression of HCV-infection associated hepatocarcinogenesis.

Aim 1.

Blocking the expression of HCV-infection associated oncogenesis with stable HCV-specific antisense RNA.

We reasoned that the antisense nucleotide (antagomir) should satisfy the following criteria: (a) the antagomir be "stable" for use in human hepatocyte cultures and in vivo in animal model of HCV-infection associated HCC; (b) the antagomir should interfere with binding of vmr11 and the host target genes to restore normal levels of tumor suppressor proteins in HCV-infected cells.

Results of site-directed mutagenesis studies have shown that "functional domain" of HCV-derived small non-coding RNA "vmr11" includes seven nucleotide (underlined, 5'-GUUCAUCAUCAUAUCCCAUGCC-3') (SEQ ID NO:1) sequence where base substitutions disrupted vmr11-target recognition and the inhibition tumor suppressor genes (HNF4α and PTEN).

We will synthesize 2'-Fluoro-modified sevenmer (5'-GAUGAUG-3') complementary to the functional domain of vmr111 to assess the effects of loss of function of vmr11 in HCV-infected human primary hepatocytes. In "locked" nucleic acid (LNA), the ribose moiety of a nucleotide is modified with an extra bridge connecting the 2' oxygen and 4' carbon that 'locks' the ribose in 3'-endo confirmation. The LNA-modified oligonucleotides have significantly increased hybridization (melting temperature) properties, and sensitivities as stable probes for use in vivo [60, 61]. Synthetic LNA-anti-vmr111 (Exiqon[INC]) will be introduced by transfection in human hepatocye cultures with or without HCV infection, and the levels of oncogenic markers monitored by Western blotting (as described in supporting studies above).

2-Fluoro NTPs improve in vivo stability, increase target specificity, and are resistant to nuclease degradation, suitable for use in animal model. Restoration of tumor suppressor protein levels in HCV-infected cells with stable anti-vmr111 oligonucleotides will verify the effects of HCV-derived vmr11 in promoting oncogenesis. By comparing the levels of oncogenic markers in cells transfected with vmr11 alone to cells co-transfected with vmr11 "mimic" and anti-vmr11, we will be able to evaluate direct effect of HCV-derived non-coding RNA in promoting oncogenesis.

Aim 2.

Validation of vmr11 antagomir effect on HCV-infection associated HCC in mice.

We reasoned that development of HCV infection associated HCC in humanized (MUP-uPA/SCID/Bg) mouse model can be arrested in part by preventing vmr11-dependent depletion of the tumor suppressor genes in presence of anti-vmr11.

The reasoning anticipates that HCV-derived vmr11 sequence may play a critical role in driving the oncogenic process. To approach the issue we designed the experimental approach as follows:

(a) Control animals: (Five) Human hepatocyte engrafted but uninfected MUP-uPA/SCID/Bg mice.

(b) HCC+(15*) Engrafted+HCV infected mice.

(c) vmr11 "mimic" (15*) Engrafted mice transduced with vmr11 "mimic" oligonucleotides.

(d) anti-vmr11

The human hepatocyte engrafted mice will be infected with HCV, plus treated with vmir11 antagomir. One third of the HCV-infected mice develop tumors; these numbers are expected to yield about 5 mice with liver tumor.

By comparing the histopathology and oncogenic markers of liver tissue from (a) and (b) we will be able to establish a "baseline" of genes that define the HCV-infection induced tumorigenic process in human liver. Similar comparison of histopathology and molecular markers in (a) and (c) will allow assessment of the vmr111 modulated genes in hepatocarcinogenesis. A comparison of the liver tissues from (b) and (d) will define contribution of HCV-derived small non-coding RNA (vmr11), in the regulation of genes that promote liver cancer.

Pairwise comparison of protein and RNA samples from the liver tissue will be analyzed by Western blots or qRT-PCR as outlined above. For broader perspective and to generate data for hypothesis driven approach, we will analyze Expression Arrays (Array Star™, using Agilent platform) of four types of mouse liver tissues (outlined above). These studies will suggest coordinated regulation of genes whose deregulation favors oncogenic program of HCV-infection associated HCC. Functional validation of the key markers of oncogenic pathways will be validated by siRNA knock down followed by Western blots and RT-PCR assays, as outlined.

Example 3: Functional Implications of RNA Parallel Duplex Structures in Human Hepatocytes In preliminary studies we identified non-coding RNA from hepatitis C virus (HCV) minus strand genomic RNA (vmr); target validation of vmr11 showed inhibition of three target mRNAs, tumor suppressors PTEN and HNF4alpha and Transportin-2 each with critical roles in liver function. Studies with base-substitution mutants suggest that the central, CAUCAUC sequence of vmr11 is critical for target mRNA recognition (and translational inhibition). Focus of this experiment is to understand physiological context of viral non-coding RNA (vmr11), and structural basis of mRNA silencing.

Recent x-ray studies provide proof of RNA parallel duplex structure (RNApds) at high resolution in studies of synthetic poly $(rA)n_{11}$ with A:A Hoogsteen base pairs [62]. We propose studies of in vivo RNA parallel duplex structure formed with trans-acting viral non-coding RNA (vmr11, CAUCAUC sequence) and target mRNAs, and its functional implications in HCV-infected human hepatocytes.

Figure 12:
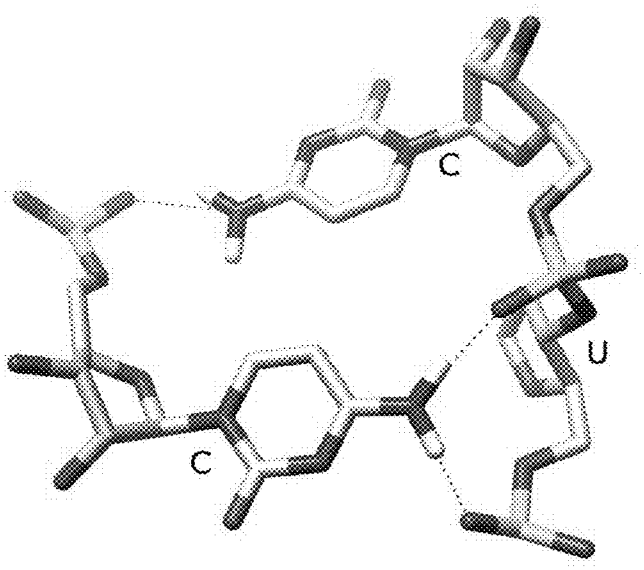
FIG. 12: Proposed A:A tHH base pair, and hydrogen bonding schemes for pyrimidine base C in RNA parallel duplex structure (A). RNA parallel duplex structure; CAUCAUC double stranded parallel structure (B).
Figure 12:
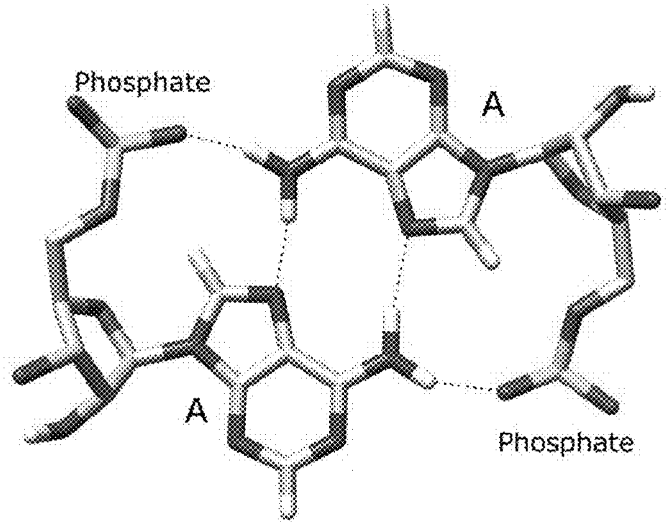
Figure 12:
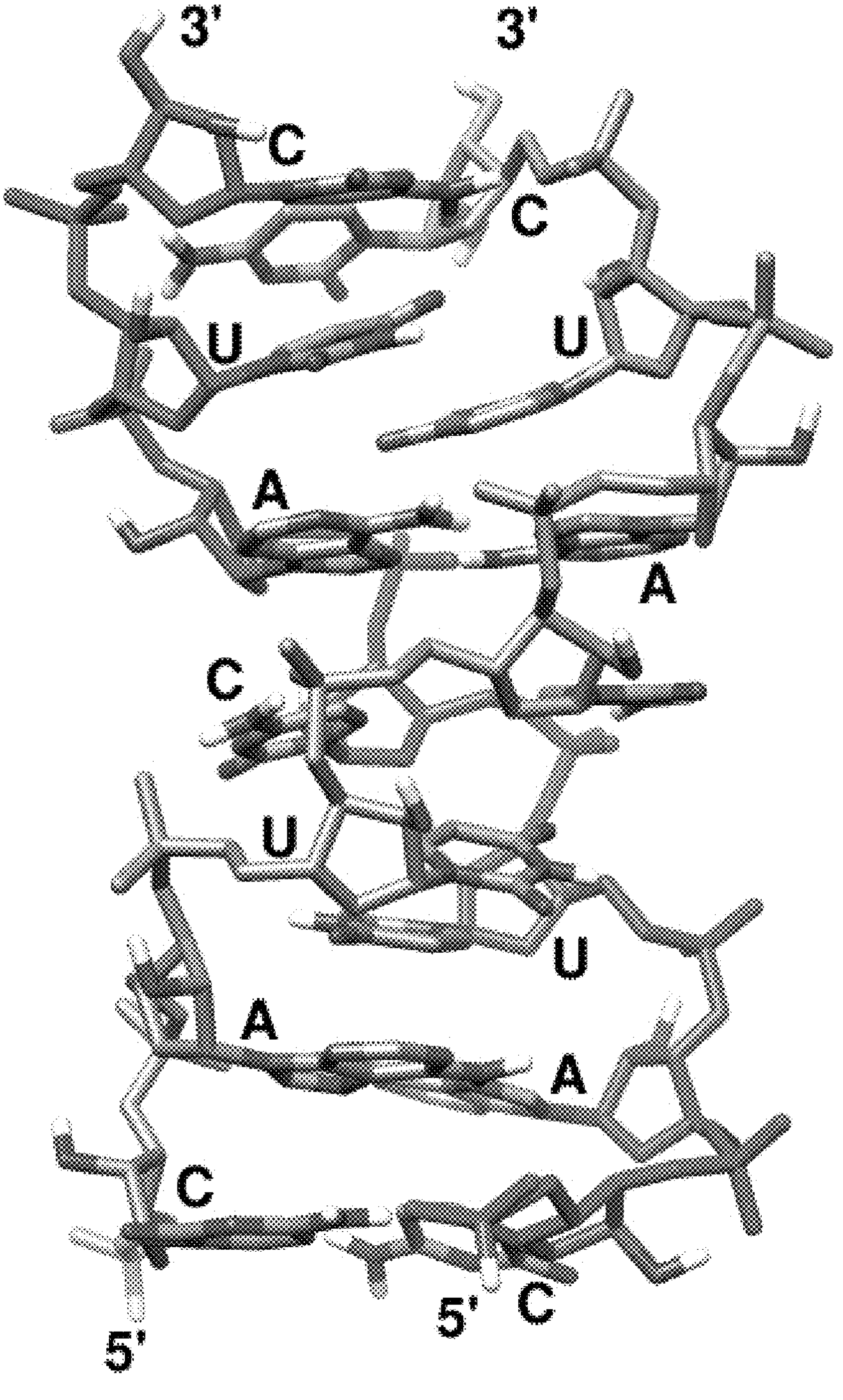

Double stranded DNA forms right handed double helical structure [63], by base pairing between A and T and G and C. Alternative structures have been proposed for antiparallel DNA duplex, such as uniform left-handed DNA [64], zig-zag DNA [65] and side-by-side zipper model [66]. These structures however, have not been verified in biological experiments; except for the left-handed duplex (Z-DNA), which is formed in alternating $(CG)_n$, and has been confirmed in biological systems [65, 67, 68, 69, 70, 71]. Pattabiraman [11, 12] proposed a parallel DNA duplex structure for sequences containing only A and T bases. In parallel duplex structure, directions of the two strands (5'→3') are in the same orientation; A is paired with T as reverse Watson-Crick base pair (FIG. 12). Studies test whether RNA parallel duplex formation between the CAUCAUC sequence of trans acting viral non-coding RNA (vmr11) and target mRNAs interfere with target mRNA function (translation and/or stability).

Alternate structures of DNA parallel duplexes have been proposed, and in some cases, validated in studies with synthetic oligonucleotides. However, examples of RNA parallel duplex structure, or its physiological context in human cells are rare. In Preliminary Studies (supporting data) we identified hepatitis C virus (HCV) derived non-coding RNA, vmr11, containing CAUCAUC sequence which is predicted to form RNA parallel duplexes (RNApds) with limited number of target mRNAs: HNF4alpha TNPO2 and PTEN. Target validation by immunoblotting, and functional confirmation using base substitution mutants suggest a critical role of CAUCAUC sequence in the inhibition of target mRNAs that encode tumor suppressor proteins with critical role in liver function. To explore biological significance of the RNApds, we asked two main questions: (i) how are the non-coding RNA derived from viral genomic RNA, and (ii) how do the RNA parallel duplex structures influence target mRNA translation.

Aim 1: To Analyze the Derivation of 22 nt Vmr11 RNA Sequence from HCV Genomic RNA.

In vivo bromo-uridine (BrU) pulse labeled RNA from HCV-infected or control cells will be immunopurified by anti-BrdU antibody-coated protein G Sepharose, and analyzed by Northern blots using $^{32}$P-labled 'antisense' or 'sense' HCV genomic RNA probes.

Aim 2: To Validate Functional Significance of the Predicted RNA Parallel Duplex Structures, by Base-Substitution Mutants of CAUCAUC Sequence of Vmr111.

Functionally relevant vmr11 mutants will be verified on the basis of translational silencing of mRNA targets. The results will inform future studies with vmr11 as RNA-capture probes to identify RNA-binding protein(s) that might regulate RNA parallel duplex formation.

Implications:

The unique nature of RNA parallel duplex structure, and the fact that it affects post-transcriptional silencing of limited number of mRNAs, suggests that antisense oligonucleotides to interrupt RNApds can be effective in blocking oncogenic progression in HCV infected cells. Results will lay the foundation for future studies to ask if RNA-binding proteins modulate the trans-acting viral non-coding RNA and target mRNA interaction, and/or the formation and the stability of parallel RNA duplex structures. RNA-binding proteins are known to play significant role in stabilizing parallel duplex structures [62], and can be valuable in future crystallography studies to explore novel anticancer drugs based on structural analysis of RNA parallel duplex. The results will provide a framework to examine the role of proteins that stabilize RNA parallel duplex structures in vivo, which will facilitate better understanding of novel targets for therapy of liver cancer.

Background and Preliminary Results:

The positive sense 9.6 kb HCV RNA genome is translated as ~3000 amino acids long polyprotein, which is processed into ten viral structural and non-structural proteins in infected hepatocytes [74]. HCV has evolved mechanisms to evade host defenses [75, 76, 77], although, our understanding of how HCV infection initiates the oncogenic process remains incomplete. We plan to study proto-oncogenic potential of HCV-derived non-coding RNA (vmr11), and identify markers for early detection and possible novel therapy of hepatocellular carcinoma.

Figure 11:
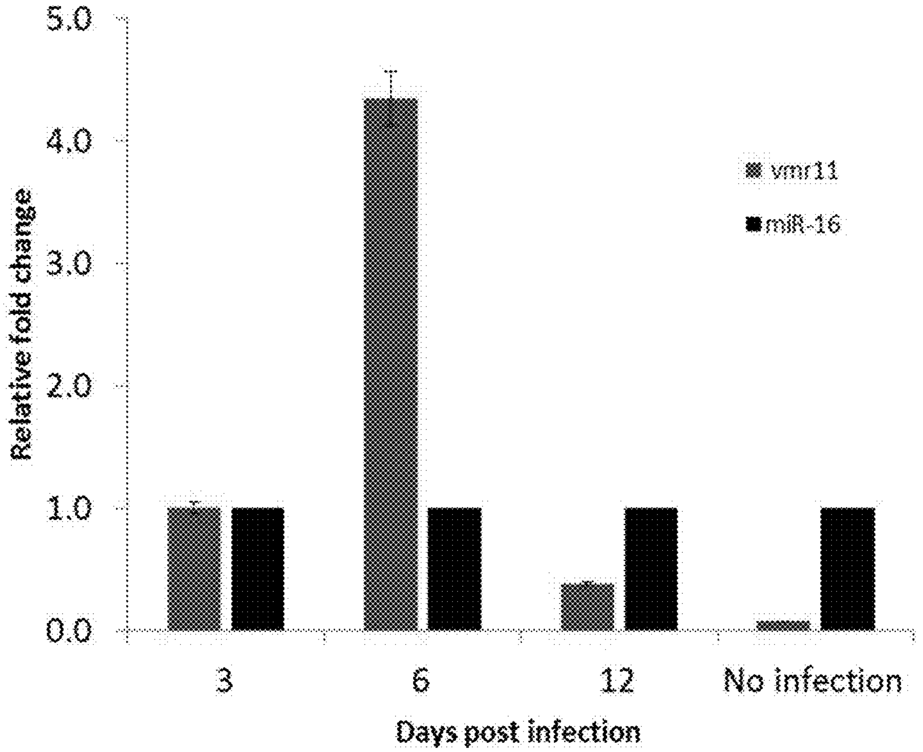
FIG. 11: HCV-derived viral small RNAs were analyzed using RT-PCR. The results represent a robust increase in vmr111 levels six days post-infection with HCV1a, and only minimal change in vmr20. As control, miR-122 level is minimally changed upon viral infection (18S marker serves as internal reference). The schematic at the top left comprises four nucleotide sequences in descending order spanning SEQ ID NO:48-51 (A). The predicted secondary structure of vmr11 precursor; mature vmr shown in red. The top sequence is SEQ ID NO:46, and the bottom sequence is SEQ ID NO:47 (B). QRT-PCR analyses of vmr11 with increasing times post-infection. $1\times10^5$ PPH cells were transfected with 1 mg of HCV1a genomic RNA and harvested on days 3, 6 and 12 post-infection. The levels of vmr11 were monitored by qRT-PCR. (Data shown was normalized to miRNA16, which does not change with HCV infection) (C).

Small RNA-based mechanisms, such as RNA interference (RNAi), play important role in regulating the course of virus infection and viral pathogenesis in plants and animals [78-83]. Examples of virus-derived microRNAs have been reported in human cytomegalovirus, Epstein Barr virus, Kaposi Sarcoma-associated virus, peach latent mosaic viroid [85, 86] as well as in viruses with RNA genomes, HIV-1 and BLV [81, 86]. A recent report predicted, but not validated [88], virus-derived small RNAs from both positive and negative sense genomic RNAs, in a number of virus-infected cells, including HCV. By analyzing conserved hairpin-loop structures as source of viral small non-coding RNA from HCV minus strand genomic RNA, we identified 22 nt vmr11 RNA (FIG. 11). The rationale for vmr11 derivation is outlined in FIG. 11A.

Aim 1: Derivation of Vmr11 from HCV Genomic RNA:

Our working hypothesis for this aim is that HCV derived vmr11 RNA should accumulate in parallel with the viral genomic RNA. Secondly, the vmr11 sequence (derived from the minus strand genomic RNA) should be complementary to the positive sense viral RNA 'probe' in Northern blots.

Preliminary Results Related to Aim 1:

In preliminary experiments (FIG. 11*c*) we observed vmr11 RNA accumulation in HCV infected cells, in parallel with viral genomic RNA replication. The accumulation vmr11 appears to be insensitive to Dicer but sensitive to RNase L knock down (not shown). To ascertain if the RNase L cleavage of viral genomic RNA favors vmr11 production, we plan to analyze in vivo BrU 'pulse' labeled HCV RNA in infected human hepatocytes, without or with siRNA knock down to reduce RNase L, and determine the levels of vmr11 RNA by Northern blotting.

Aim 1: (Experimental Approach),

To verify biochemical derivation of vmr11 sequence we plan to pulse label HCV RNA (with 150 micro-Molar BrU, at sequential time points in HCV (genotype1a) infected or control human hepatocytes (procedure for HCV1a replication in human hepatocytes was described earlier [89, 90]). 5'-bromo-uridine labeled RNA will be immune fractionated with anti-BrdU monoclonal antibody-coated protein G-Sepharose beads, essentially as described [91]. Total RNA from control or HCV infected cells will be resolved on denaturing (urea-SDS PAGE) gels and Northern blotted with $^{32}$P-labeled viral RNA probes. The run-off $^{32}$p-labelled probes will be derived from vmr11 precursor sequence (8330-8390; FIG. 11B), cloned into T7/T3 run-off transcription vector (Promega AlterMax). The 'antisense' (T3) transcript is expected to hybridize to RNA products of positive sense genomic RNA; whereas, 'sense' (T7) transcript will hybridize to negative strand HCV genomic RNA products.

Interpretations, Pitfalls and Alternate Strategies:

We anticipate that the vmr11 probes will detect heterogeneous size viral genomic RNA (products of random fragmentation), with the accumulation of subgenomic RNA fragments at later times of HCV infection. In particular, small viral RNA (~22 nt vmr11), product of negative strand genomic RNA, is expected to accumulate late in viral infected cells. As is shown in FIG. 11C, peak accumulation of vmr11 RNA in vivo is observed at six days post-infection. It is likely however, that small RNAs (products of random fragmentation) will be detected in Northern blots, with both the 'sense; and 'antisense' 32p-labeled pre-vmr11 probes. To ascertain that the ~22 nt fragment is indeed a product of negative strand viral RNA, we will use BrU labeled nascent viral RNAs from HCV-infected cells, and identify vmr11 sequence by RNase-protection assay using $^{32}$P-labeled 'sense' pre-vmr11 probe (FIG. 11B), based on the procedure described before [89].

Next issue is whether the vmr11 "maturation" requires cleavage of viral genomic RNA by either the Dicer and/or RNase L endonucleases. In preliminary experiments we noted that vmr11 accumulation in HCV infected cells appear sensitive to RNase L knockdown, and relatively insensitive to Dicer knockdown (data not shown). Results suggest, but do not prove, that cleavage of viral genomic RNA with RNase L may precede vmr11 production; in this regard we note, that RNase L fragment svRNA6 [92] includes vmr 11 complementary sequence. We will examine the accumulation (or lack thereof), of vmr11 by Northern blots as described above, of RNA from HCV infected human hepatocytes without or with treatment with siRNA to knockdown RNase L (or Dicer). We note however, that even when the results show inhibition of vmr11 in cells following RNase L (and or Dicer) knockdown, it will only suggest the involvement of the endonucleases (at some stage of vmr11 processing), and not the mechanism of viral non-coding RNA processing. Nevertheless, the results would suggest possible 'feedback mechanism' involving innate antiviral defense (RNAse L activation ENREF 32 [93]), and vmr11 processing to promote viral oncogenesis.

Aim 2: RNA Parallel Duplex Structure (RNApds), and Functional Validation of Target mRNAs:

Our working hypothesis for this aim is that RNA parallel duplex formed between the trans-acting vmr11 and target mRNAs interferes with target mRNA translation and/or its stability. In either case, we would expect a decline in the protein products (of target mRNAs).

Preliminary Results Related to Aim 2:

(i) RNA Parallel Duplex Structure:

Double stranded DNA forms antiparallel right handed helical structure due to Watson and Crick [63] cis base pairing (cWC) between A and T and G and C.

In parallel duplex structure, directions of the two strands (5'→3') are in the same orientation and, bases A and T form trans Watson-Crick base pair (tWC). It might be difficult to form parallel duplex structure with three hydrogen bonded tWC base pair between G and C; a prediction validated by base-substitution mutants.

Based on the crystal structure of parallel double stranded structure of synthetic $(rA)_{11}$[62], we generated a RNA parallel duplex model for the CAUCAUC sequence of vmr11. In our model, the CAUCAUC forms parallel duplex in which A forms A:A Hoogsteen base pair (tHH) with two hydrogen bonds with the A in the other strand and also a base-phosphate hydrogen bond (FIG. 12A). The pyrimidine base C does not form any hydrogen bond with the corresponding C in the other strand. Instead both Cs stack with 3'A and each forms a hydrogen bond with one of the non-ester oxygen atoms of the phosphate of C in the other strand. Also, one of the C forms second hydrogen bond with one of the non-ester oxygen atoms of the 5'U in the other strand (FIG. 12A). Pyrimidine base U does not form hydrogen bond either with the corresponding U in the other strand, or with phosphate (as in case of C base). Since A forms tHH base pair, U bases move out and stack with the 3'A and the 5'C. The hydrogen bonds shown in FIGS. 2A and 2B are also observed in RNA crystal structure [PMID: 19528080, PMID: 19240142]. Our proposed CAUCAUC parallel duplex structure is shown in FIG. 12B.

(ii) Predicted mRNA Targets of Vmr11 (CUACUAC) May Form RNA Parallel Duplex (RNApds):

We searched for the CAUCAUC sequence in the mRNA of PTEN, HNF4alpha and TNPO2 and found one CAUCAUC sequence in PTEN and two sequences in HNF4alpha and TNPO2. Possible CAUCAUC parallel duplex formation sites within the coding and non-coding regions of target mRNAs are shown below.

Predicted mRNA Targets of Parallel Duplex Structures.

PTEN (Coding region: 1032-2243)
(SEQ ID NO: 4)
1039-CCAUCAUCAAA-1049

HNF4 alpha (Coding region: 118-1512)
(SEQ ID NO: 5)
1080-CCAUCAUCUUCUUU-1093

-continued (SEQ ID NO: 6)
2909-
CAUCAUCUCAUUUAAUCCUCCCUUCCUCCCUAUUAACCUA-2948

(3'-UTR)

TNPO2 (Coding region: 118-1512)
933-CAUCAUCCA-941

(SEQ ID NO: 7)
1106-ACAUCAUCCU-1115

Figure 13:
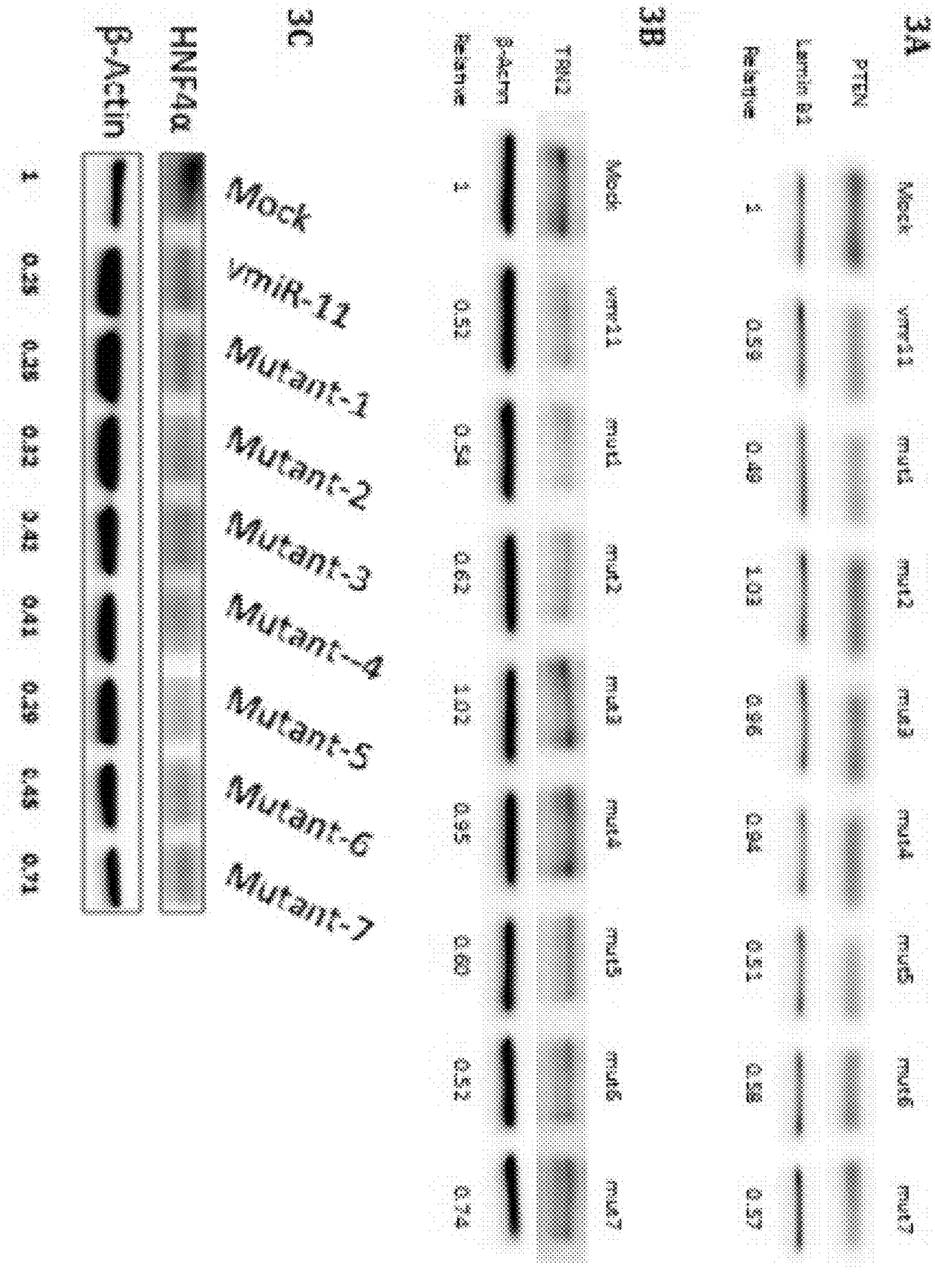
FIG. 13: Suppression of proteins of target mRNAs by vmr11 mutants. Relative values (Western blots) of Transportin-2 (A), PTEN (B) and HNF4a (C) proteins from human primary hepatocytes transfected with 50 nM of either the wt. or one of the vmr11 mutants, 48 hrs post-transfection. The Western blots were normalized to β-Actin loading control (A, and C), or Lamin-B1 (for nuclear PTEN, FIG. 13B). (results of three experiments).

(iii) Functional Validation of RNA Parallel Duplex Structures:

One prediction of the RNApds model is that parallel duplex structure with three hydrogen bonded tWC base pair between G and C will be difficult. We reasoned therefore that mutations of CAUCAUC sequence in vmr11 that involve G:C base pair will not form the RNA parallel duplex, or interfere with target mRNA translation. That is, base substitutions within (or near) CAUCAUC sequence of vmr11 that require G:C base-pair (Table 1, substitutions amongst the mutants are discerned from comparing each of the mutants with the ymiR-11 mimic) would not form RNApds; introduction of these mutants should restore target (mRNA) protein levels. We validated the prediction by comparing protein levels of target mRNAs in cells transfected with either the 'wild type' or the vmr11 mutants (FIG. 13).

TABLE 1

| vmiR-11 "mimic" and vmiR-11 mutants | |
|---|---|
| vmiR-11 mimic | 5'-**GUUCAUCAUCAUAUCCCAUGCC**-3' (SEQ ID NO: 1) |
| mutant 1 | 5'-CAU**CAUCAUCAUAUCCCAUGCC**-3' (SEQ ID NO: 8) |
| mutant 2 | 5'-**GUU**GUU**CAUCAUAUCCCAUGCC**-3' (SEQ ID NO: 9) |
| mutant 3 | 5'-**GUUCAU**GUU**CAUAUCCCAUGCC**-3' (SEQ ID NO: 10) |
| mutant 4 | 5'-**GUUCAUCA**AG**AUAUCCCAUGCC**-3' (SEQ ID NO: 11) |
| mutant 5 | 5'-**GUUCAUCAUC**C**CAUCCCAUGCC**-3' (SEQ ID NO: 12) |
| mutant 6 | 5'-**GUUCAUCAUCAU**C**CCCCAUGCC**-3' (SEQ ID NO: 13 |
| mutant 7 | 5'-**GUUCAUCAUCAUAUCCC**UA**GCC**-3' (SEQ ID NO: 14) |

TABLE 2

| vmiR-11 modifications | |
|---|---|
| NPR1: | 5'-GUUCAUCAUCAUAUCCC-3' (SEQ ID NO: 15) (deleted AUGCC from the 3' end of WT) |
| NPR2: | 5'-GUUCAUCAUCAUAU-3' (SEQ ID NO: 16) (deleted CCCAUGCC from the 3' end of WT) |

TABLE 2-continued

| vmiR-11 modifications | |
|---|---|
| NPR3: | 5'-GUUCUACUACAUAUCCCAUGCC-3' (SEQ ID NO: 17) (reversed the sequence from AUCAU to UACUA) |

AIM-2: Experimental Approach:

Results summarized above (FIG. 13) suggest that recognition of vmr11 target mRNAs: PTEN, TRN-2 and HNF4alpha engages central domain of vmr11, the CAUCAUC sequence, and the corresponding target mRNA sequence (Table 1), to form the RNA parallel duplex structure (FIG. 12). Lower inhibition of target proteins with vmr11 mutants, CA to GU (mutants 2 and 3, Table 2), or UC to AG (mutant 4), suggest lack of interference with target mRNA, perhaps due to the inability to form RNA parallel duplex and lack of inhibition of the target mRNA (FIG. 13).

The aim now is to determine: (i) whether the predicted RNApds target site(s) are recognized in vivo; and (ii) whether the RNA parallel duplex formation leads to target mRNA degradation (resulting in reduced protein levels); and (iii) the physiological context of trans-acting vmr11 and target mRNA interaction that allows the RNA parallel duplex formation. Results will support future studies to ask if specific protein(s) regulate the interactions of trans-acting vmr11 RNA and target mRNA, and/or the stability of RNApds.

(i) The Issue is What (Predicted) Site(s) of the Target mRNAs are Recognized by Transacting Vmr11 to Form the RNA Parallel Duplex?

Figure 14:
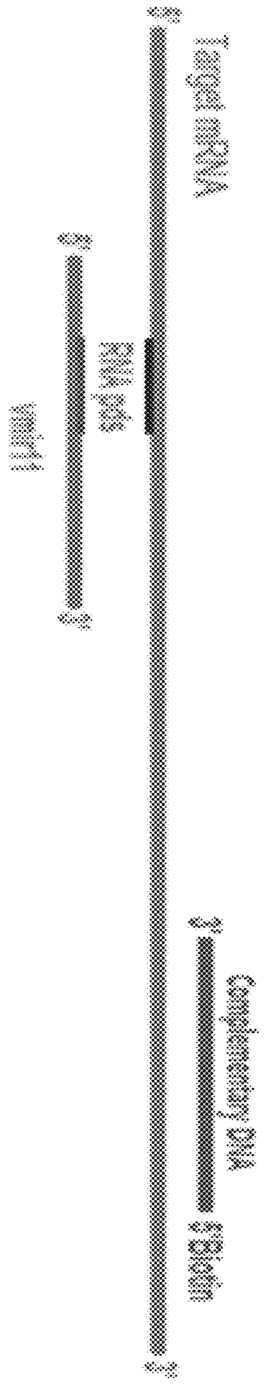
FIG. 14: Schematic representation of three steps of target mRNA recognition: (i) In the first step we will hybridize in vivo formed target mRNA and vmr11 (CAUCAUC) complex to biotinylated DNA oligomers complementary to each of the five predicted targets (downstream of projected RNApds), and fractionate it on streptavidin column. Next step (ii) will be to release the RNApds by RNAse H (cuts RNA of RNA-DNA hybrid). Finally, step (iii) the components of purified RNApds will be quantitated by qRT-PCR (BrU does not interfere with RT-PCR[33]).

BrU pulse labeled RNA from control or HCV infected cells will be purified at sequential time points. The in vivo BrU RNA will be immune fractionated by BrdU-antibody column as described in Aim1. To fractionate target mRNA-vmr11 complex (FIG. 14), we will hybridize target mRNA to 5'-biotinylated synthetic DNA oligonucleotides complementary to the target mRNA (sequence shown in Table 1). The biotinylated DNA oligomer will be designed to complementary with the target mRNA, 50 nucleotides downstream of each predicted site of the mRNA targets.

Three steps of target mRNA recognition are (FIG. 14): (a) In the first step we will hybridize in vivo formed target mRNA and vmr11 (CAUCAUC) complex to biotinylated DNA oligomers complementary to each of the five predicted targets (downstream of projected RNApds), and fractionate it on streptavidin column. Next step (b) will be to release the RNApds by RNAse H (cuts RNA of RNA-DNA hybrid). Finally, step (c) the components of purified RNApds will be quantitated by qRT-PCR (BrU does not interfere with RT-PCR [94]). We will design specific primers to detect the five predicted RNApds target sites within the three mRNA targets of vmr11 (shown in Table 1). RT-PCR products are expected to show equimolar amounts of vmr11 and the target mRNA sequences, (if in fact RNA pds is formed equally efficiently at all predicted sites).

To determine the sequence of mRNA targets engaged in forming the RNA parallel duplex in vivo, we will design the RT-PCR primers to include cloning sites flanking the PCR fragments for DNA sequencing.

(ii) Target mRNA Stability:

We will perform qRT-PCR analysis of the target mRNAs in cells transfected with either the wild type or mutant vmr111 as described in FIG. 13. Changes in the levels of target mRNAs may parallel the observed decline in protein levels in response to vmr11 mutants (FIG. 13), suggesting that lower amount of target mRNA is principally responsible for the reduced protein levels. Alternatively, if there is little or no change in mRNA levels (of PTEN, TRN-2 or HNF4alpha) in cells transfected with the vmr11 mutants (yet there is marked decline in their protein products), the results would suggest a translational inhibition of target mRNAs as a result of RNA parallel duplex formation.

(iii) Next Issue is Whether Protein(s) Associate with or Modulate RNA Parallel Duplex Formation:

To address the question we will fractionate lysate of BrU pulse labeled (HCV-infected and control) cells on biotinylated DNA oligonucleotides (complementary to target mRNA, as described above); release the RNA-protein complex from streptavidin column (by RNAse H) and identify the protein components of the RNApds by Mass Spectrometry (our Proteomics core). The approach requires important control, that is, to be able to complete vmr11-mRNA target recognition in vivo with vmr11 mutant oligonucleotides. In preliminary studies we observed that vmr11 mediated inhibition of PTEN or TRN-2, can be rescued by dominant negative vmr11 mutants, in HCV infected cells that compete with vmr11 in vivo (data not shown). RNA parallel duplex associated proteins will be validated by comparing the RNA pds-bound proteins from HCV infected cells without or with transfection of vmr11 transdominant mutant oligonucleotides.

Direct Assay of Vmr11, (CAUCAUC Sequence) Binding Protein:

We will design 5'-Biotinylated oligomers (with 22 nt 'hinge sequence' to the three vmr11 probes (shown as NPR1-3, Table 2), and affinity fractionate proteins from HCV infected or control hepatocytes, and compare the proteins bound to NPR1 (wild type) and the two mutants (NPR2 and NPR3) to identify proteins that specifically associate with the RNA parallel duplex structures. Contrasting the proteins associated with wt (NPR1) to the mutant (NPR3, Table 2; where the CAUCAUC sequence has been revered), will indicate their specific association with RNApds structure.

Example 4: Preparation of 3 Random-Primed cDNA Libraries and 3 cDNA Libraries from Small RNA for Illumina Sequencing, and Successful Sequencing of VMIR11 from Human Hepatocytes Infected with HCV Three total RNA samples from *Homo sapiens*, as described in Table 4, delivered on dry ice.

TABLE 4

Description of RNA samples.

| No. | Sample | Conc. (ng/μl) | Vol. (μl) | Conc. (ng/μl) | Total amount (μg) | Ratio 28S/18S |
|---|---|---|---|---|---|---|
| | | customer-specified | | own measurement (see FIG. 1) | | |
| 1 | c-PPH | 1.600 | 30 | 1.951 | 56.6 | 2.3 |
| 2 | H77-D2 | 2.000 | 30 | 1.533 | 44.5 | 2.3 |
| 3 | H77-D4 | 2.000 | 30 | 2.443 | 70.9 | 2.4 |

Analysis of Total RNA

Figure 15:
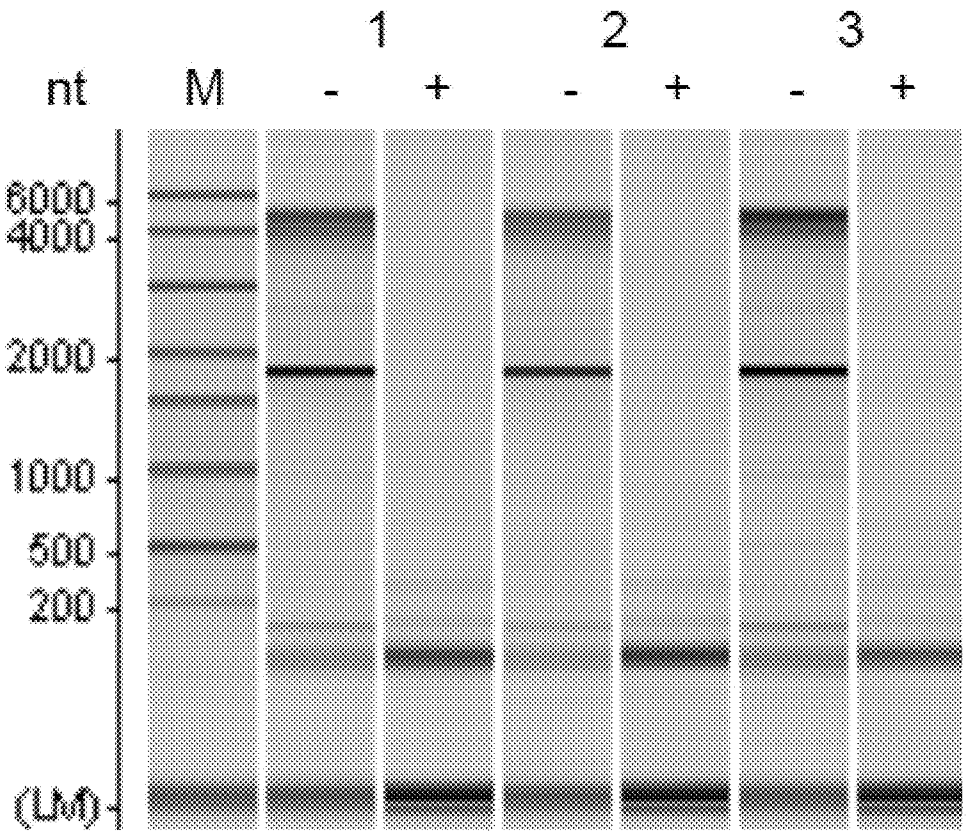
FIG. 15: Analysis of the RNA samples before (−) and after rRNA depletion (+) on a Shimadzu MultiNA microchip electrophoresis system. M=RNA marker.

The total RNA samples were examined by capillary electrophoresis (FIG. 15).

rRNA Depletion

From the total RNA samples, ribosomal RNA molecules were depleted using Ribo-Zero rRNA Removal Kit (Human/Rat/Mouse, Epicentre). The electrophoresis images are shown in FIG. 15. After rRNA depletion, the three RNA samples were separated into large (>200 nt) and small (<200 nt) RNA fractions.

cDNA Synthesis: Random-Primed cDNA Libraries

Figure 16:
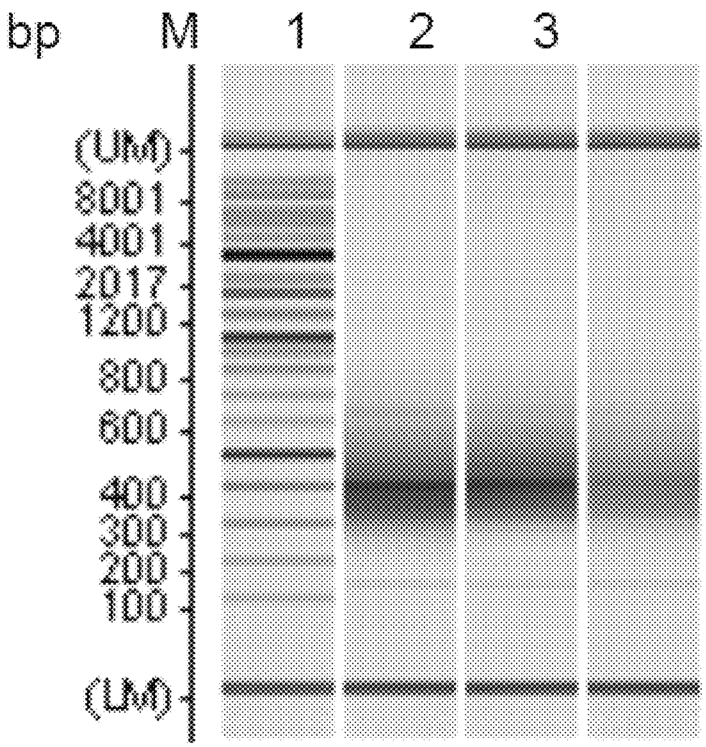
FIG. 16: Analysis of the PCR-amplified random-primed cDNA samples on a Shimadzu MultiNA microchip electrophoresis system. M=100 bp ladder

The large RNA fractions were fragmented with ultrasound (2 pulses of 30 sec at 4° C.). First-strand cDNA synthesis was primed with a N6 randomized primer. Then, the Illumina TruSeq sequencing adapters were ligated to the 5' and 3' ends of the cDNA. The cDNA was finally amplified with PCR using a proof reading enzyme. The number of cycles and the TruSeq barcode sequences which are part of the 3' TruSeq sequencing adapters are included in Table 5. The cDNA was purified using the Agencourt AMPure XP kit (Beckman Coulter Genomics) and was analyzed by capillary electrophoresis (FIG. 16).

TABLE 5

Properties of the random-primed cDNA samples

| No. | Sample (random) | Barcode | PCR cycles |
|---|---|---|---|
| 1 | c-PPH | CGATGT | 17 |
| 2 | H77-D2 | CAGATC | 17 |
| 3 | H77-D4 | GTGAAA | 17 |

C-PPH=control uninfected human hepatocytes; H-77D2=HCV infected 24 hours; H-77D4=HCV infected 48 hours.

cDNA Libraries from Small RNA

Figure 18:
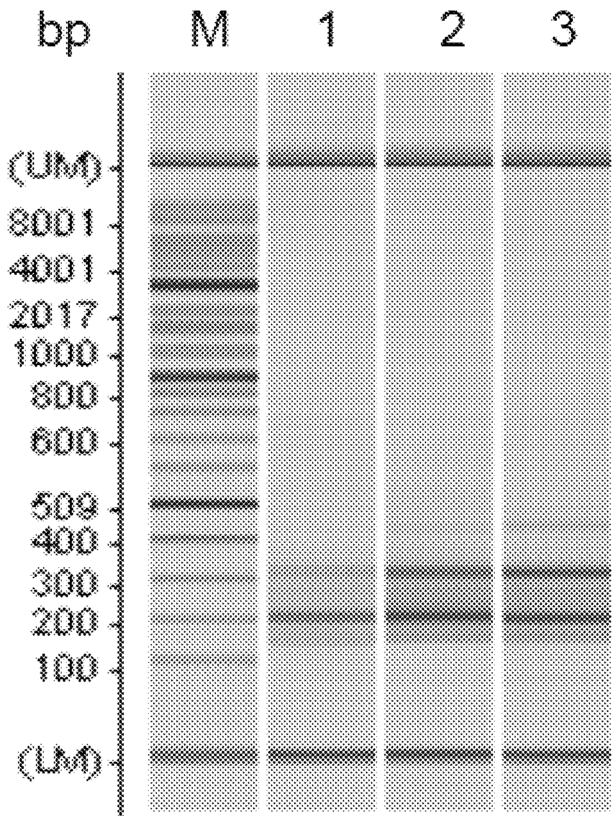
FIG. 18: Analysis of the PCR-amplified cDNA samples from small RNA on a Shimadzu MultiNA microchip electrophoresis system. M=100 bp ladder

First, the rRNA depleted small RNA fractions were poly (A)-tailed using poly(A) polymerase. Then, CAP and 5'PPP structures were removed using tobacco acid pyrophosphatase (TAP). Afterwards, an RNA adapter was ligated to the 5'-monophosphate of the RNA. First-strand cDNA synthesis was performed using an oligo(dT)-adapter primer and the M-MLV reverse transcriptase. The resulting cDNAs were PCR-amplified using a high fidelity DNA polymerase. PCR cycles performed and barcode sequences, which are part of the 3' sequencing adapter, are included in Table 6. The cDNAs were purified using the Agencourt AMPure XP kit (Beckman Coulter Genomics) and were analyzed by capillary electrophoresis (FIG. 18).

TABLE 6

Properties of the cDNA samples from small RNA

| No. | Sample (small RNA) | Barcode | PCR cycles |
|---|---|---|---|
| 1 | c-PPH | ACAGTG | 26 |
| 2 | H77-D2 | GCCAAT | 21 |
| 3 | H77-D4 | ATGTCA | 20 |

Pool Formation and Size Fractionation

Figure 17:
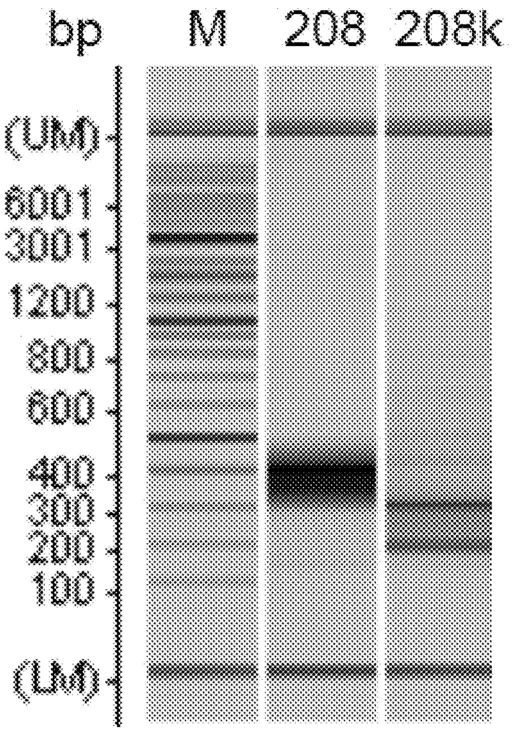
FIG. 17: Analysis of the size fractionated cDNA pool 208 (random) and pool 208 k (small RNA) on a Shimadzu MultiNA microchip electrophoresis system. M=100 bp ladder.

For Illumina sequencing, the random-primed cDNA samples were pooled in pool 208 (random) and the cDNA samples from small RNA were pooled in pool 208 k (small RNA) in approximately equimolar amounts, respectively. The cDNA pool 208 (random) was size fractionated in the size range of 300-500 bp on a preparative agarose gel. The cDNA pool 208 k (small RNA) was size fractionated in the size range of 180-600 bp using a differential clean-up with the Agencourt AMPure kit. Aliquots of the size fractionated cDNA pools were analyzed by capillary electrophoresis (FIG. 17). The properties of the pools are indicated in Table 7.

TABLE 7

| Concentrations and volumes of cDNA pools. | | |
|---|---|---|
| Pool | 208 random | 208k small RNA |
| Conc. (ng/μl) | 17.8 | 14.0 |
| Volume (μl) | 18.0 | 18.0 |

Description of cDNA Samples

The random-primed cDNAs have a size range of 300-500 bp. The cDNAs from small RNA have a size range of 180-600 bp. The primers used for PCR amplification were designed for TruSeq sequencing according to the instructions of Illumina.

The following adapter sequences flank the DNA insert:

```
TrueSeq_Sense_primer
                                        (SEQ ID NO: 18)
5'AATGATACGGCGACCACCGAGATCTACACTCTTTCCCTACACGA

CGCTCTTCCGATCT-3'

TrueSeq_Antisense_NNNNNN_primer Barcode
                                        (SEQ ID NO: 19)
5'-CAAGCAGAAGACGGCATACGAGAT-NNNNNN-

GTGACTGGAGTTCAGACGTGTGCTCTTCCGATCT-3'.
```

The total length of the flanking sequences is 122 bp.

The cDNA libraries prepared from small RNA (Pool 208 k) carry an additional poly(T) tail of 25 nucleotides at the 3' end of the antisense primer. Thus, the length of the flanking sequences is increased to 147 bp.

Detection of Viral Induced miRNA (VmiR) Produced from the Opposite Strand of the HCV Genome.

The project needed a hybrid human/HCV genome and transcriptome. This was created from the existing human GRCh38 genome download and HCV genotype 1a (most prevalent in the US, most difficult to treat). (Genbank sequence M62321).

Our pipeline uses the mirDeep* programs which requires ancillary data files (including a gff file featuring the chromosomal coordinates of microRNAs) in order to derive known miRNA levels and to detect new miRNA.

A customized miRDeep* database was created with the following entries:

```
>hcv-miR-vmr45 Hepatitis C virus vmr45
CGCCCAAAUCUCCAGGCAUUGA       (SEQ ID NO: 20)

>hcv-miR-vmr46 Hepatitis C virus vmr46
GACACUCAUACUAACGCCAUGGCUA    (SEQ ID NO: 21)

>hcv-miR-vmr43 Hepatitis C virus vmr43
AGACAGGAGCCAUCCCGCCCAC       (SEQ ID NO: 22)

>hcv-miR-vmr41 Hepatitis C virus vmr41
CGCCCAGUUCCCCACCAUGGAG       (SEQ ID NO: 23)

>hcv-miR-vmr39 Hepatitis C virus vmr39
GGCCAGCCCACAAGGUCUUGGU       (SEQ ID NO: 24)

>hcv-miR-vmr20 Hepatitis C virus vmr20
ACAUGCAUGUCAUGAUGUAUUU       (SEQ ID NO: 25)
```

-continued

```
>hcv-miR-vmr11 Hepatitis C virus vmr11
GUUCAUCAUCAUAUCCCAUGCC       (SEQ ID NO: 26)

>hcv-miR-vmr19 Hepatitis C virus vmr19
GGAGCUGGCCAUAGAAGGGGGU       (SEQ ID NO: 27)

>hcv-miR-vmr61 Hepatitis C virus vmr61
GUACACAAUACUCGAGUUAGGG       (SEQ ID NO: 28)

>hcv-miR-vmr57 Hepatitis C virus vmr57
CUUGCCGUAGGUGGAGUACGUG       (SEQ ID NO: 29)

>hcv-miR-vmr44 Hepatitis C virus vmr44
UCGAGGUUGCGACCGCUCGGAA       (SEQ ID NO: 30)

>hcv-miR-vmr49 Hepatitis C virus vmr49
UGACCCGUCGCUGAGAUCCGGA       (SEQ ID NO: 31)

>hcv-miR-vmr48 Hepatitis C virus vmr48
GGGGGGGGCGGAGUACCUGGUC       (SEQ ID NO: 32)
```

The small RNA libraries from samples c-PPH, H77-D2 and H77-D4 were mapped to the hybrid human/HCV genome using either miRDeep* or Bowtie.

miRDeep* run with default parameters successfully mapped human-derived RNA to known human miRNA. The 10 most abundant human miRNA in each of the 3 samples are shown below:

c-PPH Sample:
hsa-mir-21 chr17+111318
hsa-let-7c chr21+91872
hsa-let-7b chr22+48641
hsa-mir-23a chr19−39836
hsa-mir-23b chr9+11945
hsa-mir-221 chrX−9381
hsa-mir-199b chr9−9348
hsa-mir-10a chr17−5646
hsa-let-7e chr19+5459

H77-D2 Sample:
hsa-mir-21 chr17+356501
hsa-let-7c chr21+288432
hsa-let-7b chr22+118282
hsa-mir-23a chr19−111225
hsa-mir-23b chr9+23082
hsa-let-7e chr19+13788
hsa-let-7d chr9+7481
hsa-mir-221 chrX−6675
hsa-mir-183 chr7−5876
hsa-let-7i chr12+5016

H77-D4 Sample:
hsa-mir-21 chr17+1517413
hsa-mir-23a chr19−423251
hsa-let-7c chr21+404649
hsa-let-7b chr22+171354
hsa-mir-23b chr9+76950
hsa-let-7e chr19+21964
hsa-let-7d chr9+14873
hsa-mir-10a chr17−11561
hsa-mir-221 chrX−10623
hsa-mir-183 chr7−10618

Figure 19:
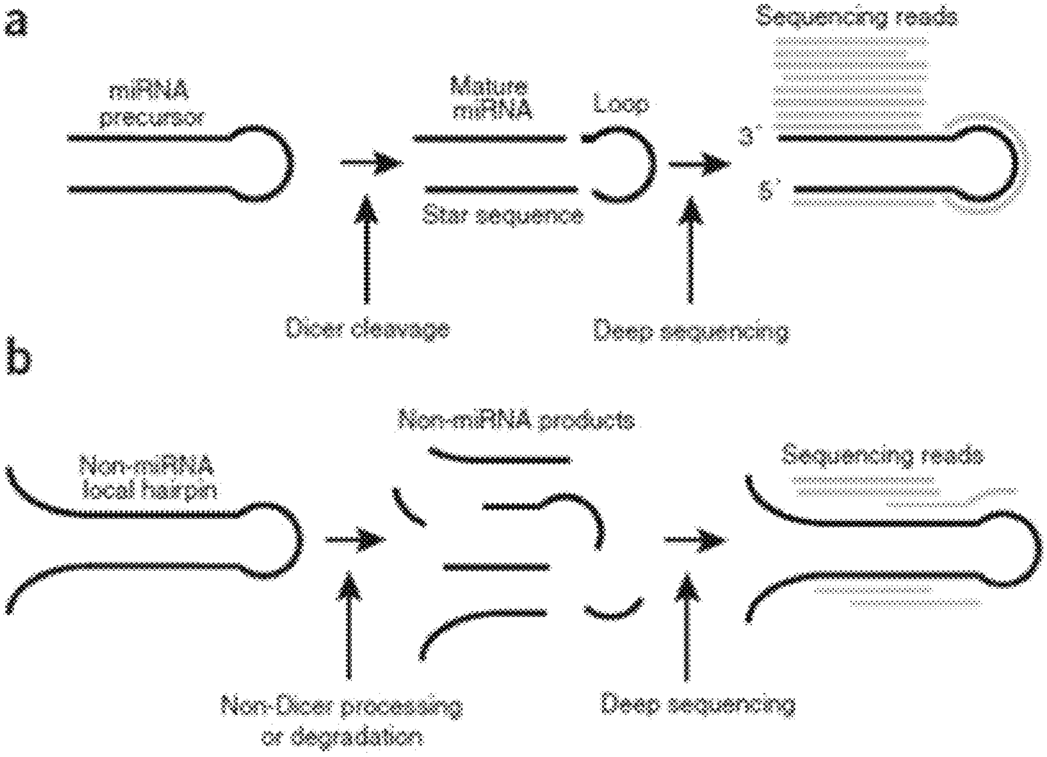
FIG. 19: Schematic illustrating miRDeep* rational. miRdeep* tells apart between reads belonging to a bona-fide miRNA (A) from artifact short reads mapping (B).

There is consistency between these 3 samples w.r.t their human miRNA content.

miRDeep* implements both a read-mapper and an inference process that allows to return quantitative and confidence values. The scheme shown in FIG. 19 illustrates miRDeep* rational. miRdeep* tells apart between reads belonging to a bona-fide miRNA (FIG. 19*a*) from artifact short reads mapping (FIG. 19*b*).

Exhaustive combinations of miRDeep* parameters were applied in the scope to identify and quantify potential HCV miRNA events. However, this approach did not return any result. We turn to the short read mapper Bowtie with some trained parameters and were able to both detect and quantify Vmir11 and a potentially new HCV miRNA.

Figure 20:
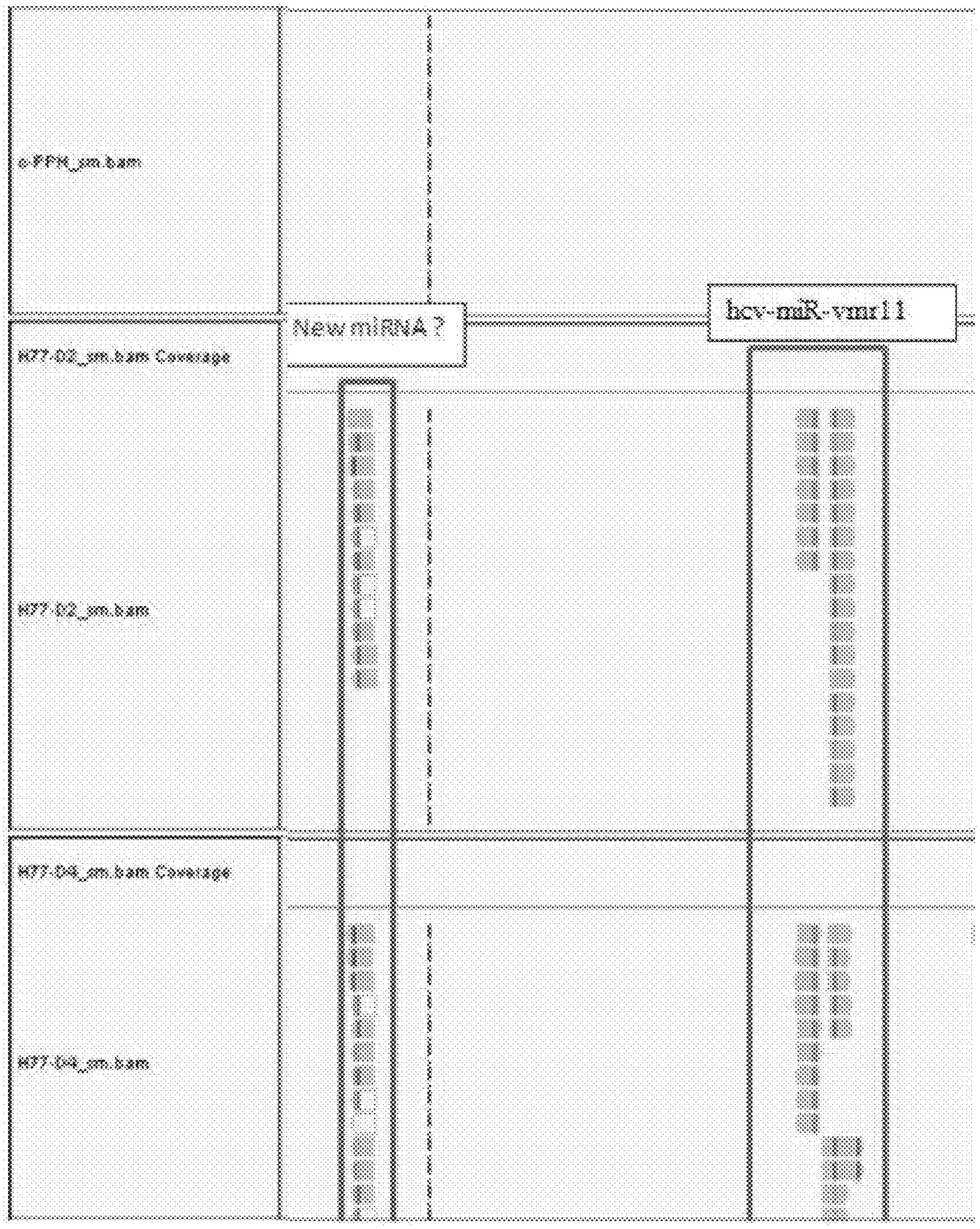
FIG. 20: Detection of HCV-miR-vmr11 in samples H77-D2 and H77-D4.
Figure 21:
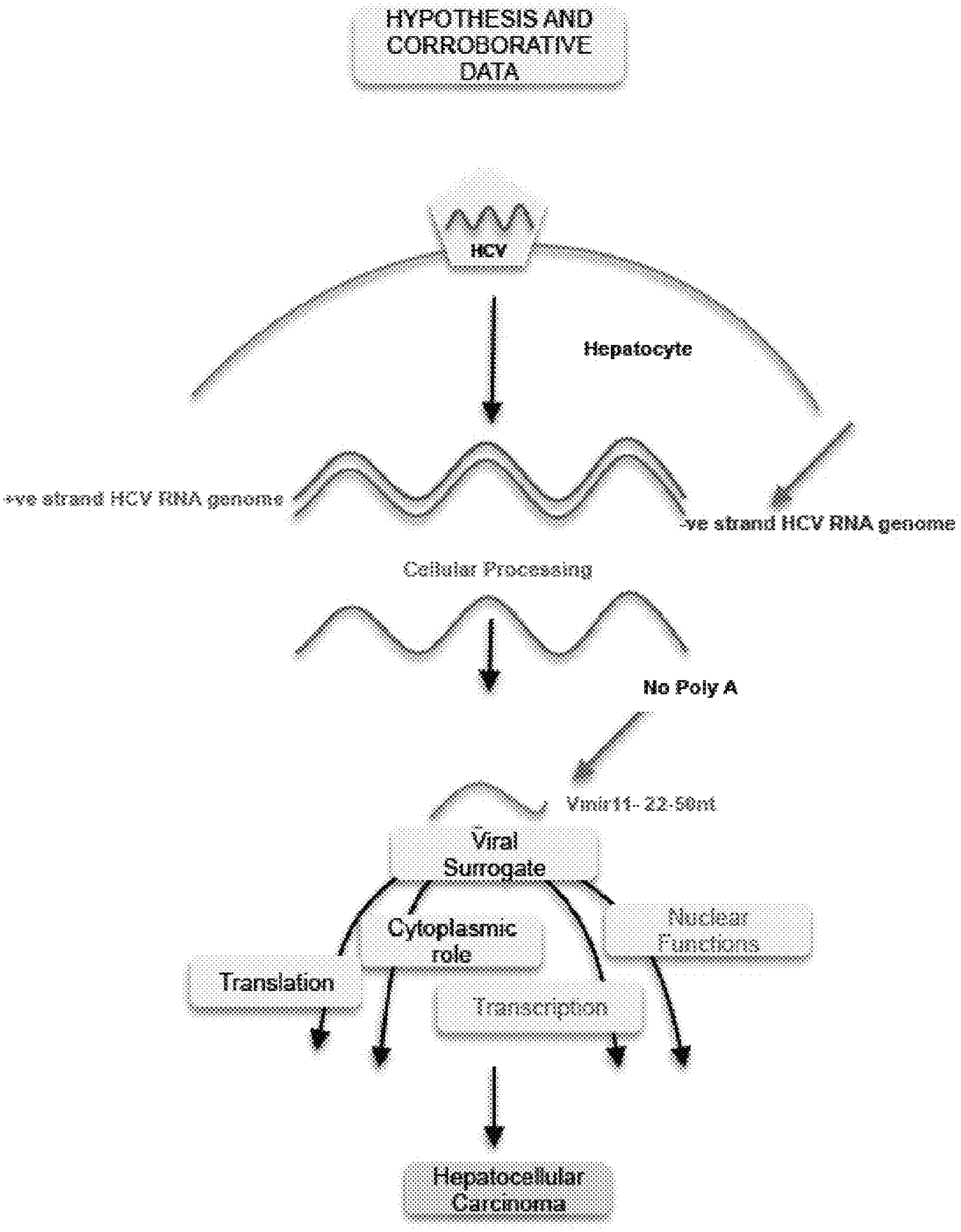
FIG. 21: Illustration of a putative mechanism for HCV driven hepatocellular carcinoma, and a non-limiting illustration of a sequencing method for sequencing vmr11.
Figure 21:
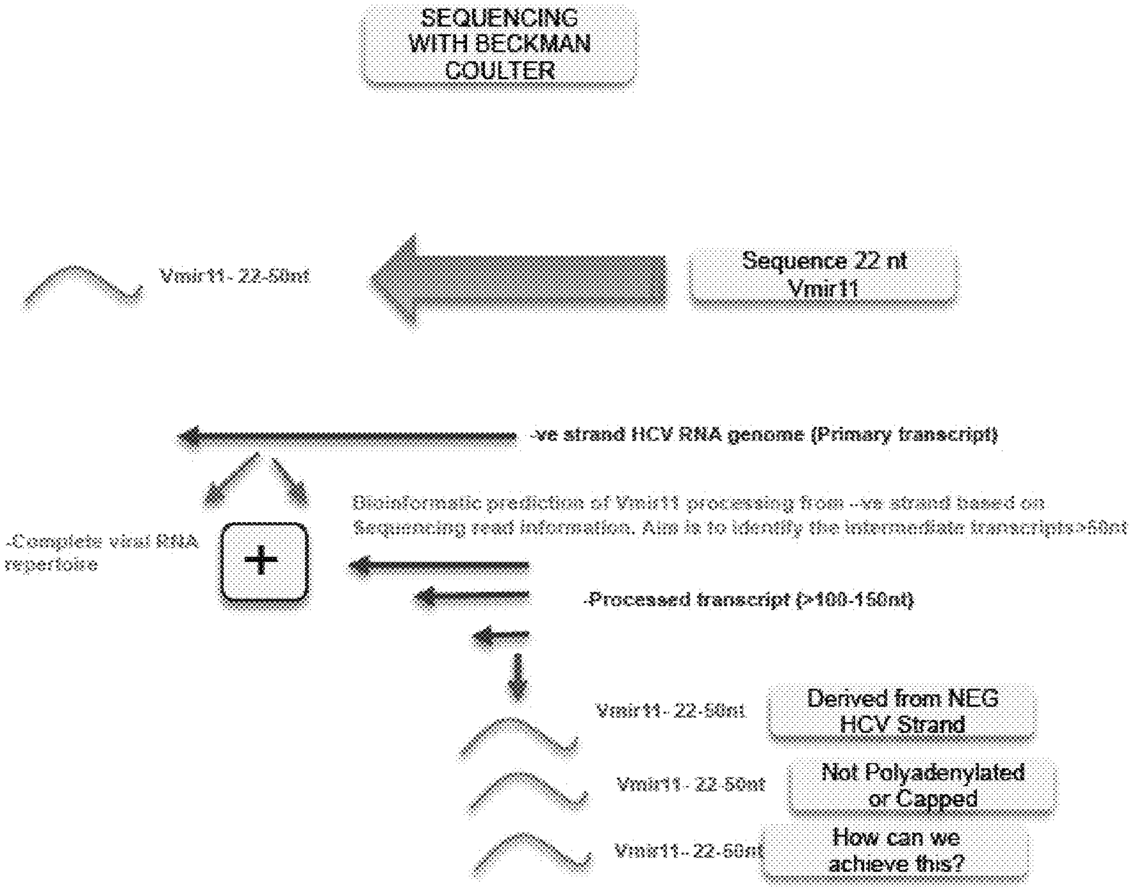
Figure 23:
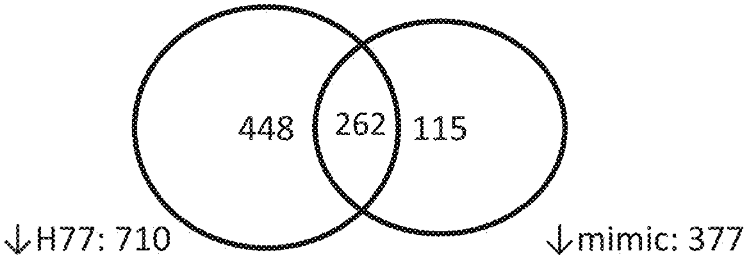
FIG. 23: Gene expression changes in human hepatocytes transfected with vmr11 'mimic' are largely similar to those in HCV infected cells. (A) Down-regulated genes. (B) Up-regulated genes.
Figure 23:
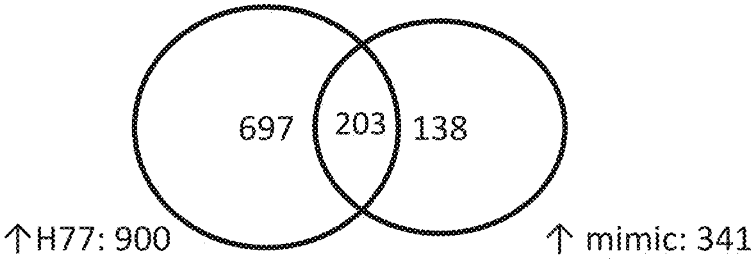

While undetectable in the c-PPh sample, the hcv-vmr11 was significantly observed in both H77-D2 and H77-D4 (FIG. 20). In both H77-D2 and H77-D4, reads mapping to hcv-miR-vmr11 accounted ~1% of the whole set of viral short RNA. There are slightly longer reads mapping to the hcv-miR-vmr11. In addition, the fact that we were able to identify hcv-miR-vmr11 with Bowties and not with miRDeep* suggests that the hcv-miR-vmr11 pre miRNA molecule differs in structure from the mammals and specifically human premature miRNA molecules Example 5: Restriction of Nuclear PTEN in HCV-Infected Hepatocytes To predict small viral RNA sequences from HCV genomic RNAs, we filtered the genomic sequences on the basis of the following criteria: 1) It must form a stable hairpin-loop structure; 2) The hairpin-loop structure must be conserved across HCV strains, possibly by compensatory mutations that preserve the base-pairings; and 3) the sequence of the mature vmr within the hairpin must also be conserved, to retain the ability to bind to its target. We downloaded from GenBank complete HCV1a genomic sequences and divided one of the sequences (NC_004102), deemed reference, into 70-100 bp sequence fragments with 20 bp shift (overlap) (FIG. 22). Each fragment was then analyzed using the program RNAfold to seek stable hairpin-loop structures that could be suitable substrates for processing small RNAs by host cell nucleases. All selected hairpins were cross-compared with the remaining HCV genomic sequences for conservation of the sequence and secondary structures. Eventually, thirteen candidate viral microRNAs (vmr) (Table 8) were selected for further study, some of which were validated with RT-PCR (FIG. 23).

TABLE 8

Thirteen candidate vmr sequences were derived from the HCV1a negative sense genomic RNA. The vmr sequences and their location (indicated on the 9,646 bp negative strand HCV genomic RNA) are shown. (S: Overall sequence conservation; R: Hairpin conservation; RSS: Combined structure and seed sequence conservation. The nucleotide sequences of the following vmr IDs are represented by SEQ ID NO: 33 to SEQ ID NO: 45 in descending order with SEQ ID NO: 33 representing vmr45 at the top of the table and SEQ ID NO: 45 represents vmr48 at the bottom of the table.

| ID | Class | vsRNAs sequence | position |
|---|---|---|---|
| vmr45 | S | CGCCCAAATCTCCAGGCATTGA | 9414-9435 |
| vmr46 | S | GACACTCATACTAACG CCATGGCTA | 9543-9567 |
| vmr43 | S | AGACAGGAGCCATCCCGCCCAC | 9009-9030 |
| vmr41 | S | CGCCCAGTTCCCCACCATGGAG | 8199-8220 |
| vmr39 | R | GGCCAGCCCACAAGGTCTTGGT | 5971-5992 |
| vmr20 | R, RSS | ACATGCATGTCATGATGTATTT | 4358-4379 |
| vmr11 | R, RSS | GTTCATCATCATATCCCATGCC | 8331-8352 |
| vmr19 | R, RSS | GGAGCTGGCCATAGAAGGGGGT | 2703-2724 |

TABLE 8-continued

Thirteen candidate vmr sequences were derived from the HCV1a negative sense genomic RNA. The vmr sequences and their location (indicated on the 9,646 bp negative strand HCV genomic RNA) are shown. (S: Overall sequence conservation; R: Hairpin conservation; RSS: Combined structure and seed sequence conservation. The nucleotide sequences of the following vmr IDs are represented by SEQ ID NO: 33 to SEQ ID NO: 45 in descending order with SEQ ID NO: 33 representing vmr45 at the top of the table and SEQ ID NO: 45 represents vmr48 at the bottom of the table.

| ID | Class | vsRNAs sequence | position |
|---|---|---|---|
| vmr61 | R | GTACACAATACTCGAGTTAGGG | 8664-8685 |
| vmr57 | RSS | CTTGCCGTAGGTGGAGTACGTG | 5412-5433 |
| vmr44 | RSS | TCGAGGTTGCGACCGCTCGGAA | 9129-9150 |
| vmr49 | RSS | TGACCCGTCGCTGAGATCCGGA | 2094-2115 |
| vmr48 | RSS | GGGGGGGGCGGAGTACCTGGTC | 0996-1017 |

TABLE 9

Putative vmr11 targets among down-regulated genes in HCV infected (H77) and vmr11 transfected 'mimic' hepatocytes, predicted by PITA (score cutoff −10.0.)

| RefSeq Accession | PITA score | Function |
|---|---|---|
| Genes down-regulated in H77: | | |
| NM_000457.4 | −19.30 | Hepatocyte nuclear factor 4, alpha (HNF4A), transcript variant 2, mRNA |
| NM_002103.4 | −14.63 | Glycogen synthase 1 (muscle) (GYS1), transcript variant 1, mRNA |
| NM_145892.2 | −14.17 | Ataxin 2-binding protein 1 (A2BP1), transcript variant 2, mRNA |
| NM_006755.1 | −13.04 | Transaldolase 1 (TALDO1), mRNA |
| NM_001099439.1 | −12.31 | EPH receptor A10 (EPHA10), transcript variant 3, mRNA |
| NM_025152.2 | −12.16 | Nucleotide binding protein-like (NUBPL), mRNA |
| NM_205863.2 | −12.07 | Par-3 partitioning defective 3 homolog B (*C. elegans*) (PARD3B), transcript variant a, mRNA |
| NM_013433.4 | −11.85 | Transportin 2 (TNPO2), transcript variant 2, mRNA |
| NM_133458.2 | −11.34 | Zinc finger protein 90 homolog (mouse) (ZFP90), mRNA |
| NM_022336.3 | −10.96 | Ectodysplasin A receptor (EDAR), mRNA |
| NM_000728.3 | −10.76 | Calcitonin-related polypeptide beta (CALCB), mRNA |
| NM_006537.2 | −10.67 | Ubiquitin specific peptidase 3 (USP3), mRNA |
| NM_020927.1 | −10.60 | Vesicle amine transport protein 1 homolog (*T. californica*)-like (VAT1L), mRNA |
| NM_001142523.1 | −10.47 | Interleukin-1 receptor-associated kinase 3 (IRAK3), transcript variant 2, mRNA |
| NM_000872.4 | −10.06 | 5-hydroxytryptamine (serotonin) receptor 7 (adenylate cyclase-coupled) (HTR7), transcript variant a, mRNA |
| Genes down-regulated in 'mimic' | | |
| NM_000457.3 | −19.30 | Hepatocyte nuclear factor 4, alpha (HNF4A), transcript variant 2, mRNA |
| NM_002103.4 | −14.63 | Glycogen synthase 1 (muscle) (GYS1), transcript variant 1, mRNA |

TABLE 9-continued

Putative vmr11 targets among down-regulated genes in HCV infected (H77) and vmr11 transfected 'mimic' hepatocytes, predicted by PITA (score cutoff −10.0.)

| RefSeq Accession | PITA score | Function |
|---|---|---|
| NM_002923.3 | −13.63 | Regulator of G-protein signaling 2, 24 kDa (RGS2), mRNA |
| NM_005079.2 | −12.49 | Tumor protein D52 (TPD52), transcript variant 3, mRNA |
| NM_001002231.1 | −12.46 | Kallikrein-related peptidase 2 (KLK2), transcript variant 2, mRNA |
| NM_001099439.1 | −12.31 | EPH receptor A10 (EPHA10), transcript variant 3, mRNA |
| NM_205863.2 | −12.07 | Par-3 partitioning defective 3 homolog B (*C. elegans*) (PARD3B), transcript variant a, mRNA |
| NM_013433.4 | −11.85 | Transportin 2 (TNPO2), transcript variant 2, mRNA |
| NM_133458.2 | −11.34 | Zinc finger protein 90 homolog (mouse) (ZFP90), mRNA |
| NM_001039937.1 | −11.08 | Integrator complex subunit 6 (INTS6), transcript variant 2, mRNA |
| NM_020927.1 | −10.60 | Vesicle amine transport protein 1 homolog (*T. californica*)-like (VAT1L), mRNA |

Computational Prediction of Vmr11 Binding Sites on TRN-2 3'U1R.

Figure 24:
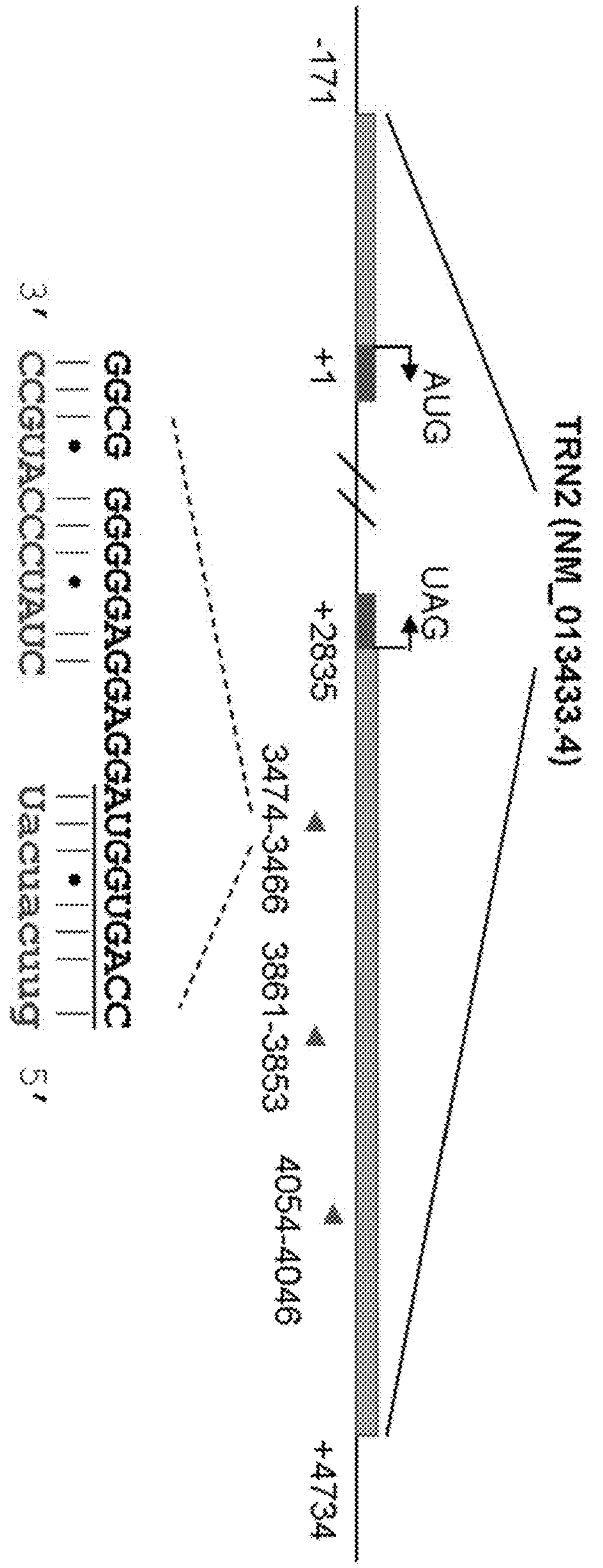
FIG. 24: Predicted vmr11 binding sites on the TRN-2 3'UTR. PITA revealed eight possible binding sites, of which the strongest is located at 3474-3466 with the UTR. Vmr11 sequence is the lower half of the double-strand sequence, with the seed region in lowercase letters, and the PITA-predicted binding site anchor is underlined. The top nucleotide sequence is represented by SEQ ID NO:52, and the bottom nucleotide sequence is represented by SEQ ID NO:53.

Most microRNA target prediction programs use conservation of the putative target site in other species to narrow down candidates, but this requirement is not to be expected in our case, where the HCV infection may be restricted to human. In contrast, the protram PITA takes into account the thermodynamics of the microRNA-mRNA hybrid as well as the target site accessibility determined by base-pairs interactions within the mRNA to predict target sites, and therefore is particularly well suited for our application. Using PITA, we identified eight putative targets of vmr11 along the TRN-2'UTR, of which the strongest is located in the 3474-3466 region (FIG. 24).

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

1. Planchon S M, Waite K A, Eng C: The nuclear affairs of PTEN. *J Cell Sci* 2008, 121 (Pt 3):249-253.
2. Baker S J: PTEN enters the nuclear age. *Cell* 2007, 128(1):25-28.
3. Leslie N R, Foti M: Non-genomic loss of PTEN function in cancer: not in my genes. *Trends Pharmacol Sci* 2011, 32(3): 131-140.
4. Chang C J, Mulholland D J, Valamehr B, Mosessian S, Sellers W R, Wu H: PTEN nuclear localization is regulated by oxidative stress and mediates p53-dependent tumor suppression. *Molecular and cellular biology* 2008, 28(10):3281-3289.
5. Eng C: PTEN: one gene, many syndromes. *Hum Mutat* 2003, 22(3):183-198.
6. Peyrou M, Bourgoin L, Foti M: PTEN in liver diseases and cancer. *World journal of gastroenterology: WJG* 2010, 16(37):4627-4633.
7. Clement S, Peyrou M, Sanchez-Pareja A, Bourgoin L, Ramadori P, Suter D, Vinciguerra M, Guilloux K, Pascarella S, Rubbia-Brandt L et al: Down-regulation of phosphatase and tensin homolog by hepatitis C virus core 3a in hepatocytes triggers the formation of large lipid droplets. *Hepatology* 2011, 54(1):38-49.
8. Shen W H, Balajee A S, Wang J, Wu H, Eng C, Pandolfi P P, Yin Y: Essential role for nuclear PTEN in maintaining chromosomal integrity. *Cell* 2007, 128(1):157-170.
9. Puc J, Parsons R: PTEN loss inhibits CHK1 to cause double stranded-DNA breaks in cells. *Cell Cycle* 2005, 4(7):927-929.
10. Tachibana M, Shibakita M, Ohno S, Kinugasa S, Yoshimura H, Ueda S, Fujii T, Rahman M A, Dhar D K, Nagasue N: Expression and prognostic significance of PTEN product protein in patients with esophageal squamous cell carcinoma. *Cancer* 2002, 94(7):1955-1960.
11. Zhou X P, Gimm O, Hampel H, Niemann T, Walker M J, Eng C: Epigenetic PTEN silencing in malignant melanomas without PTEN mutation. *The American journal of pathology* 2000, 157(4):1123-1128.
12. Zhou X P, Loukola A, Salovaara R, Nystrom-Lahti M, Peltomaki P, de la Chapelle A, Aaltonen L A, Eng C: PTEN mutational spectra, expression levels, and subcellular localization in microsatellite stable and unstable colorectal cancers. *The American journal of pathology* 2002, 161(2):439-447.
13. Banaudha K, Orenstein J M, Korolnek T, St Laurent G C, 3rd, Wakita T, Kumar A: Primary hepatocyte culture supports hepatitis C virus replication: a model for infection-associated hepatocarcinogenesis. *Hepatology* 2010, 51(6):1922-1932.
14. Banaudha K, Kaliszewski M, Korolnek T, Florea L, Yeung M L, Jeang K T, Kumar A: MicroRNA silencing of tumor suppressor DLC-1 promotes efficient hepatitis C virus replication in primary human hepatocytes. *Hepatology* 2011, 53(1):53-61.
15. Kanehisa M, Goto S, Sato Y, Furumichi M, Tanabe M: KEGG for integration and interpretation of large-scale molecular data sets. *Nucleic Acids Res* 2012, 40 (Database issue):D109-114.
16. Kertesz M, Iovino N, Unnerstall U, Gaul U, Segal E: The role of site accessibility in microRNA target recognition. *Nat Genet* 2007, 39(10):1278-1284.
17. Siomi M C, Eder P S, Kataoka N, Wan L, Liu Q, Dreyfuss G: Transportin-mediated nuclear import of heterogeneous nuclear RNP proteins. *The Journal of cell biology* 1997, 138(6):1181-1192.
18. von Roretz C, Macri A M, Gallouzi I E: Transportin 2 regulates apoptosis through the RNA-binding protein HuR. *The Journal of biological chemistry* 2011, 286(29): 25983-25991.
19. Rebane A, Aab A, Steitz J A: Transportins 1 and 2 are redundant nuclear import factors for hnRNP A1 and HuR. *RNA* 2004, 10(4):590-599.
20. Gallouzi I E, Steitz J A: Delineation of mRNA export pathways by the use of cell-permeable peptides. *Science* 2001, 294(5548): 1895-1901.
21. Kumar A: MicroRNA in HCV infection and liver cancer. *Biochim Biophys Acta* 2011.

22. Foster E R, Downs J A: Histone H2A phosphorylation in DNA double-strand break repair. *FEBS J* 2005, 272(13): 3231-3240.
23. Thiriet C, Hayes J J: Chromatin in need of a fix: phosphorylation of H2AX connects chromatin to DNA repair. *Mol Cell* 2005, 18(6):617-622.
24. Ding S W, Voinnet O: Antiviral immunity directed by small RNAs. *Cell* 2007, 130(3):413-426.
25. Grassmann R, Jeang K T: The roles of microRNAs in mammalian virus infection. *Biochim Biophys Acta* 2008, 1779(11):706-711.
26. Umbach J L, Cullen B R: The role of RNAi and microRNAs in animal virus replication and antiviral immunity. *Genes Dev* 2009, 23(10):1151-1164.
27. Kincaid R P, Burke J M, Sullivan C S: RNA virus microRNA that mimics a B-cell oncomiR. *Proceedings of the National Academy of Sciences of the United States of America* 2012, 109(8):3077-3082.
28. Houzet L, Jeang K T: MicroRNAs and human retroviruses. *Biochim Biophys Acta* 2011, 1809(11-12):686-693.
29. Grundhoff A, Sullivan C S: Virus-encoded microRNAs. *Virology* 2011, 411(2):325-343.
30. Pfeffer S, Sewer A, Lagos-Quintana M, Sheridan R, Sander C, Grasser F A, van Dyk L F, Ho C K, Shuman S, Chien M et al: Identification of microRNAs of the herpesvirus family. *Nat Methods* 2005, 2(4):269-276.
31. Grey F, Meyers H, White E A, Spector D H, Nelson J: A human cytomegalovirus-encoded microRNA regulates expression of multiple viral genes involved in replication. *PLoS Pathog* 2007, 3(11):e163.
32. Klase Z, Kale P, Winograd R, Gupta M V, Heydarian M, Berro R, McCaffrey T, Kashanchi F: HIV-1 TAR element is processed by Dicer to yield a viral micro-RNA involved in chromatin remodeling of the viral LTR. *BMC Mol Biol* 2007, 8:63.
33. Parameswaran P, Sklan E, Wilkins C, Burgon T, Samuel M A, Lu R, Ansel K M, Heissmeyer V, Einav S, Jackson W et al: Six RNA viruses and forty-one hosts: viral small RNAs and modulation of small RNA repertoires in vertebrate and invertebrate systems. *PLoS Pathog* 2010, 6(2):e1000764.
34. Chung J H, Ginn-Pease M E, Eng C: Phosphatase and tensin homologue deleted on chromosome 10 (PTEN) has nuclear localization signal-like sequences for nuclear import mediated by major vault protein. *Cancer Res* 2005, 65(10):4108-4116.
35. Chung J H, Eng C: Nuclear-cytoplasmic partitioning of phosphatase and tensin homologue deleted on chromosome 10 (PTEN) differentially regulates the cell cycle and apoptosis. *Cancer Res* 2005, 65(18):8096-8100.
36. Trotman L C, Wang X, Alimonti A, Chen Z, Teruya-Feldstein J, Yang H, Pavletich N P, Carver B S, Cordon-Cardo C, Erdjument-Bromage H et al: Ubiquitination regulates PTEN nuclear import and tumor suppression. *Cell* 2007, 128(1):141-156.
37. Horie Y, Suzuki A, Kataoka E, Sasaki T, Hamada K, Sasaki J, Mizuno K, Hasegawa G, Kishimoto H, Iizuka M et al: Hepatocyte-specific Pten deficiency results in steatohepatitis and hepatocellular carcinomas. *The Journal of clinical investigation* 2004, 113(12): 1774-1783.
38. Stiles B, Wang Y, Stahl A, Bassilian S, Lee W P, Kim Y J, Sherwin R, Devaskar S, Lesche R, Magnuson M A et al: Liver-specific deletion of negative regulator Pten results in fatty liver and insulin hypersensitivity [corrected]. *Proceedings of the National Academy of Sciences of the United States of America* 2004, 101(7):2082-2087.
39. Clement S, Peyrou M, Sanchez-Pareja A, Bourgoin L, Ramadori P, Suter D, Vinciguerra M, Guilloux K, Pascarella S, Rubbia-Brandt L et al: Downregulation of PTEN and IRS-1 by HCV 3a core protein triggers the formation of large lipid droplets in hepatocytes. *Hepatology* 2011.
40. Redon C E, Weyemi U, Parekh P R, Huang D, Burrell A S, Bonner W M: gamma-H2A X and other histone post-translational modifications in the clinic. *Biochim Biophys Acta* 2012, 1819(7):743-756.
41. Seo J, Kim S C, Lee H S, Kim J K, Shon H J, Salleh N L, Desai K V, Lee J H, Kang E S, Kim J S et al: Genome-wide profiles of H2A X and gamma-H2A X differentiate endogenous and exogenous DNA damage hotspots in human cells. *Nucleic Acids Res* 2012, 40(13): 5965-5974.
42. Hofacker I L: Vienna RNA secondary structure server. *Nucleic Acids Res* 2003, 31(13):3429-3431.
43. Tesfaye A, Stift J, Maric D, Cui Q, Dienes H P, et al. (2013) Chimeric mouse model for the infection of hepatitis B and C viruses. PloS one 8: e77298.
44. Song M S, Salmena L, Pandolfi P P (2012) The functions and regulation of the PTEN tumour suppressor. Nature reviews Molecular cell biology 13: 283-296.
45. He L, Hou X, Kanel G, Zeng N, Galicia V, et al. (2010) The critical role of AKT2 in hepatic steatosis induced by PTEN loss. *Am J Pathol* 176: 2302-2308.
46. He X, Saji M, Radhakrishnan D, Romigh T, Ngeow J, et al. (2012) PTEN Lipid Phosphatase Activity and Proper Subcellular Localization Are Necessary and Sufficient for Down-Regulating AKT Phosphorylation in the Nucleus in Cowden Syndrome. The Journal of clinical endocrinology and metabolism 97: E2179-2187.
47. Weng L P, Brown J L, Eng C (2001) PTEN coordinates G(1) arrest by down-regulating cyclin D1 via its protein phosphatase activity and up-regulating p27 via its lipid phosphatase activity in a breast cancer model. Human molecular genetics 10: 599-604.
48. Banaudha K, Orenstein J M, Korolnek T, St Laurent G C, 3rd, Wakita T, et al. (2010) Primary hepatocyte culture supports hepatitis C virus replication: a model for infection-associated hepatocarcinogenesis. Hepatology 51: 1922-1932.
49. Pelengaris S, Rudolph B, Littlewood T (2000) Action of Myc in vivo—proliferation and apoptosis. Current opinion in genetics & development 10: 100-105.
50. Warfel N A, El-Deiry W S (2013) p21WAF1 and tumourigenesis: 20 years after. Current opinion in oncology 25: 52-58.
51. Mendell J T, Olson E N (2012) MicroRNAs in stress signaling and human disease. Cell 148: 1172-1187.
52. Calin G A, Dumitru C D, Shimizu M, Bichi R, Zupo S, et al. (2002) Frequent deletions and down-regulation of micro-RNA genes miR15 and miR16 at 13q14 in chronic lymphocytic leukemia. Proc Natl Acad Sci USA 99: 15524-15529.
53. Calin G A, Croce C M (2006) MicroRNA signatures in human cancers. Nature reviews Cancer 6: 857-866.
54. Kumar A (2011) MicroRNA in HCV infection and liver cancer. Biochimica et biophysica acta.
55. Medina P P, Nolde M, Slack F J (2010) OncomiR addiction in an in vivo model of microRNA-21-induced pre-B-cell lymphoma. Nature 467: 86-90.
56. Pineau P, Volinia S, McJunkin K, Marchio A, Battiston C, et al. (2010) miR-221 overexpression contributes to liver tumorigenesis. Proc Natl Acad Sci USA 107: 264-269.

57. Medina P P, Slack F J (2008) microRNAs and cancer: an overview. Cell Cycle 7: 2485-2492.

58. Kota J, Chivukula R R, O'Donnell K A, Wentzel E A, Montgomery C L, et al. (2009) Therapeutic microRNA delivery suppresses tumorigenesis in a murine liver cancer model. *Cell* 137: 1005-1017.

59. Hatziapostolou M, Polytarchou C, Aggelidou E, Drakaki A, Poultsides G A, et al. (2011) An HNF4alpha-miRNA inflammatory feedback circuit regulates hepatocellular oncogenesis. Cell 147: 1233-1247.

60. Kerr T A, Korenblat K M, Davidson N O (2011) MicroRNAs and liver disease. Translational research: the journal of laboratory and clinical medicine 157: 241-252.

70. Obad S, dos Santos C O, Petri A, Heidenblad M, Broom O, et al. (2011) Silencing of microRNA families by seed-targeting tiny LNAs. Nature genetics 43: 371-378.

71. Safaee, N. et al. Structure of the Parallel Duplex of Poly(A) RNA: Evaluation of a 50 Year-Old Prediction. *Angew Chem Int Ed Engl* 52, 10370-10373, doi:10.1002/anie.201303461 (2013). PMID:23813654.

72. Watson, J. D. & Crick, F. H. Molecular structure of nucleic acids; a structure for deoxyribose nucleic acid. *Nature* 171, 737-738 (1953). PMID:13054692.

73. Sasisekharan, V. & Pattabiraman, N. Structure of DNA predicted from stereochemistry of nucleoside derivatives. *Nature* 275, 159-162 (1978). PMID:692688.

74. Wang, A. H. et al. Molecular structure of a left-handed double helical DNA fragment at atomic resolution. *Nature* 282, 680-686 (1979). PMID:514347.

75. Sasisekharan, V., Pattabiraman, N. & Gupta, G. Some implications of an alternative structure for DNA. *Proc Natl Acad Sci USA* 75, 4092-4096 (1978). PMID:279899.

76. Herbert, A. G. & Rich, A. A method to identify and characterize Z-DNA binding proteins using a linear oligodeoxynucleotide. *Nucleic Acids Res* 21, 2669-2672 (1993). PMID:8332463.

77. Herbert, A. et al. A Z-DNA binding domain present in the human editing enzyme, double-stranded RNA adenosine deaminase. *Proc Natl Acad Sci USA* 94, 8421-8426 (1997). PMID:9237992.

78. Herbert, A. et al. The Zalpha domain from human ADAR1 binds to the Z-DNA conformer of many different sequences. *Nucleic Acids Res* 26, 3486-3493 (1998). PMID:9671809.

79. Schwartz, T., Rould, M. A., Lowenhaupt, K., Herbert, A. & Rich, A. Crystal structure of the Zalpha domain of the human editing enzyme ADAR1 bound to left-handed Z-DNA. *Science* 284, 1841-1845 (1999). PMID: 10364558.

80. Schade, M. et al. The solution structure of the Zalpha domain of the human RNA editing enzyme ADAR1 reveals a prepositioned binding surface for Z-DNA. *Proc Natl Acad Sci USA* 96, 12465-12470 (1999). PMID: 10535945.

81. Zhou, N., Germann, M. W., van de Sande, J. H., Pattabiraman, N. & Vogel, H. J. Solution structure of the parallel-stranded hairpin d(T8<text text>C4A8) as determined by two-dimensional NMR. *Biochemistry* 32, 646-656 (1993). PMID:8380706.

82. Pattabiraman, N. Can the double helix be parallel? *Biopolymers* 25, 1603-1606, doi:10.1002/bip.360250903 (1986).

83. Moradpour, D., Penin, F. & Rice, C. M. Replication of hepatitis C virus. *Nat Rev Microbiol* 5, 453-463, doi: nrmicro1645 [pii] 10.1038/nrmicrol645 (2007). PMID: 17487147.

84. Garaigorta, U. & Chisari, F. V. Hepatitis C virus blocks interferon effector function by inducing protein kinase R phosphorylation. *Cell Host Microbe* 6, 513-522, doi: S1931-3128(09)00381-3 [pii]10.1016/j.chom.2009.11.004 (2009). PMID:20006840.

85. Gale, M., Jr. & Foy, E. M. Evasion of intracellular host defence by hepatitis C virus. *Nature* 436, 939-945, doi: nature04078 [pii] 10.1038/nature04078 (2005). PMID: 16107833.

86. Liu, H. M. & Gale, M. Hepatitis C Virus Evasion from RIG-I-Dependent Hepatic Innate Immunity. *Gastroenterol Res Pract* 2010, 548390, doi:10.1155/2010/548390 (2010). PMID:21274284.

87. Ding, S. W. & Voinnet, O. Antiviral immunity directed by small RNAs. *Cell* 130, 413-426, doi:S0092-8674(07)00977-4 [pii] 10.1016/j.cell.2007.07.039 (2007). PMID: 17693253.

88. Grassmann, R. & Jeang, K. T. The roles of microRNAs in mammalian virus infection. *Biochim Biophys Acta* 1779, 706-711, doi:S1874-9399(08)00116-8 [pii] 10.1016/j.bbagrm.2008.05.005 (2008). PMID:18549828.

89. Umbach, J. L. & Cullen, B. R. The role of RNAi and microRNAs in animal virus replication and antiviral immunity. *Genes Dev* 23, 1151-1164, doi:23/10/1151 [pii] 10.1101/gad.1793309 (2009). PMID:19451215.

90. Kincaid, R. P., Burke, J. M. & Sullivan, C. S. RNA virus microRNA that mimics a B-cell oncomiR. *Proc Natl Acad Sci USA* 109, 3077-3082, doi:10.1073/pnas.1116107109 (2012). PMID:22308400.

91. Houzet, L. & Jeang, K. T. MicroRNAs and human retroviruses. Biochimica et biophysica acta 1809, 686-693, doi:10.1016/j.bbagrm.2011.05.009 (2011). PMID: 21640212.

92. Grundhoff, A. & Sullivan, C. S. Virus-encoded microRNAs. Virology 411, 325-343, doi: 10.1016/j.virol.2011.01.002 (2011). PMID:21277611.

93. Kincaid, R. P. & Sullivan, C. S. Virus-Encoded microRNAs: An Overview and a Look to the Future. *PLoS pathogens* 8, e1003018, doi:10.1371/joumal.ppat.1003018 (2012). PMID:23308061.

94. Pfeffer, S. et al. Identification of microRNAs of the herpesvirus family. *Nat Methods* 2, 269-276, doi: nmeth746 [pii] 10.1038/nmeth746 (2005). PMID: 15782219.

95. Grey, F., Meyers, H., White, E. A., Spector, D. H. & Nelson, J. A human cytomegalovirus-encoded microRNA regulates expression of multiple viral genes involved in replication. *PLoS Pathog* 3, e163, doi:07-PLPA-RA-0411 [pii]10.1371/joumal.ppat.0030163 (2007). PMID: 17983268.

96. Klase, Z. et al. HIV-1 TAR element is processed by Dicer to yield a viral micro-RNA involved in chromatin remodeling of the viral LTR. *BMC Mol Biol* 8, 63, doi:1471-2199-8-63 [pii] 10.1186/1471-2199-8-63 (2007). PMID: 17663774.

97. Parameswaran, P. et al. Six RNA viruses and forty-one hosts: viral small RNAs and modulation of small RNA repertoires in vertebrate and invertebrate systems. *PLoS Pathog* 6, e1000764, doi:10.1371/joumal.ppat.1000764 (2010). PMID:20169186.

98. Banaudha, K. et al. Primary hepatocyte culture supports hepatitis C virus replication: a model for infection-associated hepatocarcinogenesis. *Hepatology* 51, 1922-1932, doi:10.1002/hep.23616 (2010). PMID:20512986.

99. Banaudha, K. et al. MicroRNA silencing of tumor suppressor DLC-1 promotes efficient hepatitis C virus replication in primary human hepatocytes. *Hepatology* 53, 53-61, doi:10.1002/hep.24016 (2011). PMID: 20967756.

100. Tani, H. et al. Genome-wide determination of RNA stability reveals hundreds of short-lived noncoding transcripts in mammals. *Genome Res* 22, 947-956, doi: 10.1101/gr.130559.111 (2012). PMID:22369889.

101. Malathi, K. et al. RNase L releases a small RNA from HCV RNA that refolds into a potent PAMP. *Rna* 16, 2108-2119, doi:10.1261/rna.2244210 (2010). PMID: 20833746.

102. Malathi, K., Dong, B., Gale, M., Jr. & Silverman, R. H. Small self-RNA generated by RNase L amplifies antiviral innate immunity. *Nature* 448, 816-819, doi:10.1038/nature06042 (2007). PMID:17653195.

103. Tani, H. & Akimitsu, N. Genome-wide technology for determining RNA stability in mammalian cells: historical perspective and recent advantages based on modified nucleotide labeling. *RNA Biol* 9, 1233-1238, doi:10.4161/rna.22036 (2012). PMID:23034600.

104. Kersetz, M. Lovino, N. Unnerstall, U., Gaul, U., Segal, E. (2007). The role of site accessibility in microRNA target recognition. *Nature Genetics* 39:1278-1284.

What is claimed is:

1. A method of inhibiting HCV infection associated hepatocellular carcinoma in a patient in need thereof, comprising:

administering to the patient in need thereof an antagonist of a virus derived vmr11 microRNA;

wherein the antagonist is a 19 to 25 nucleotide-long single stranded oligonucleotide that comprises the sequence 5'-CUACUAC-3', and wherein vmr11 comprises a nucleotide sequence sharing at least 80% sequence identity to: 5'-GUUCAUCAUCAUAUCCCAUGCC-3' (SEQ ID NO:1).

2. The method of claim 1, wherein nucleotides at positions 4-10 of the nucleotide sequence sharing at least 80% nucleotide sequence identity to SEQ ID NO:1 are 5'-CAUCAUC-3'.

3. The method of claim 1, wherein vmr11 comprises a nucleotide sequence sharing at least 95% sequence identity to: 5'-GUUCAUCAUCAUAUCCCAUGCC-3' (SEQ ID NO:1).

4. The method of claim 1, wherein vmr11 comprises a nucleotide sequence of:

5'-GUUCAUCAUCAUAUCCCAUGCC-3' (SEQ ID NO:1).

5. The method of claim 2, wherein the antagonist of vmr11 is a 22 nucleotide long single stranded oligonucleotide that comprises the sequence 5'-CUACUAC-3'.

6. The method of claim 2, wherein the antagonist of vmr11 is a 22 nucleotide long single stranded oligonucleotide that comprises the sequence 5'-CUACUAC-3' at nucleotide positions 4-10.

7. The method of claim 1, wherein the oligonucleotide comprises one or more nucleotide modifications that increase stability of the oligonucleotide in the presence of a nuclease.

8. The method of claim 7, wherein one or more of the nucleotide units of the oligonucleotide are locked nucleic acid (LNA) units.

9. The method of claim 7, wherein one or more of the nucleotide units of the oligonucleotide are 2' substituted nucleotide analogues.

10. The method of claim 7, wherein one or more of the nucleotide units of the oligonucleotide are 2' substituted nucleotide analogues, selected from the group consisting of: 2'-deoxy, 2'-deoxy-2'-fluoro, 2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA), and combinations thereof.

11. The method of claim 7, wherein one or more of the nucleotide units of the oligonucleotide contain a 2'-deoxy-2'-fluoro group.

12. The method of claim 7, wherein one or more of the internucleoside linkages between the nucleotide units of the oligonucleotide are phosphorothioate internucleoside linkages.

* * * * *

UNITED STATES PATENT AND TRADEMARK OFFICE

CERTIFICATE OF CORRECTION

PATENT NO. : 10,487,328 B2
APPLICATION NO. : 15/129043
DATED : November 26, 2019
INVENTOR(S) : Kumar et al.

It is certified that error appears in the above-identified patent and that said Letters Patent is hereby corrected as shown below:

On the Title Page

Item (71), please replace "Ajit Kumar, Bethesda, MD (US)" with -- THE GEORGE WASHINGTON UNIVERSITY, Washington, DC (US) --.

Signed and Sealed this
Twenty-third Day of June, 2020

Andrei Iancu
*Director of the United States Patent and Trademark Office*